(12) United States Patent
Morningstar et al.

(10) Patent No.: US 11,219,515 B2
(45) Date of Patent: *Jan. 11, 2022

(54) INCONTINENCE TREATMENT DEVICE HAVING A FIRST ANCHOR ASSEMBLY AND A SECOND ANCHOR ASSEMBLY

(71) Applicant: Coloplast A/S, Humlebaek (DK)

(72) Inventors: Randy Lee Morningstar, Brooklyn Park, MN (US); Michael M. Witzmann, Shoreview, MN (US); Mark A. Moschel, Plymouth, MN (US)

(73) Assignee: Coloplast A/S, Humlebaek (DK)

( * ) Notice: Subject to any disclaimer, the term of this patent is extended or adjusted under 35 U.S.C. 154(b) by 127 days.

This patent is subject to a terminal disclaimer.

(21) Appl. No.: 16/808,379

(22) Filed: Mar. 4, 2020

(65) Prior Publication Data

US 2020/0197145 A1 Jun. 25, 2020

Related U.S. Application Data

(63) Continuation of application No. 15/632,429, filed on Jun. 26, 2017, now Pat. No. 10,617,504, which is a continuation of application No. 14/754,757, filed on Jun. 30, 2015, now Pat. No. 9,717,581, which is a continuation-in-part of application No. 14/181,607, filed on Feb. 14, 2014, now Pat. No. 9,370,363, which is a continuation-in-part of application No. 12/717,957, filed on Mar. 5, 2010, now Pat. No. 8,696,544, which is a continuation-in-part of application No. 12/621,517, filed on Nov. 19, 2009, now Pat. No. 8,585,579, which is a (Continued)

(51) Int. Cl.
*A61F 2/00* (2006.01)
*A61B 17/04* (2006.01)
*A61B 17/06* (2006.01)

(52) U.S. Cl.
CPC ........ *A61F 2/0045* (2013.01); *A61B 17/0401* (2013.01); *A61B 17/06109* (2013.01); *A61B 17/0487* (2013.01); *A61B 2017/0409* (2013.01); *A61B 2017/0414* (2013.01); *A61B 2017/0448* (2013.01); *A61B 2017/0464* (2013.01); *A61B 2017/0496* (2013.01); *A61B 2017/06042* (2013.01); *A61B 2017/06076* (2013.01); *A61F 2220/0008* (2013.01)

(58) Field of Classification Search
CPC ...... A61B 2017/045; A61B 2017/0451; A61B 2017/0464; A61B 17/0401; A61B 17/06109; A61B 17/0487; A61B 2017/0409; A61B 2017/0414; A61B 2017/0448; A61B 2017/0496; A61B 2017/06042; A61B 2017/06076; A61F 2/0045; A61F 2220/0008
See application file for complete search history.

(56) References Cited

U.S. PATENT DOCUMENTS

2010/0063542 A1* 3/2010 van der Burg ..... A61B 17/0401 606/232

* cited by examiner

*Primary Examiner* — Kaylee R Wilson
(74) *Attorney, Agent, or Firm* — Coloplast Corp., Coloplast A/S; Nick Baumann

(57) ABSTRACT

An incontinence treatment device has first and second anchor assemblies. At least one of the first anchor assembly and the second anchor assembly is adjustable along the device and has a collar disposed over a body with a strand coupled to the device and located between the body and the collar.

11 Claims, 55 Drawing Sheets

Related U.S. Application Data continuation-in-part of application No. 12/414,709, filed on Mar. 31, 2009, now Pat. No. 8,585,578.

(60) Provisional application No. 61/150,276, filed on Feb. 5, 2009.

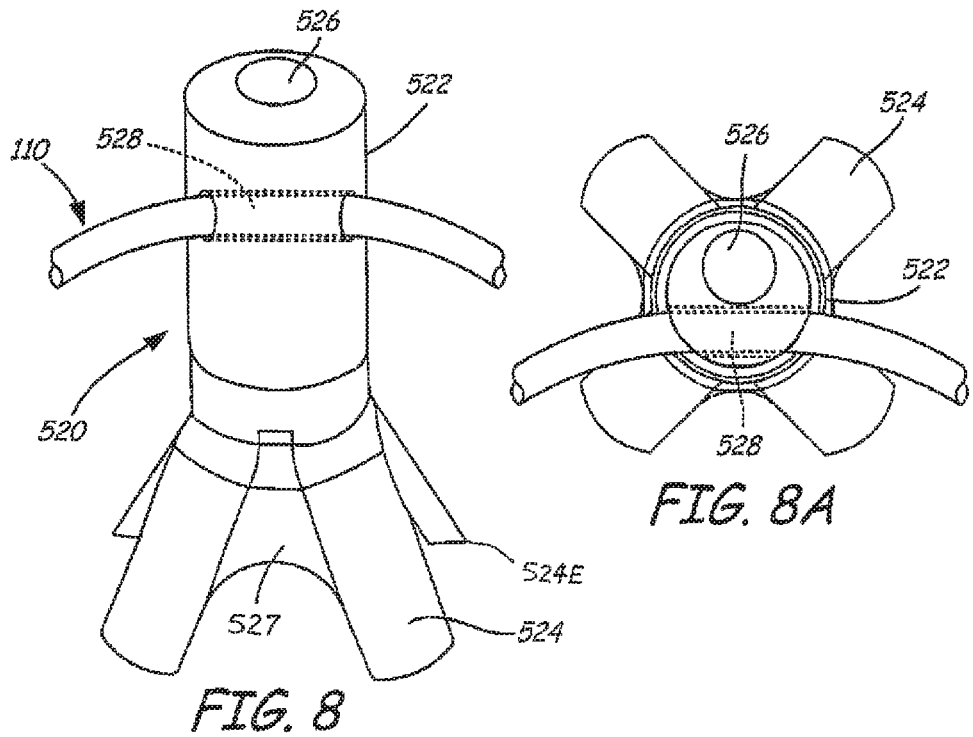
FIG. 8
FIG. 8A
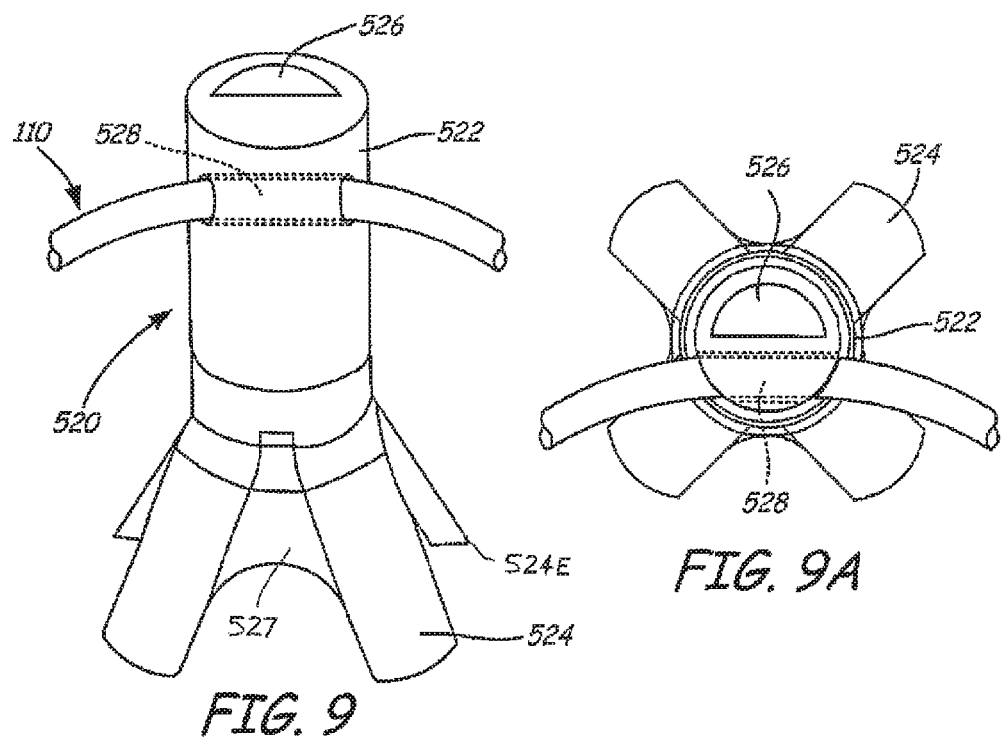
FIG. 9
FIG. 9A

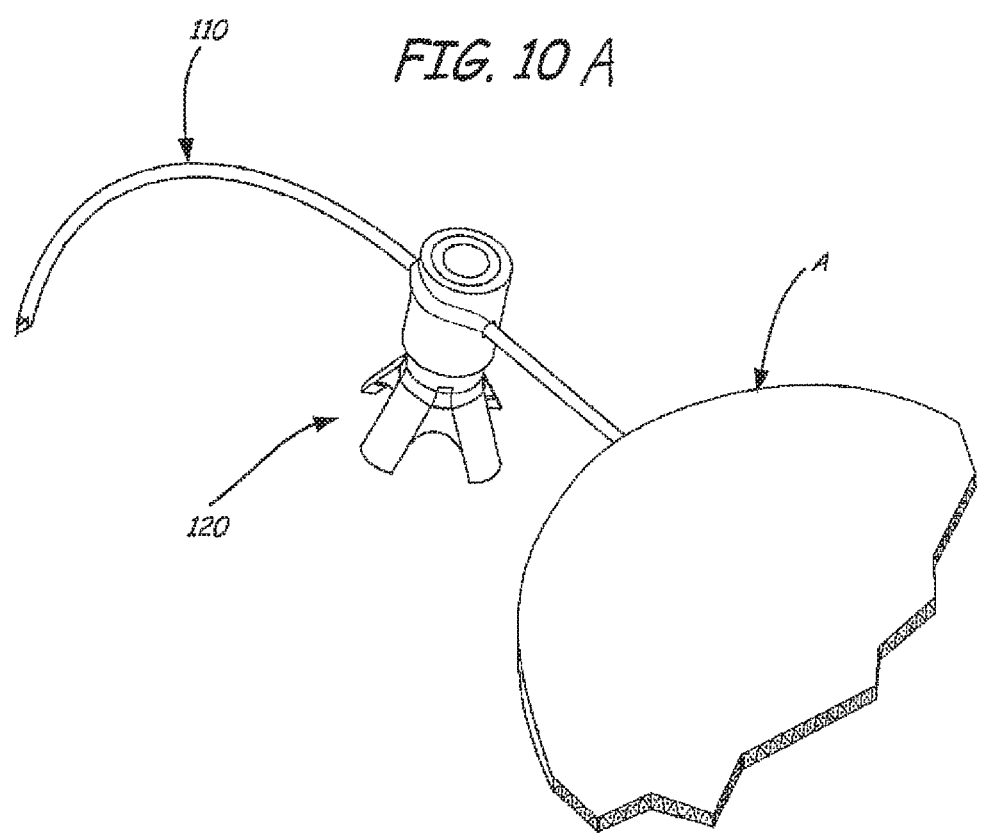

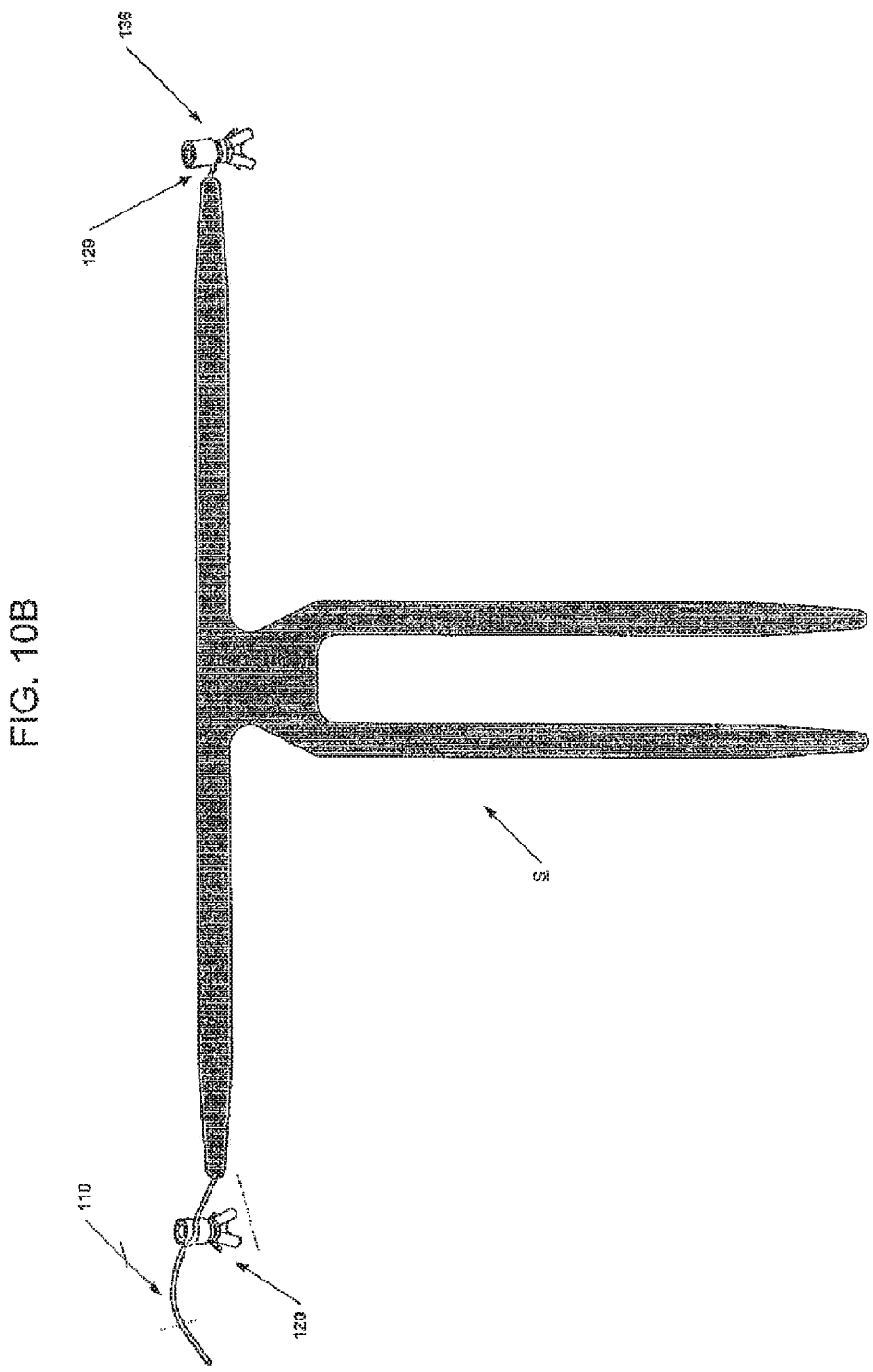

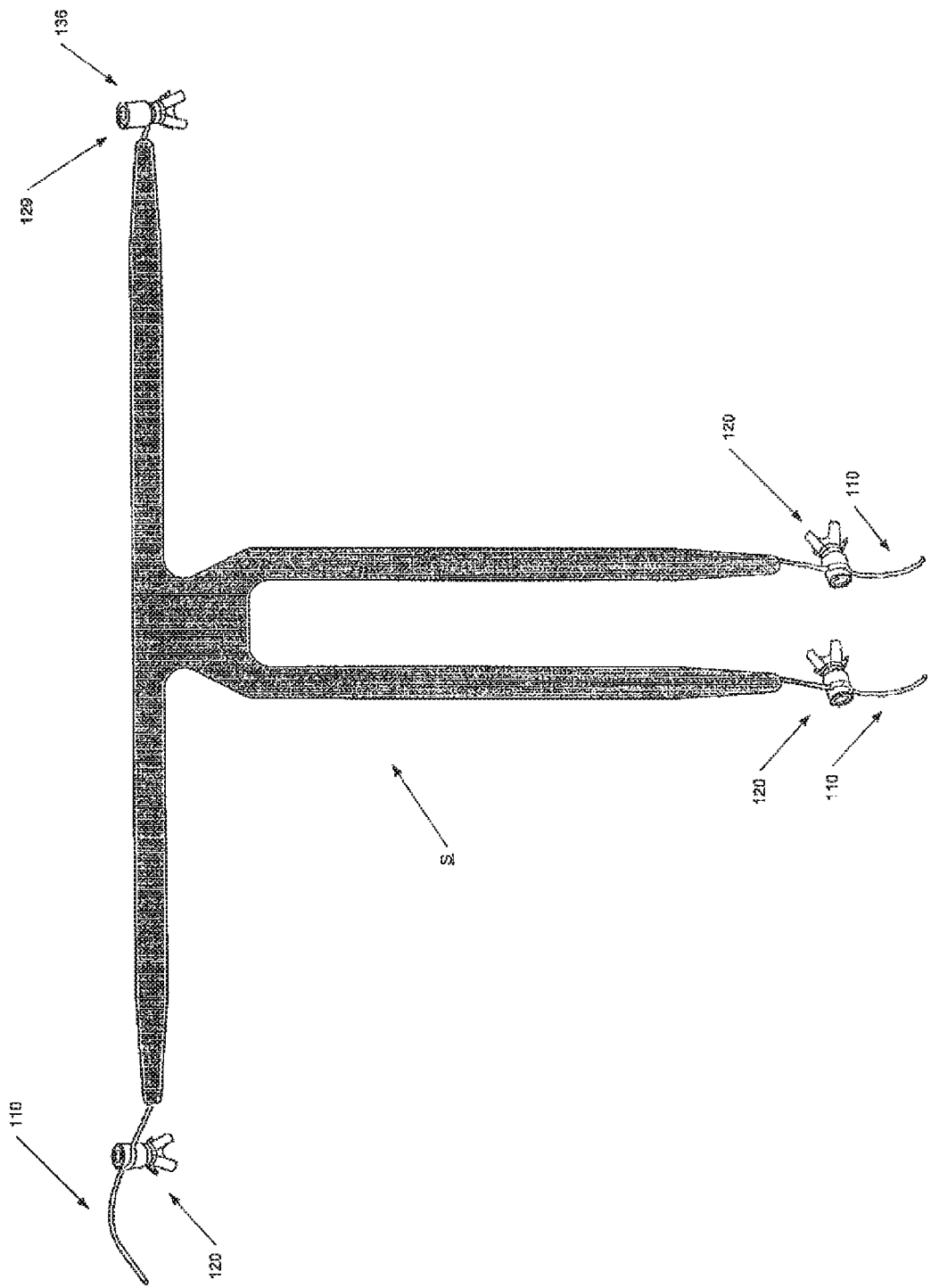

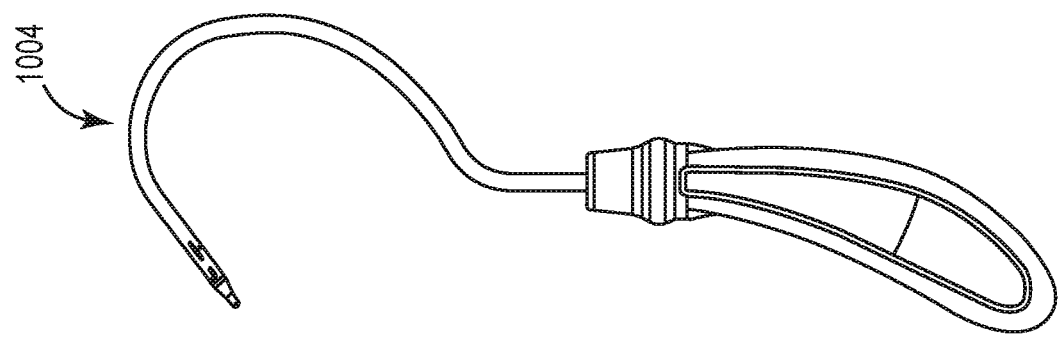
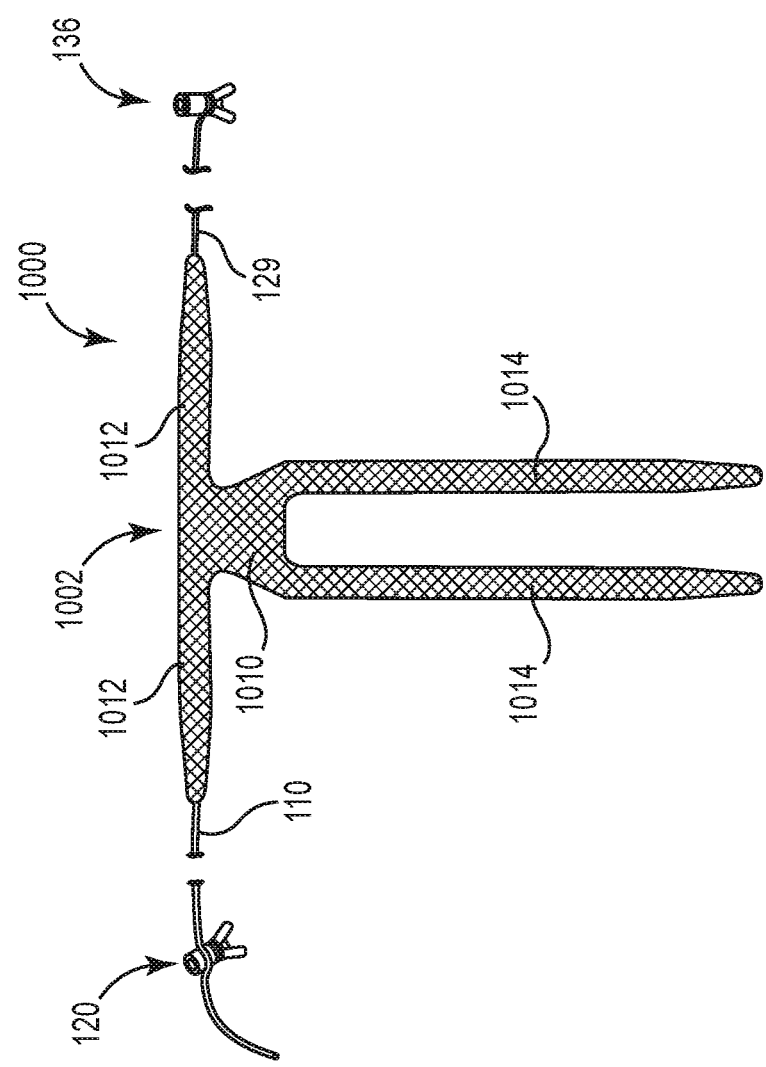
FIG. 16

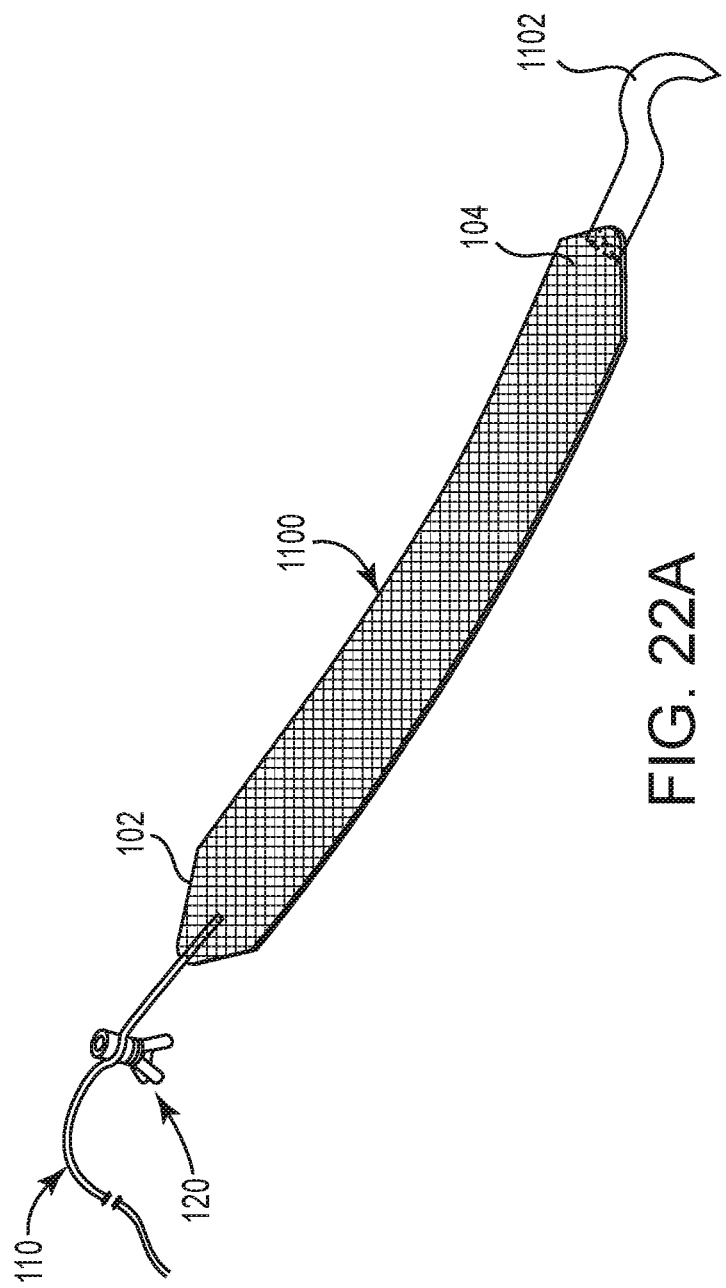
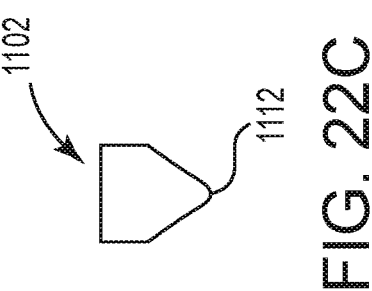
FIG. 22A
FIG. 22B
FIG. 22C

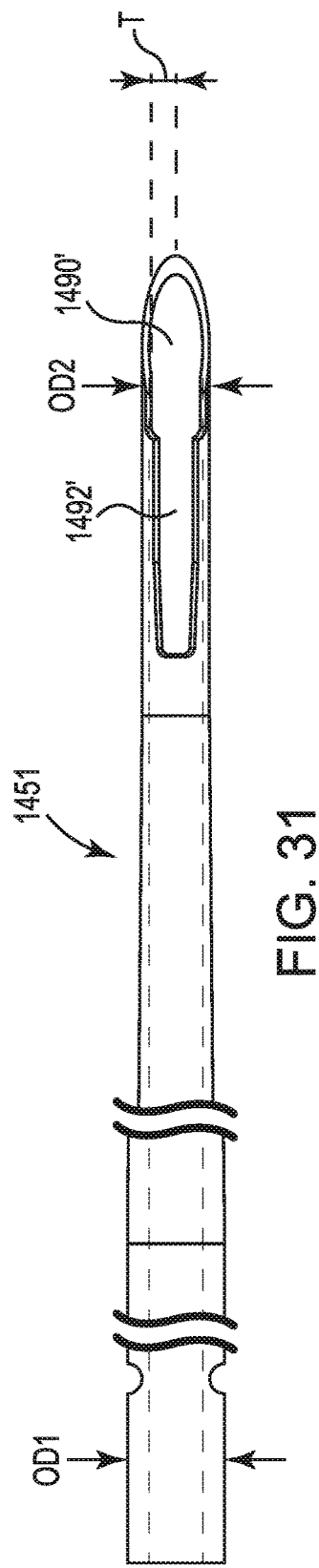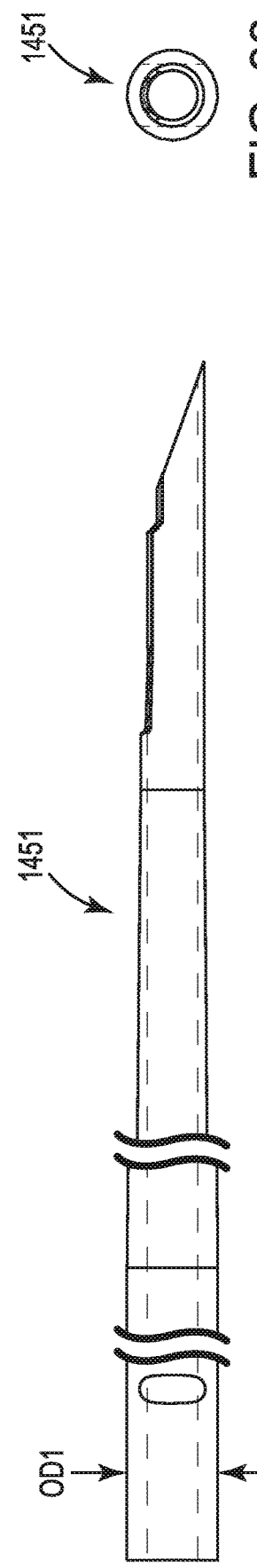
FIG. 31
FIG. 32
FIG. 33

INCONTINENCE TREATMENT DEVICE HAVING A FIRST ANCHOR ASSEMBLY AND A SECOND ANCHOR ASSEMBLY

This application is a Continuation of prior application Ser. No. 15/632,429 filed on Jun. 26, 2017, which is a Continuation-in-Part of prior application Ser. No. 14/754,757, filed on Jun. 30, 2015, now U.S. Pat. No. 9,717,581, which is a Continuation-in-Part of prior application Ser. No. 14/181,607, filed on Feb. 14, 2014, now U.S. Pat. No. 9,370,363, which is a Continuation-in-Part of prior application Ser. No. 12/717,957, filed Mar. 5, 2010, now U.S. Pat. No. 8,696,544, which is a Continuation-in-Part of prior application Ser. No. 12/621,517, filed on Nov. 19, 2009, now U.S. Pat. No. 8,585,579, which prior application was a Continuation-in-Part of prior application Ser. No. 12/414,709, filed on Mar. 31, 2009, now U.S. Pat. No. 8,585,578, which claimed the benefit of U.S. Provisional Application No. 61/150,276, filed on 5 Feb. 2009.

TECHNICAL FIELD

This disclosure relates generally to medical devices. More particularly, this disclosure relates to implantable devices, tools, and methods for anatomical support.

BACKGROUND

Devices for anatomical support, and particularly those for treatment of urinary incontinence and pelvic organ prolapse have been proposed in recent years. Such devices have included suburethral sling devices for urinary incontinence, and mesh devices for pelvic organ prolapse. Sling devices are surgically implanted under a patient's urethra to provide support to the urethra so that during a provocative event such as coughing or laughing, urine is inhibited from leaking out of the urethra. Devices for treatment of pelvic organ prolapse are also surgically implanted, to inhibit herniation or prolapse of an organ (e.g., the bladder) into the vaginal space. Such support from the sling and mesh devices replaces natural anatomical support that is lacking in the patient. But implanting and anatomically securing some devices may be difficult and time consuming. Further, in the case of urinary incontinence, some sling devices may provide unreliable anatomical fixation and unacceptable adjustment or tensioning for supporting the urethra, thereby leading to suboptimal or even unacceptable results for treatment of urinary incontinence.

SUMMARY

This disclosure describes novel implantable devices that provide support to a urethra or other anatomical structure. This disclosure also describes novel tools and methods for use with the implantable devices.

In one aspect, an implantable device for anatomical support includes a sling, a first interconnecting member that is coupled to the sling, and a second interconnecting member that is coupled to the sling. An adjustable anchor is slidably coupled to the first interconnecting member to permit bi-directional movement along the first interconnecting member, and configured to exert a compressive force generating frictional interference between the adjustable anchor and the first interconnecting member, to inhibit the bi-directional movement of the adjustable anchor along the first interconnecting member unless sufficient force is applied to overcome the frictional interference. Also, a fixed anchor is fixedly coupled to the second interconnecting member. In another aspect, the first interconnecting member and the second interconnecting member are sutures. In another aspect, the first interconnecting member and the second interconnecting member are materials having an overall width approximating that of a surgical suture.

In another aspect, an implantable device for anatomical support includes a sling, a first interconnecting member that is coupled to the sling, and a second interconnecting member that is coupled to the sling. An anchor is provided in freely sliding engagement with the first interconnecting member. A tensioning element is slidably coupled to the first interconnecting member to permit movement along the first interconnecting member and configured to exert a compressive force generating frictional interference between the tensioning element and the first interconnecting member, to inhibit the movement of the tensioning element along the first interconnecting member unless sufficient force is applied to overcome the frictional interference. Also, a fixed anchor is fixedly coupled to the second interconnecting member. In another aspect, the first interconnecting member and the second interconnecting member are sutures. In another aspect, the first interconnecting member and the second interconnecting member are materials having an overall width approximating that of a surgical suture.

In another aspect, an implantable device for anatomical support includes an anatomical support member and an interconnecting member that is coupled to the anatomical support member. An adjustable anchor is slidably coupled to the interconnecting member to permit bi-directional movement along the interconnecting member and configured to exert a compressive force generating frictional interference between the adjustable anchor and the interconnecting member, to inhibit the bi-directional movement of the adjustable anchor along the interconnecting member unless sufficient force is applied to overcome the frictional interference. In another aspect, the anatomical support member is a shaped mesh material for treatment of prolapse. In another aspect, the interconnecting member is a suture. In another aspect, the interconnecting member is a material having an overall width approximating that of a surgical suture.

In another aspect, an implantable device for anatomical support includes an anatomical support member, an interconnecting member that is coupled to the anatomical support member, and an anchor in freely sliding engagement with the interconnecting member. A tensioning element is slidably coupled to the interconnecting member to permit movement along the interconnecting member and configured to exert a compressive force generating frictional interference between the tensioning element and the interconnecting member, to inhibit the movement of the tensioning element along the interconnecting member unless sufficient force is applied to overcome the frictional interference. In another aspect, the interconnecting member is a suture. In another aspect, the interconnecting member is a material having an overall width approximating that of a surgical suture.

In another aspect an adjustable anchor, for use with an anatomical support member having an interconnecting member extending therefrom, includes a body having a proximal end and a distal end, wherein the distal end includes a flange section that is wider than the proximal end. A collar surrounds, and generates a compressive force against, the proximal end of the body, wherein the interconnecting member is disposed between the body and the collar, subject to the compressive force that generates frictional interference to inhibit bi-directional movement of the adjustable anchor along the interconnecting member unless sufficient force is applied to overcome the frictional interference. In another aspect, a plurality of flanges protrude from the flange section, separated by webs. In another aspect, at least one flange has an angled edge. In another aspect, at least one web is self-creasing.

In another aspect an adjustable anchor and a tool, for placing in a patient an anatomical support member having an interconnecting member extending therefrom, includes an anchor body having a proximal end, a distal end, and a channel extending longitudinally through the anchor body, wherein the distal end includes a flange section that is wider than the proximal end. An anchor collar surrounds, and generates a compressive force against, the proximal end of the anchor body, wherein the interconnecting member is disposed between the anchor body and the anchor collar, subject to the compressive force that generates frictional interference to inhibit bi-directional movement of the adjustable anchor along the interconnecting member unless sufficient force is applied to overcome the frictional interference. A tool shaft has a proximal end, a shoulder, and a distal tip proximate the shoulder. A helical curve in the shaft terminates at the shoulder. The distal tip is configured to be placed in the channel through the anchor body such that the shoulder abuts the anchor body adjacent to the flange section. The helical curve is configured to guide the distal tip from a vaginal incision, around a descending ramus, and through an obturator foramen. In another aspect, a handle is coupled to the proximal end.

In another aspect a surgical method is provided for use with (i) an implantable device having an anatomical support member, a fixed anchor coupled to the implantable device, an adjustable anchor, and an interconnecting member that couples the implantable device to the adjustable anchor in frictional sliding engagement, (ii) a first tool corresponding to a first side of a patient, and (iii) a second tool corresponding to a second side of a patient. The method includes placement of the fixed anchor on a distal tip of the first tool. A vaginal incision in the patient is entered with the fixed anchor on the distal tip of the first tool. The first tool is rotated in a direction corresponding to the first side of the patient such that the fixed anchor travels in a path around a descending pubic ramus on the first side of the patient, continuing in the path until the fixed anchor is placed in obturator tissue on the first side of the patient; and the first tool is removed from the patient. An adjustable anchor is placed on a distal tip of the second tool. The vaginal incision in the patient is entered with the adjustable anchor on the distal tip of the second tool. The second tool is rotated in a direction corresponding to the second side of the patient such that the adjustable anchor travels in a path around a descending pubic ramus on the second side of the patient, continuing in the path until the adjustable anchor is placed in obturator tissue on the second side of the patient; and the second tool is removed from the patient. The interconnecting member, in frictional sliding engagement with the adjustable anchor, is pulled to adjust a length of the interconnecting member between the anatomical support member and the adjustable anchor.

In another aspect an implantable anatomical support includes a support body and at least three arms extending from the support body, an interconnecting member that is coupled to one each of at least two of the arms extending from the support body, and an adjustable anchor slidably coupled to each of at least two of the interconnecting members. The adjustable anchor is configured to permit bi-directional movement along the interconnecting member and configured to exert a compressive force generating frictional interference between the adjustable anchor and the interconnecting member to inhibit the bi-directional movement of the adjustable anchor along the interconnecting member unless sufficient force is applied to overcome the frictional interference.

Another aspect provides a method of addressing pelvic dysfunction in a patient. The method includes forming an incision, and placing an anchor that is attached to a support member by an interconnecting member onto a distal tip of a tool. The method additionally includes inserting the distal tip of the tool and the anchor into the incision, guiding the anchor to an obturator foramen, and pushing the anchor through a membrane extending over the obturator foramen. The method further includes adjusting the support member by sliding the interconnecting member relative to the anchor.

BRIEF DESCRIPTION OF THE DRAWINGS

FIG. 8 is a magnified illustration of one of the components shown in FIG. 6.

FIG. 8A is a top view of the component shown in FIG. 8.

FIG. 9 is a magnified illustration of an alternative component for the device shown in FIG. 6.

FIG. 9A is a top view of the component shown in FIG. 9.

FIG. 10A is a partial illustration of another embodiment of an implantable device for anatomical support.

FIG. 10B is an illustration of another embodiment of an implantable device for anatomical support.

FIG. 10C is an illustration of another embodiment of an implantable device for anatomical support

FIG. 16 is a top view of one embodiment of a system for addressing pelvic dysfunction in a male including an adjustable support member and an introducer tool.

FIG. 22A is a perspective view of one embodiment of a support member including an adjustable anchor and a hanger.

FIG. 22B is a side view and FIG. 22C is a front view of the hanger illustrated in FIG. 22A.

FIG. 31 is a top view, FIG. 32 is a side view, and FIG. 33 is a cross-sectional view of the cannula of the introducer illustrated in FIG. 28.

DETAILED DESCRIPTION

Figure 1:
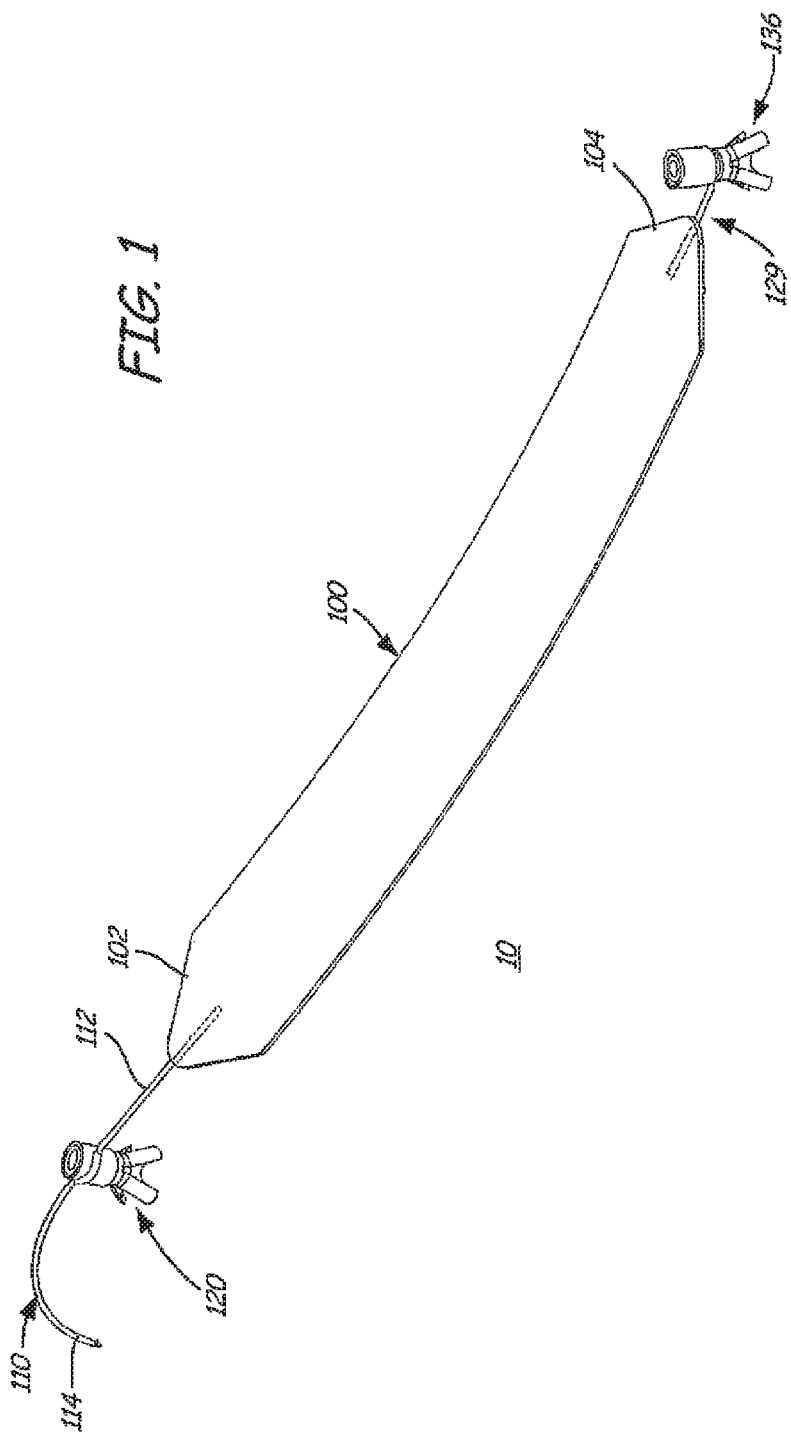
FIG. 1 is an illustration of one embodiment of an implantable device for anatomical support.

One embodiment of an implantable device for anatomical support (device 10) is illustrated in FIG. 1. Therein, an anatomical support member in a form of a suburethral sling includes anchors that are deployed into a patient's tissues. The anchors are coupled to the sling by interconnecting members. In this regard a fixed anchor is fixedly connected in fixed relation to the sling by a first interconnecting member, and an adjustable anchor is slidably coupled in adjustable relation to the sling by a second interconnecting member. The adjustable anchor, as will be described, is configured to permit bi-directional movement along the second interconnecting member in frictional sliding engagement therewith. In one embodiment, the interconnecting members are lengths of suture or suture-like material.

Figure 2:
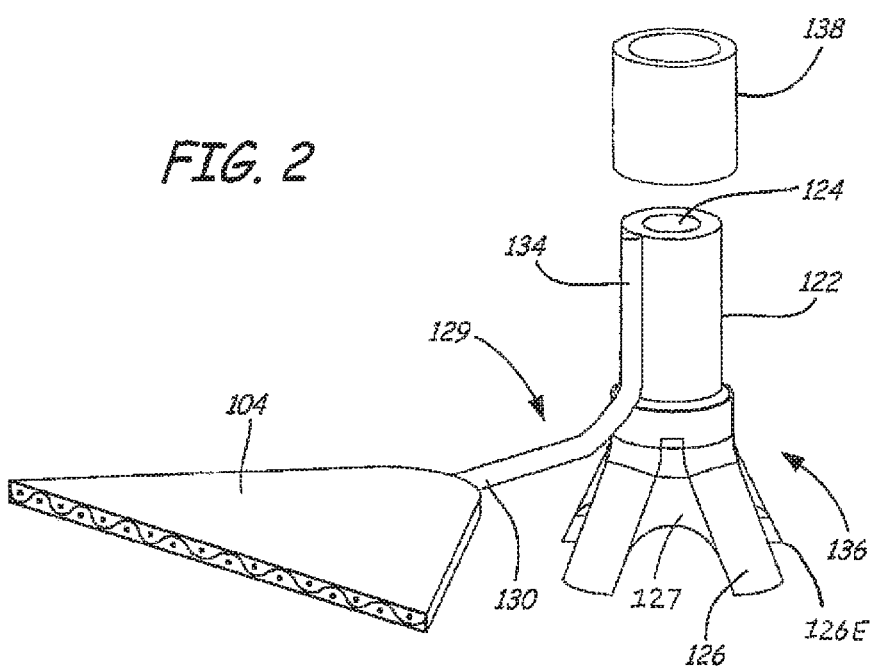
FIG. 2 is an exploded illustration of a component of the implantable device shown in FIG. 1.

With particular reference to FIGS. 1 and 2, an example of device 10 includes a suburethral sling 100 with opposing ends 102 and 104. Device 10 also includes interconnecting member 110 having opposing ends 112 and 114, and interconnecting member 129 having opposing ends 130 and 134. End 112 of interconnecting member 110 is coupled to end 1502 of sling 100; and as shown in FIG. 2 end 130 of interconnecting member 129 is coupled to end 104 of sling 100. Although shown in the drawings via phantom lines as being coupled to an underside or bottom surface of sling 100, it is to be understood that the coupling of interconnecting members 110 and 129 to sling 100 may be provided at any suitable surface of sling 100 and at any suitable orientation thereon.

Also as shown in FIG. 2, in one embodiment device 10 includes a fixed anchor 136 having a body 122 with a proximal end and a distal end, and a channel 124 extending longitudinally therethrough. A plurality of flanges 126 protrude from the distal end, separated by webs 127. End 134 of interconnecting member 129 is fixedly coupled to body 122. Fixed anchor 136 also includes a collar 138. When assembled for use in device 10 as shown in FIG. 1, collar 138 covers the proximal end of body 122 of fixed anchor 136 and end 134 of interconnecting member 129 coupled to body 122.

Figure 3:
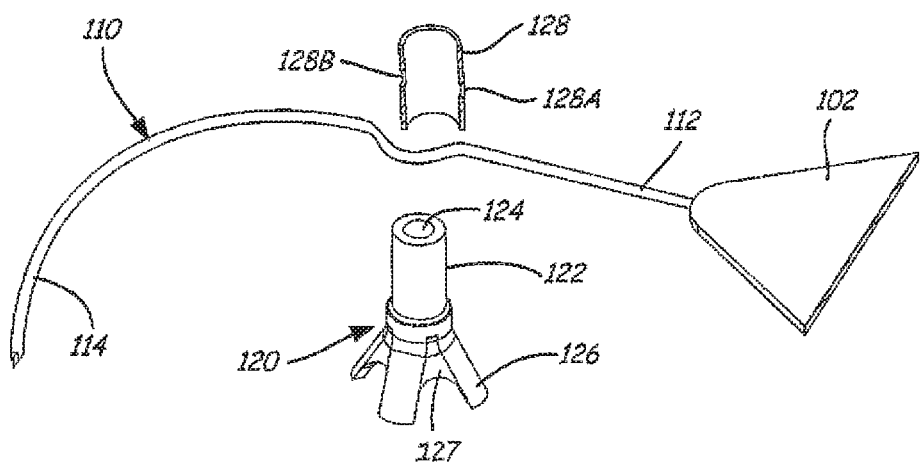
FIG. 3 is an exploded illustration of another component of the implantable device shown in FIG. 1.
Figure 4:
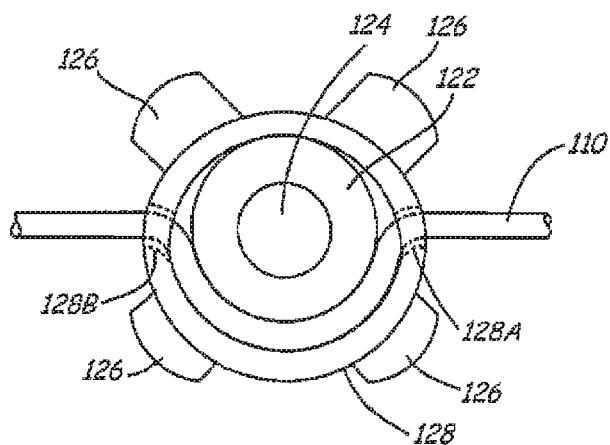
FIG. 4 is an assembled, top view of the component shown in FIG. 3.

Device 10 also includes an adjustable anchor 120. Referring to FIGS. 3 and 4, in one embodiment adjustable anchor 120 includes a body 122 having a proximal end and a distal end, with a channel 124 extending longitudinally therethrough and a plurality of flanges 126 protruding from the distal end that are in turn separated by webs 127. As shown in FIG. 3 in exploded half-section, and in a top assembly view in FIG. 4, adjustable anchor 120 has a collar 128 surrounding the proximal end that includes a pair of apertures 128A and 128B. When assembled for use in device 10, collar 128 covers body 122 of adjustable anchor 120 while apertures 128A-B in collar 128 permit passage of interconnecting member 110 therethrough in frictional sliding engagement with adjustable anchor 120. In this regard and with reference to FIG. 4, it is to be appreciated and understood that interconnecting member 110 is disposed through aperture 128A of collar 128, around a partial circumference of body 122, and through aperture 128B of collar 128. By virtue of an intentionally close fit to exert a compressive force and thus frictional interference between interconnecting member 110, collar 128, and body 122, adjustable anchor 120 is slidably coupled to interconnecting member 110 to permit bi-directional movement along interconnecting member 110 upon overcoming such frictional interference.

It is to be understood that an amount of compressive force and thus desired frictional interference could be varied among embodiments of adjustable anchor 120 with regard to an elasticity of a particular material chosen for collar 128 and also with regard to placement of apertures 128A and 128B in collar 128. For example, with locations of apertures 128A-B being constant, if a material chosen for collar 128 in a first embodiment of adjustable anchor 120 has less elasticity than a material chosen for collar 128 in a second embodiment of adjustable anchor 120, then the compressive force and resulting frictional interference of the first embodiment would be greater than that of the second embodiment due to, comparatively, greater resistance of collar 128 against interconnecting member 110 in the first embodiment than in the second embodiment. Similarly, with a material for collar 128 being constant, if apertures 128A-B are placed farther apart in one embodiment of anchor 120 than in a second embodiment of anchor 120, then the compressive force and resulting frictional interference of the first embodiment would be greater than that of the second embodiment due to, comparatively, a longer path through adjustable anchor 120 of interconnecting member 110 in the first embodiment than in the second embodiment.

Figure 5:
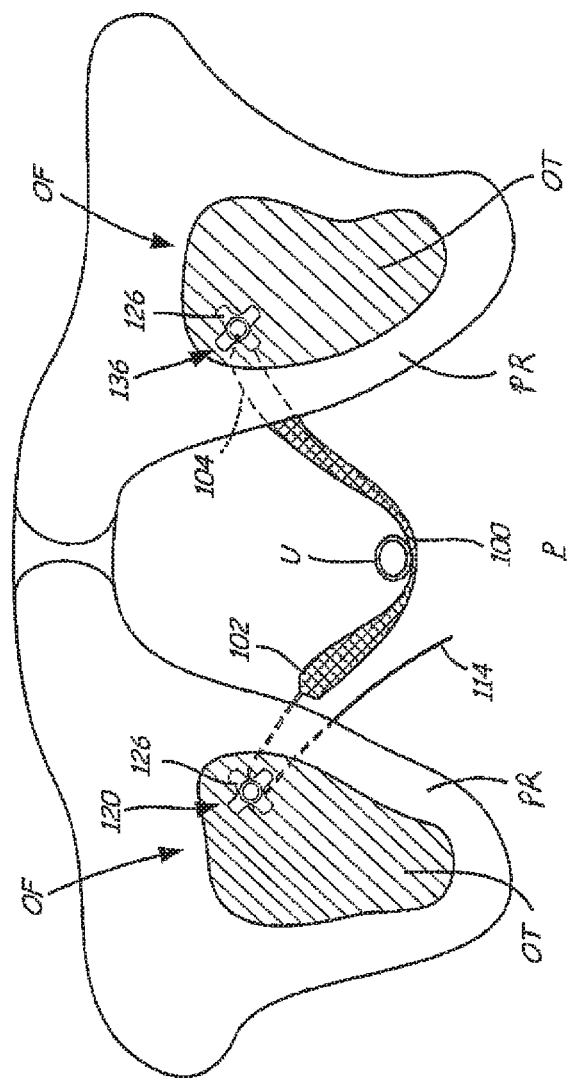
FIG. 5 is an illustration of the implantable device shown in FIG. 1, after implantation in a patient.

This feature of frictional sliding engagement between interconnecting member 110 and adjustable anchor 120 enables adjustment and tensioning of sling 100 when implanted in a patient. Referring to FIG. 5, one embodiment of device 10 is illustrated as having been implanted in a pelvic region P of a patient that includes urethra U and obturator tissue OT in each obturator foramen OF. In the drawing suburethral sling 100 of device 10 is shown as having been positioned under the patient's urethra U, with placement of fixed anchor 136 in obturator tissue OT of one obturator foramen OF and placement of adjustable anchor 120 in obturator tissue OT in the other obturator foramen OF. If desired, positions of anchors 120 and 136 could be exchanged in a left and right sense relative to pelvic region P. As will be further described, flanges 126 and webs 127 of anchors 120 and 136 secure the placement of each anchor in respective obturator tissue OT; and in one embodiment, at least one flange 126 has an angled or beveled edge 126E to promote such secure placement in obturator tissue OT or other anatomical tissue.

In one embodiment, at least one web 127 is self-creasing. Specifically, upon application of pressure to flange 126 such as when anchors 120 and 136 are being deployed through and secured at selected anatomical tissue, web 127 tends to fold or crease which thereby tends to facilitate, advantageously, a temporary bending or deflection of an adjacent flange 126 downwardly and inwardly toward longitudinal channel 124. In turn, this downward or inward bending or deflection of flange 126 tends to facilitate such deployment of the anchor through and into the tissue. Furthermore, upon such deployment through tissue, web 127 advantageously tends to inhibit an inverse bending or deflection of flange 126 upwardly toward body 122.

By way of the coupling of interconnecting members 110 and 129 to anchors 120 and 136 respectively, and the coupling of interconnecting members 110 and 129 to ends 102 and 104 of sling 100 respectively, sling 100 is maintained in position as desired under urethra U. With fixed anchor 136 and adjustable anchor 120 so implanted in obturator tissue OT, and with regard to the frictional sliding engagement between interconnecting member 110 and adjustable anchor 120, it is to be particularly understood that pulling on end 114 of interconnecting member 110 away from adjustable anchor 120 with a force sufficient to overcome the aforementioned interference force between interconnecting member 110 and adjustable anchor 120 would cause interconnecting member 110 to pass through anchor 120 with a resultant shortening of a distance between end 1502 of sling 100 and adjustable anchor 120. Thereby, sling 100 would be raised or elevated under urethra U as may be desired and as will be further described. Conversely, pulling on end 112 of interconnecting member 110 away from adjustable anchor 120 (or pulling on sling 100 away from anchor 120, or so pulling on both end 112 and sling 100) with such force would overcome the interference and cause interconnecting member 110 to pass in an opposite direction through anchor 120 with a resultant lengthening of a distance between end 1502 of sling 100 and adjustable anchor 120. Thereby, sling 100 would be lowered under urethra U as may be desired and as will be further described.

It is to be appreciated and understood that the novel construction and operation of device 10 is to be provided with respect to three force parameters. First, device 10 is to be constructed such that adjustable anchor 120 is not destroyed or otherwise damaged upon frictional sliding movement of interconnecting member 110 through anchor 120. Second, device 10 is to be constructed such that neither fixed anchor 136 nor, particularly, adjustable anchor 120 are pulled out or dislodged from obturator tissue OT into which they have been placed and secured, upon movement of interconnecting member 110 through adjustable anchor 120 during intraoperative adjustment. Third, device 10 is to be constructed such that the aforementioned interference force between interconnecting member 110 and adjustable anchor 120 is sufficiently high to inhibit movement of sling 100 under urethra U during a provocative event such as coughing by the patient when internal anatomical forces are exerted upon device 10.

In one embodiment, sling 100 has a length of about 7 cm (2.76 in.) and a width in a range of about of 8 mm (0.315 in.) to 11 mm (0.433 in.). Further, in one embodiment sling 100 is a medical grade material such as, for example, knitted polypropylene ARIS® brand mesh material that is commercially available from Coloplast A/S; and interconnecting members 110 and 129 are lengths of medical grade suture or suture-like materials as aforementioned. In another embodiment, interconnecting members 110 and 129 could be, for example, the aforementioned polypropylene material of sling 100 that has been knitted, woven, or otherwise formed into an elongated suture-like filamentary material. In another embodiment interconnecting members 110 and 129 could be, variously alone or together, continuations of the material of sling 100 configured to have characteristics of a suture-like filamentary material. Accordingly, such embodiments would provide a material having an overall width approximating that of a surgical suture.

Anchors 120 and 136 could be manufactured using any suitable materials such as polypropylene and polyurethane, and fabrication techniques such as molding and milling. In one embodiment, body 122, flanges 126, and webs 127 are fabricated from polypropylene. In one embodiment, collar 128 is molded from a thermoplastic polyurethane material or polymeric elastomer such as TECOTHANE® brand material. In one embodiment, anchors 120 and 136 have an overall length of 0.622 cm (0.245 in.) and a maximum width at flanges 126 of 0.470 cm (0.185 in.). In one embodiment, flanges 126 have a width of 0.114 cm (0.045 in.) and a thickness of 0.038 cm (0.015 in.). In one embodiment, webs 127 have a thickness of approximately one-half that of flanges 126, or about 0.019 cm (0.008 in.). In one embodiment, body 122 has a length of 0.312 cm (0.123 in.) and a diameter of 0.172 cm (0.068 in.). In one embodiment, longitudinal channel 124 in body 122 has a diameter of 0.097 cm (0.038 in.). In one embodiment, before being assembled as described below, collar 128 has an inner diameter of 0.127 cm (0.050 in.), an outer diameter of 0.254 cm (0.100 in.), and a length of 0.318 cm (0.125 in.); and apertures 128A-B have a diameter of 0.051 cm (0.020 in.). In one embodiment, collar 138 of anchor 136 has an inner diameter of 0.191 cm (0.075 in.), an outer diameter of 0.254 cm (0.100 in.), and a length of 0.254 cm (0.100 in.).

In one example of construction of device 10, with reference again to FIG. 2, end 112 of interconnecting member 110 is sonically welded to end 1502 of sling 100; and end 134 of interconnecting member 129 is sonically welded to end 104 of sling 100. Further in this example, end 134 of interconnecting member 129 is placed against body 122 of anchor 136, and collar 138 is placed over body 122 and end 134. Those assembled components are then sonically welded, thereby securing interconnecting member 129 to anchor 136.

Regarding assembly of adjustable anchor 120, in one embodiment collar 128 is swelled by using a suitable solvent such as methylethylketone (or MEK; also referred to as butanone). Collar 128, manufactured from the thermoplastic polyurethane material as aforementioned, is immersed in the MEK for approximately four hours whereupon it swells or becomes enlarged due to infiltration of the MEK into a molecular composition of the polyurethane material causing its expansion in all dimensions. Swelled collar 128 is then loosely placed over body 122 of adjustable anchor 120, and as aforementioned end 114 of interconnecting member 110 is then passed through aperture 128A of collar 128, around a partial circumference of body 122, and through aperture 128B such that a segment of interconnecting member 110 is within apertures 128A-B. In another embodiment interconnecting member 110 is placed through apertures 128A and 128B of swelled collar 128 such that a segment of interconnecting member 110 is within apertures 128A-B, and then collar 128 is placed over body 122 of adjustable anchor 120. That assembly is then raised to a temperature of 30 C for approximately 24 hours, to accelerate evaporation of the MEK from the thermoplastic polyurethane material. When the MEK evaporates, the swelling of collar 128 decreases, effectively returning collar 128 to its pre-swelled dimensions. Thereby, collar 128 tightly surrounds body 122 and interconnecting member 110 disposed therebetween. A result of such assembly is that interconnecting member 110 is movable through apertures 128A-B of collar 128, in frictional sliding contact between body 122 and an inside surface of collar 128.

Although a path through apertures 128A-B is illustrated as being perpendicular to longitudinal channel 124, one aperture 128A or 128B could be at a higher or lower point on collar 128 than the other aperture and thus the path through apertures 128A-B could be at another angle relative to channel 124.

Also, it is to be understood that the aforedescribed connections of components by sonic welding could instead be accomplished by any other suitable means such as, for example, by use of a suitable adhesive material.

In another embodiment, anchor 136 could be coupled directly to anatomical support member 100. In such an embodiment, interconnecting member 129 could be omitted and end 104 could be, for example, sonically welded, glued, or otherwise mechanically coupled to anchor 136 between an outside surface of body 122 and an inside surface of collar 128. In another embodiment, collar 128 could be omitted with, simply, connection of end 104 to body 122.

Figure 6:
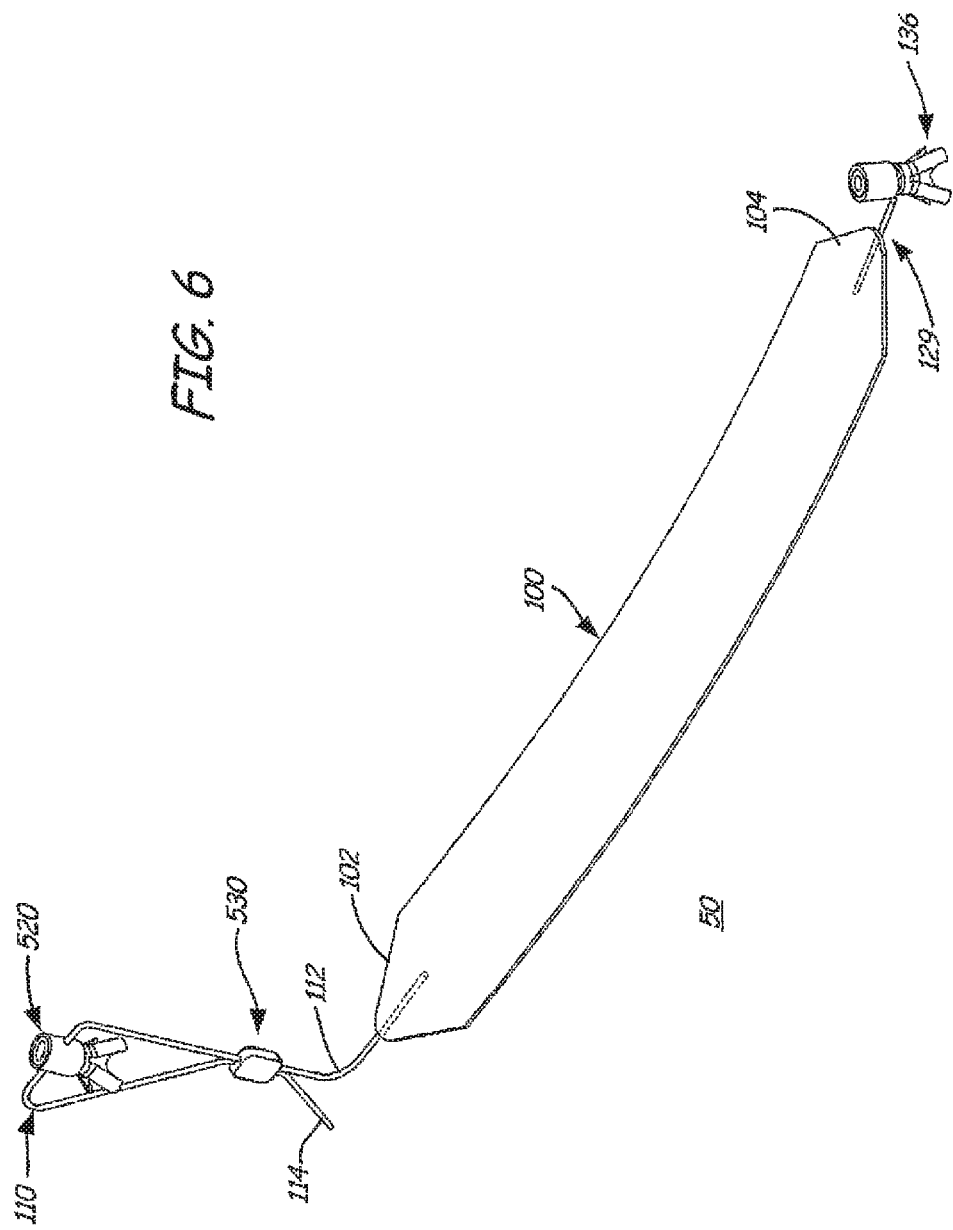
FIG. 6 is an illustration of another embodiment of an implantable device for anatomical support.

Illustrated in FIG. 6 is another example of an implantable device for anatomical support (device 50). In the drawings, like reference numerals denote like components among embodiments. Example device 50 includes an anatomical support member as a suburethral sling 100 with ends 102 and 104; interconnecting member 110 with ends 112 and 114; and interconnecting member 129 with ends 130 and 134. End 112 of interconnecting member 110 is coupled to end 1502 of sling 100; and end 130 of interconnecting member 129 is fixedly coupled to end 104 of sling 100. Although shown in the drawings via phantom lines as being coupled to an underside or bottom surface of sling 100, it is to be understood that the coupling of interconnecting members 110 and 129 to sling 100 may be provided at any suitable surface of sling 100 and at any suitable orientation thereon.

Fixed anchor 136 includes a body 122 having a proximal end and a distal end, with a longitudinal channel 124 extending therethrough. A plurality of flanges 126 protruding from the distal end of body 122, separated by webs 127. End 134 of interconnecting member 129 is fixedly coupled to body 122 of fixed anchor 136; and fixed anchor 136 includes a collar 138. Collar 138 covers the proximal end of body 122 and end 134 of interconnecting member 129 coupled to body 122.

Figure 7:
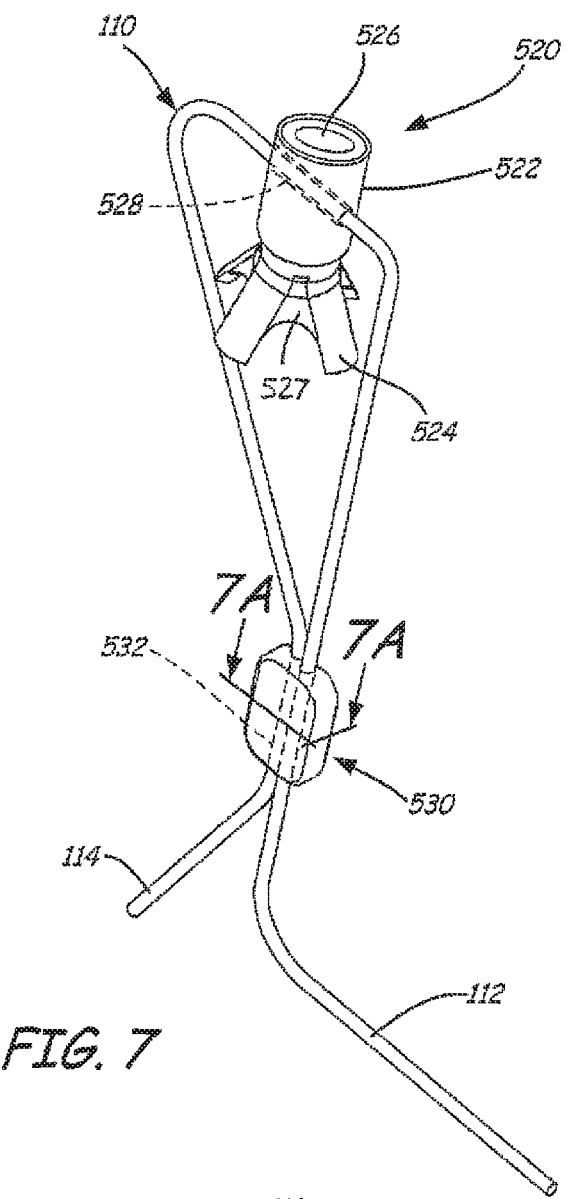
FIG. 7 is a magnified illustration of components of the implantable device shown in FIG. 6.

Referring to FIGS. 7, 8 and 8A, device 50 also includes an anchor 520 and a separate tensioning element 530 slidably coupled to interconnecting member 110. In one embodiment, anchor 520 includes a body 522 having a channel 526 extending longitudinally therethrough, and a plurality of flanges 524 protruding therefrom separated by webs 527; and in one embodiment, at least one flange 524 has an angled or beveled edge 524E to promote secure placement in obturator tissue OT or other anatomical tissue.

In one embodiment, at least one web 527 is self-creasing. Specifically, upon application of pressure to flange 524 such as when anchor 520 is being deployed through and secured at selected anatomical tissue, web 527 tends to fold or crease which thereby tends to facilitate, advantageously, a temporary bending or deflection of an adjacent flange 524 downwardly and inwardly toward longitudinal channel 526. In turn, this downward or inward bending or deflection of flange 524 tends to facilitate such deployment of the anchor through and into the tissue. Furthermore, upon such deployment through tissue, web 527 advantageously tends to inhibit an inverse bending or deflection of flange 524 upwardly toward body 522.

Figure 7A:
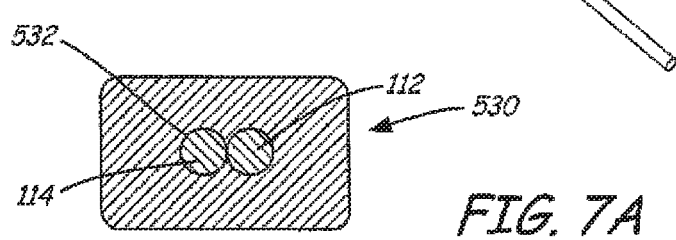
FIG. 7A is a cross-sectional view of components shown in FIG. 7, taken along lines 7A-7A.

Anchor 520 also has a channel 528 through body 522 to permit interconnecting member 110 to move therethrough in freely sliding engagement with anchor 520. In this example of device 50, and referring to FIGS. 6, 7, and 7A, interconnecting member 110 is partially disposed within tensioning element 530. In one embodiment, tensioning element 530 is fabricated from a suitable biocompatible material such as, e.g., silicone or a low durometer thermoplastic material like polyurethane. In assembly of device 50, ends 112 and 114 of interconnecting member 110 are disposed within tensioning element 530 (indicated by paths 532 in FIG. 7). In particular, although not illustrated, it is to be understood that in one embodiment end 114 of interconnecting member 110 is driven through tensioning element 530 by use of, e.g., a needle. End 114 is then placed through channel 528 of anchor 520 and then driven by the needle back through tensioning element 530. As shown in FIG. 7A, by virtue of exertion of a compressive force and thus frictional interference between tensioning element 530 and interconnecting member 110, tensioning element 530 is slidably coupled to interconnecting member 110 to permit bi-directional movement along interconnecting member 110 upon overcoming such frictional interference. This feature of sliding frictional interference between interconnecting member 110 and tensioning element 530 permits adjustment and tensioning of sling 100 when implanted in a patient. With reference to FIG. 5, it is to be understood that device 50 could be substituted for device 10 and implanted in a pelvic region P of a patient that includes urethra U and obturator tissue OT in each obturator foramen OF. Thus, suburethral sling 100 of device 50 could be positioned under the patient's urethra U, with secure placement of fixed anchor 136 in obturator tissue OT of one obturator foramen OF and by secure placement of anchor 520 in obturator tissue OT in the other obturator foramen OF. Positions of anchors 520 and 136 could be exchanged in a left and right sense relative to pelvic region P. By grasping tensioning element 530 and pulling on end 114 away from tensioning element 530 with a force sufficient to overcome the aforementioned frictional interference force between interconnecting member 110 and tensioning element 530, interconnecting member 110 slides through tensioning element 530 and thus through anchor 520 with a resultant shortening of a distance between end 1502 of sling 100 and tensioning element 530. Thereby, sling 100 would be raised or elevated under urethra U. Conversely, grasping tensioning element 530 and pulling on end 112 of interconnecting member 110 away from tensioning element 530 (or pulling on sling 100 away from tensioning element 530, or so pulling on both end 112 and sling 100) with such force would overcome the interference and cause interconnecting member 110 to pass through tensioning element 530 and thus in an opposite direction through tensioning element 530 with a resultant lengthening of a distance between end 1502 of sling 100 and tensioning element 530. Thereby, sling 100 would be lowered under urethra U.

Like device 10, it is to be appreciated and understood that the novel construction and operation of device 50 is to be provided with respect to three force parameters. First, device 50 is to be constructed such that tensioning element 530 is not destroyed or otherwise damaged upon frictional sliding movement of interconnecting member 110 through it. Second, device 50 is to be constructed such that neither anchor 136 nor anchor 520 are pulled out or dislodged from obturator tissue OT into which they have been placed and secured, upon of movement of interconnecting member 110 through tensioning element 530 during intraoperative adjustment. Third, device 50 is to be constructed such that the aforementioned interference force between interconnecting member 110 and tensioning element 530 is sufficiently high to inhibit movement of sling 100 under urethra U during a provocative event when the patient's internal anatomical structures or tissues exert forces upon device 50.

In one embodiment of device 50, components of anchor 520 could be constructed in dimensions, and from materials and techniques, as variously described regarding similar components of fixed anchor 136 in device 10. Furthermore, components of one embodiment of device 50 could be coupled and secured as described relative to similar components of device 10.

Another embodiment of anchor 520 is depicted in FIGS. 9 and 9A wherein channel 526 is a generally semi-circular or "D" shape. D-shaped channel 526, extending longitudinally through body 522, could provide more clearance for channel 528 compared to the longitudinal and fully cylindrical channel 526 shown in FIGS. 7, 8 and 8A. Furthermore, and although not illustrated, longitudinal channel 526 could also be provided in a smaller diameter than as shown in FIGS. 8A and 9A to thereby provide even greater clearance for channel 528. A path through channel 528 is illustrated as being perpendicular to longitudinal channel 526; but in another embodiment, the path could be at another angle relative to channel 526.

It is to be appreciated that when implanted in a patient, sling 100 of devices 10 and 50 advantageously extends nearly from obturator tissue OT on one side of the patient to obturator tissue OT on an opposite side of the patient as a result of, e.g., an intentionally short segment of interconnecting member 129 that couples end 104 of sling 100 to fixed anchor 136 and a selected length of sling 100 with respect to a typical distance between opposing obturator foramen OF.

Referring to FIG. 10A, and with additional reference to FIGS. 1, 3, and 4, it is to be appreciated that the novel adjustable anchor 120 described herein could be useful for secure placement of virtually any anatomical support member (A) coupled to an interconnecting member 110 where it is desired to provide adjustment or tensioning of the support member when implanted in a patient. Anatomical support member (A) could be, for example, a shaped mesh material for treatment of prolapse. Also, an anatomical support member could employ any number of adjustable anchors 120, with or without any number of fixed anchors 136.

Referring to FIGS. 10B and 10C, it is to be also appreciated that the novel adjustable anchor 120 described herein could be useful with an implantable device (S) for treatment of urinary incontinence where it is desired to provide adjustment or tensioning of device (S) when implanted in a patient. Although not specifically depicted in FIGS. 10B-C, it is to be understood however that device (S) could employ any number of adjustable anchors 120, with or without any number of fixed anchors 136.

Although not illustrated in FIGS. 10A-C, it is to be understood that anchor 520 with tensioning element 530 could be utilized with any anatomical support member (A); and any number of combinations of anchor 520 with tensioning element 530 could also be utilized with or without any number of fixed anchors 136.

Regardless of a particular embodiment of adjustable anchor 120, or of anchor 520 with tensioning element 530, it is to be understood and appreciated that such novel anchors described herein may be relatively small when compared to known anatomical anchors. This advantage results from the fact that the novel anchors described herein are coupled to anatomical support members by sutures or suture-like filaments, rather than directly to the anatomical support members themselves which are usually larger and wider than sutures or suture-like filaments as in some known anatomical anchors. In alternative embodiments, any of the anchors (e.g., anchors 120, 136, or 520) would include at least one flange 126.

Figure 11:
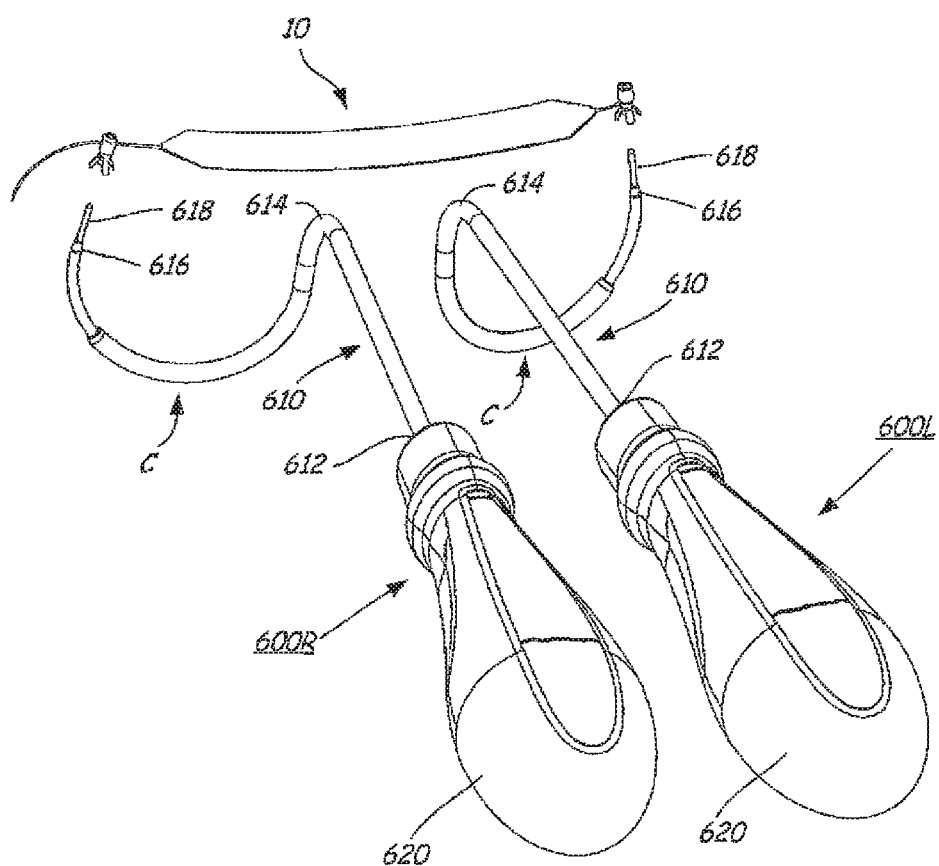
FIG. 11 is an illustration of one embodiment of a pair of tools for use in a surgical method to place an anatomical support member in a patient.
Figure 12:
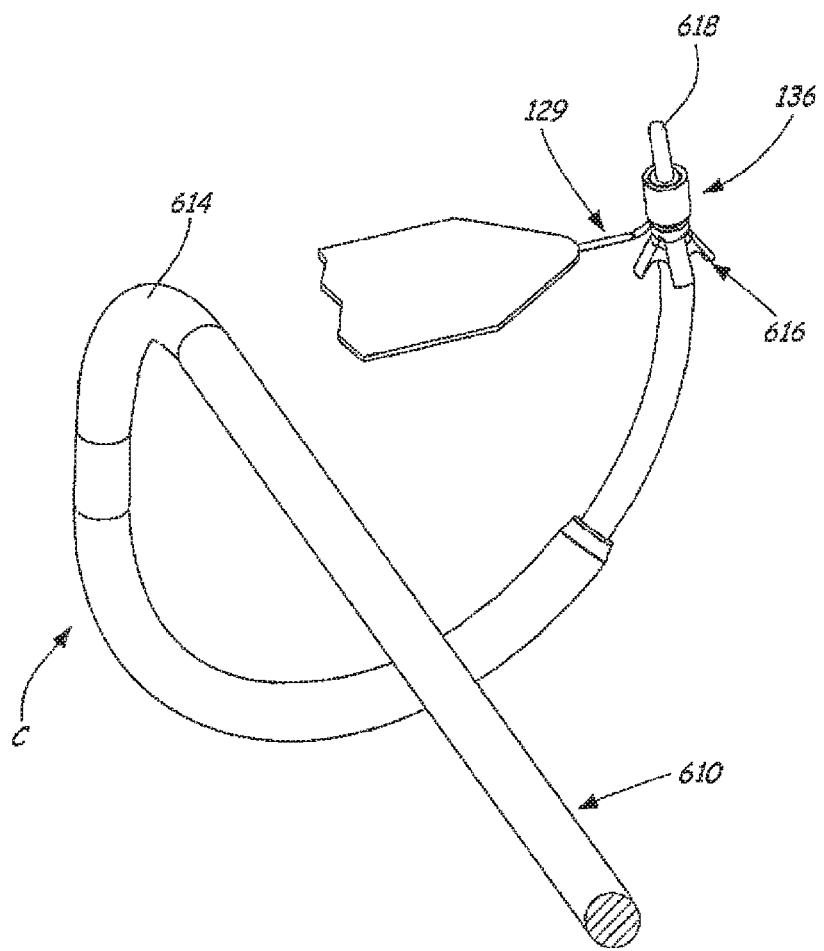
FIG. 12 is a magnified, partial illustration of one of the tools shown in FIG. 11, coupled to a component shown in FIG. 1.

FIGS. 11 and 12 illustrate an example of a tool for use in placing an implantable device for anatomical support in a patient, such as sling 100 of FIG. 1. In the drawing, a pair of tools 600R and 600L are illustrated, in left hand and right hand embodiments—with such designations referring to a patient's left and right sides, respectively. It is to be understood that the tools are identical except for a direction of a helical curve C as described below.

In this example, tools 600R and 600L each include a shaft 610 having a proximal end 612 and a cylindrical distal tip 618. A handle 620 is coupled to proximal end 612 of shaft 610. Handle 620 could have any desired shape or configuration with respect to ergonomic and other considerations of interest. A generally helical curve C is provided in shaft 610. Helical curve C terminates in a shoulder 616 proximate to distal tip 618. In use as described below, helical curve C is advantageously configured to guide tip 618 from an incision (e.g., a vaginal incision in a female patient or a perineal incision in a male patient), around a descending ramus, and through an obturator foramen OF in the patient. In this example, and as shown in FIG. 12, cylindrical distal tip 618 is configured to be placed through cylindrical channels 124 of adjustable anchor 120 and fixed anchor 136 (as shown in, e.g., in FIGS. 2 and 3), and through cylindrical channel 526 of anchor 520 (as shown, e.g., in FIGS. 7, 8, and 8A). When so placed, shoulder 616 abuts the anchor's body adjacent to the flanges with the anchor being thereby carried on tip 618 of tool 600R or 600L. Although not illustrated, it is to be understood that if an anchor was constructed with a semicircular or "D" shaped channel 526 as depicted in FIGS. 9 and 9A, tip 618 would then be a complementary semicircular or "D" shaped configuration.

In one embodiment, handle 620 has a length of 11.43 cm (4.5 in.). A length of shaft 610, from handle 620 to a beginning point 614 of curve C is 17.78 cm (7.0 in.). Shaft 610 has a diameter of 3 mm (0.12 in.) decreasing to 1 mm (0.04 in.) at shoulder portion 616. Curve C has a radius of curvature in a range of 2.03 cm (0.80 in.) to 2.54 cm (1.0 in.). Suitable materials for construction of handle 620 include, for example, a medical grade thermoplastic or thermoset material, preferably having both high and low durometer regions for ergonomic considerations. A suitable material for construction of shaft 610 is, for example, medical grade stainless steel. Furthermore, the tool described herein—such as the examples of tools 600R and 600L—could be disposable or sterilizable and reusable.

It is to be appreciated that in one embodiment, as shown particularly in FIG. 12, a length of distal tip 618 is chosen so that it protrudes from an anchor seated on shoulder 616. When constructed from stainless steel as aforementioned, relatively stiff tip 618 is thereby configured to pierce anatomical tissue when in use as described below. Thereby, the anchor itself does not need to include such a tissue-penetrating tip.

Referring in particular to FIGS. 1, 5, 11, and 12, an example of a surgical method to implant a device for anatomical support 10, in a form of suburethral sling 100 for treatment of urinary incontinence in a female patient, is as follows.

A catheter is placed in the patient's urethra U, among other usual and preliminary steps in preparation for surgery. The patient is placed on an operating table in a slightly exaggerated lithotomy position with buttocks extending just beyond an edge of the table. With the patient under anesthesia, a vaginal incision and blunt dissection are made. In one embodiment of the method, a fixed anchor is first placed in obturator tissue OT on the patient's left side, followed by placement of an adjustable anchor in obturator tissue OT on the patient's right side. Accordingly in this embodiment, fixed anchor 136 is placed on distal tip 618 of left hand tool 600L having an orientation of helical curve C corresponding to the patient's left side. Tip 618 of left hand tool 600L, with fixed anchor 136 seated thereupon, is placed within the vaginal incision. Left hand tool 600L is then rotated such that rotation of helical curve C advances tip 618 and fixed anchor 136 in a path around a descending pubic ramus (PR) on the patient's left side, continuing in that path until fixed anchor 136 penetrates obturator tissue OT on the patient's left side (as may be indicated by an audible or tactile "pop") and is thus secured therein. By virtue of flanges 126, fixed anchor 136 is inhibited from being pulled back through obturator tissue OT so penetrated as shown in FIG. 5. Left hand tool 600L is then removed from the patient. Next in this embodiment, adjustable anchor 120 is placed on distal tip 618 of right hand tool 600R having an orientation of helical curve C corresponding to the patient's right side. Tip 618 of right hand tool 600R, with adjustable anchor 120 seated thereupon, is placed within the vaginal incision. Right hand tool 600R is then rotated such that rotation of helical curve C advances tip 618 and adjustable anchor 120 in a path around a descending pubic ramus (PR) on the patient's right side, continuing in that path until adjustable anchor 120 penetrates obturator tissue OT on the patient's right side (as may be indicated by an audible or tactile "pop") and is thus secured therein. By virtue of flanges 126, adjustable anchor 120 is inhibited from being pulled back through obturator tissue OT so penetrated as shown in FIG. 5. Right hand tool 600R is then removed from the patient.

With suburethral sling 100 thus placed and secured in the patient by way of fixed anchor 136 and adjustable anchor 120, an assessment is made of whether sling 100 is unacceptably loose or tight under urethra U. If sling 100 is unacceptably loose, then end 114 of interconnecting member 110 is pulled away from adjustable anchor 120 with a force sufficient to overcome the aforementioned interference force between interconnecting member 110 and adjustable anchor 120. Interconnecting member 110 thus passes through anchor 120 with a resultant shortening of a distance between end 1502 of sling 100 and adjustable anchor 120. Thereby sling 100 is raised or elevated under urethra U as desired. Conversely, if sling 100 is unacceptably tight, then end 112 of interconnecting member 110 is pulled away from adjustable anchor 120 (or sling 100 is pulled away from adjustable anchor 120, or both end 112 and sling 100 are so pulled) with a force sufficient to overcome the interference force between interconnecting member 110 and adjustable anchor 120. Interconnecting member 110 thus passes through anchor 120 with a resultant lengthening of a distance between end 1502 of sling 100 and adjustable anchor 120. Thereby sling 100 is lowered under urethra U as desired. These steps of shortening and lengthening a distance between end 1502 of sling 100 and adjustable anchor 120 may be repeated in any order and as frequently as necessary to provide optimal suburethral support from sling 100 to urethra U. The vaginal incision is then closed and usual post-operative procedures are performed.

In another embodiment, the aforedescribed method could employ an example of device 50 as shown in FIGS. 6-8A. In this embodiment of the method, a catheter is placed in the patient's urethra U and the aforementioned preliminary steps in preparation for surgery are performed. The patient is placed in a slightly exaggerated lithotomy position with buttocks extending just beyond an edge of an operating table; and under anesthesia, a vaginal incision and blunt dissection are made in the patient. In one embodiment of this method using device 50, a fixed anchor is first placed in obturator tissue OT on the patient's left side, followed by placement of an anchor in obturator tissue OT on the patient's right side that is associated with a separate tensioning element. Accordingly, fixed anchor 136 is placed on distal tip 618 of left hand tool 600L having an orientation of helical curve C corresponding to the patient's left side. Tip 618 of left hand tool 600L, with fixed anchor 136 seated thereupon, is placed within the vaginal incision. Left hand tool 600L is then rotated such that rotation of helical curve C advances tip 618 and fixed anchor 136 in a path around a descending pubic ramus (PR) on the patient's left side, continuing in that path until fixed anchor 136 penetrates obturator tissue OT on the patient's left side (as may be indicated by an audible or tactile "pop") and is thus secured therein. By virtue of flanges 126, fixed anchor 136 is inhibited from being pulled back through obturator tissue OT so penetrated as shown in FIG. 5. Left hand tool 600L is then removed from the patient. Next in this embodiment using device 50, anchor 520 is placed on distal tip 618 of right hand tool 600R having an orientation of helical curve C corresponding to the patient's right side. Tip 618 of right hand tool 600R, with anchor 520 seated thereupon, is placed within the vaginal incision. Right hand tool 600R is then rotated such that rotation of helical curve C advances tip 618 and anchor 520 in a path around a descending pubic ramus (PR) on the patient's right side, continuing in that path until anchor 520 penetrates obturator tissue OT on the patient's right side (as may be indicated by an audible or tactile "pop") and is thus secured therein. By virtue of flanges 126, anchor 520 is inhibited from being pulled back through obturator tissue OT so penetrated. Right hand tool 600R is then removed from the patient.

With suburethral sling 100 of device 50 thus placed and secured in the patient by way of fixed anchor 136 and anchor 520, an assessment is made of whether sling 100 is unacceptably loose or tight under urethra U. If sling 100 is unacceptably loose, then tensioning element 530 is grasped and end 114 of interconnecting member 110 is pulled away from tensioning element 530 with a force sufficient to overcome the aforementioned interference force between interconnecting member 110 and tensioning element 530. Interconnecting member 110 thus passes through anchor 520 with a resultant shortening of a distance between end 1502 of sling 100 and tensioning element 530. Thereby sling 100 is raised or elevated under urethra U as desired. Conversely, if sling 100 is unacceptably tight, then tensioning element 530 is grasped and end 112 of interconnecting member 110 is pulled away from tensioning element 530 (or sling 100 is pulled away from tensioning element 530, or both end 112 and sling 100 are so pulled) with a force sufficient to overcome the interference force between interconnecting member 110 and tensioning element 530. Interconnecting member 110 thus passes through anchor 120 with a resultant lengthening of a distance between end 1502 of sling 100 and tensioning element 530. Thereby sling 100 is lowered under urethra U as desired. Similarly to device 10, these steps of shortening and lengthening a distance between end 1502 of sling 100 and tensioning element 530 in device 50 may be repeated in any order and as frequently as necessary to provide optimal suburethral support from sling 100 to urethra U. The vaginal incision is then closed and usual post-operative procedures are performed.

The adjustable anchor 120 and/or the fixed anchor 136 are each suited for attachment to support devices having a variety of shapes, including the rectangular shapes described and illustrated above, non-rectangular shapes described and illustrated below, or other symmetrical or non-symmetrical shapes as appropriate for providing anatomical support.

Figure 13:
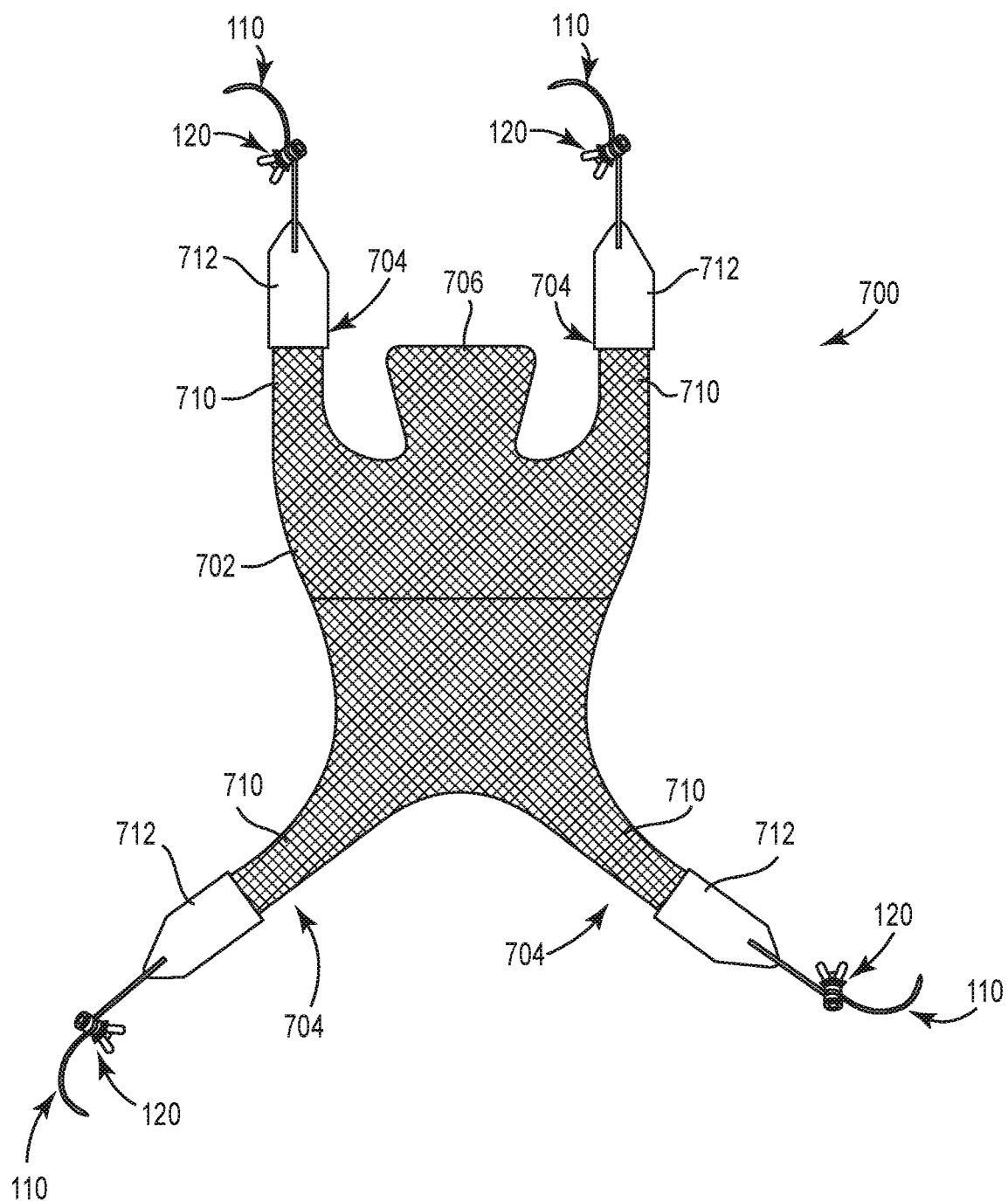
FIG. 13 is a top view of one embodiment of an implantable anatomical support device.

FIG. 13 is a top view of one embodiment of an implantable anatomical support 700 device. The implantable anatomical support 700 includes a support body 702 with at least three arms 704 extending from the support body 702, an interconnecting member 110 that is coupled to each of the arms 704 extending from the support body 702, and an adjustable anchor 120 slidably coupled to each of at least two of the interconnecting members 110.

The adjustable anchors 120 are configured for bi-directional movement along the interconnecting member 110 and exert a compressive force generating frictional interference between the adjustable anchor 120 and the interconnecting member 110. The frictional interference between the adjustable anchor 120 and the interconnecting member 110 inhibits the bi-directional movement of the adjustable anchor 120 along the interconnecting member 110 unless sufficient force is applied to overcome the frictional interference.

The arms 704 in combination with the interconnecting members 110 and the adjustable anchors 120 allow the anatomical support 700 to be implanted in a body and adjusted into a desired tensioned position. The interconnecting members 110 and the adjustable anchors 120 obviate the use of multiple skin exit punctures, and eliminate the use of retriever components and sleeves around the arms 704 that are at times employed with support bodies having arms.

The support body 702 is non-rectangular and the support 700 includes four arms 704 extending from the non-rectangular support body 702. In one embodiment, the support body 702 has a curved outside perimeter with bilateral symmetry relative to a central longitudinal axis of the non-rectangular support body 702. In one embodiment, the support body 702 has four arms 704 and includes a central tail 706 located between two of the arms 704. The central tail is configured for attachment to a suitable pelvic landmark, such as a ligament or other tissue. In one embodiment, the support body 702 is fabricated from a porous mesh configured to be compatible with biological in-situ tissue ingrowth.

In one embodiment, the arms 704 include a first arm segment 710 extending from support body 702 and a second arm segment 712 extending from the first arm segment 710, where the interconnecting members 110 extend from the second arm segment 712.

In one embodiment, the second arm segment 712 is the removed end portion 1504 of the sling 100 described above and is attached to body 702. In one embodiment, the second arm segment 712 is fabricated from the knitted polypropylene material described above and is attached to the first arm segment 710 and the support body 702. In one embodiment, the first arm segment 710 is fabricated from a different material than the second arm segment 712. Suitable attachment methods for attaching the second arm segment 712 to the first arm segment 710 include adhesive attachment, mechanical attachment devices such as clips, and energetic attachments such as sonic or ultrasonic welds, as examples.

In one embodiment, the first arm segment 710 is fabricated from the same material as the second arm segment 712. For example, each of the first arm segment 710 and the second arm segment 712 is fabricated from knitted polypropylene ARIS® brand mesh material that is commercially available from Coloplast A/S.

In one embodiment, the first arm segments 710 extend 1 cm or more from the support body 702. In one embodiment, one or more of the first arm segments 710 is provided as a "stubby" arm segment that extends from the support body 702 by less than 1 cm, for example. The second arm segment 712 extends from the first arm segment 710 (whether of the "stubby" format or not). The interconnecting member 110 is attached to the second arm segment 712, and one or the other of the adjustable anchor 120 or the fixed anchor 136 is attached to the interconnecting member 110.

In one embodiment, an interconnecting member 110 is attached to each arm 704 and an adjustable anchor 120 is attached to each interconnecting member 110. In one embodiment, an interconnecting member 110 is attached to each arm 704 and a fixed anchor 136 (FIG. 1) is attached to at least one of the interconnecting members 110. It will be recognized that the implantable anatomical support 700 could include one or more adjustable anchors with anywhere from zero to one or more fixed anchors. It is to be appreciated, then, that the device 700 could employ any number of adjustable anchors 120, with or without any number of fixed anchors 136.

Figure 14:
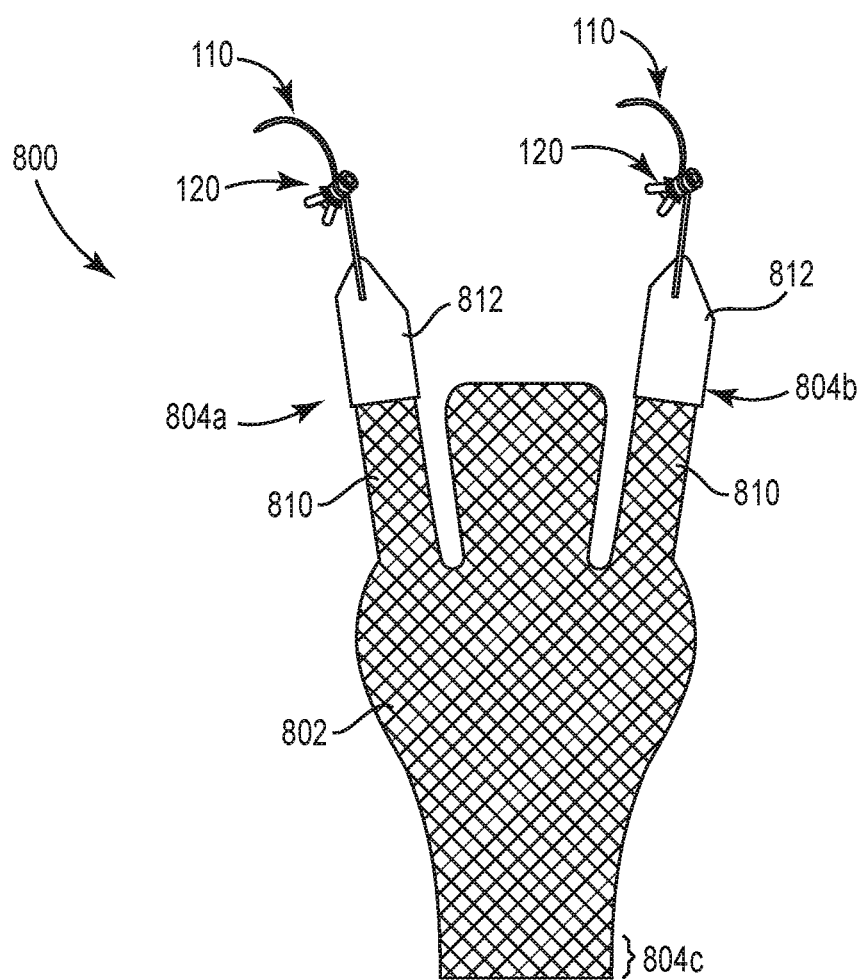
FIG. 14 is a top view of one embodiment of an implantable anatomical support device.

FIG. 14 is a top view of one embodiment of an implantable anatomical support 800. The implantable anatomical support 800 includes a support body 802 with at least three arms 804 extending from the support body 802, an interconnecting member 110 that is coupled to the arms 804 extending from the support body 802, and an adjustable anchor 120 slidably coupled to each of at least two of the interconnecting members 110.

The adjustable anchors 120 are configured for bi-directional movement along the interconnecting member 110 and exert a compressive force generating frictional interference between the adjustable anchor 120 and the interconnecting member 110. The frictional interference between the adjustable anchor 120 and the interconnecting member 110 inhibits the bi-directional movement of the adjustable anchor 120 along the interconnecting member 110 unless sufficient force is applied to overcome the frictional interference.

The arms 804 in combination with the interconnecting members 110 and the adjustable anchors 120 allow the anatomical support 800 to be implanted in a body and adjusted into a desired tensioned position. The interconnecting members 110 and the adjustable anchors 120 obviate the use of multiple skin exit puncture, and eliminate the use of retriever components and sleeves around the arms 804 that are at times employed with support bodies having arms.

The support body 802 is non-rectangular and the support 800 includes two arms 804a, 804b extending from one side of the non-rectangular support body 802 and a third arm 804c that is provided opposite the two arms 804a, 804b. In one embodiment, the support body 802 has a curved outside perimeter with bilateral symmetry relative to a central longitudinal axis of the non-rectangular support body 802. In one embodiment, the support body 802 has three arms 804, with an interconnecting member 110 attached to one each of the two arms 804a, 804b with the third arm 804c configured for direct attachment to body tissue, for example via sutures. In one embodiment, the support body 802 is fabricated from a porous mesh configured to be compatible with biological in-situ tissue ingrowth.

In one embodiment, the arms 804a, 804b are provided with a first arm segment 810 extending from support body 802 and a second arm segment 812 extending from the first arm segment 810, where the interconnecting members 110 extend from the second arm segment 812.

Figure 15:
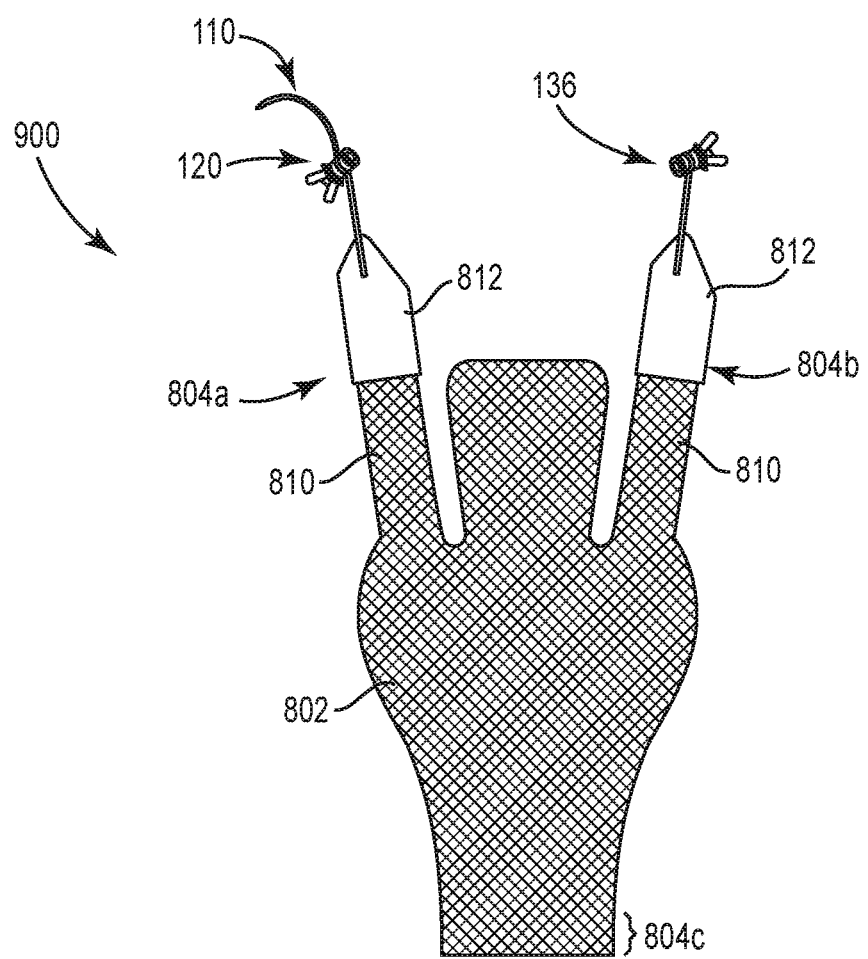
FIG. 15 is a top view of one embodiment of an implantable anatomical support device.

FIG. 15 is a top view of one embodiment of an implantable anatomical support 900. The implantable anatomical support 900 is similar to the implantable anatomical support 800 and includes the support body 802 with the arms 804 extending from the support body 802, with one adjustable anchor 120 slidably coupled to one interconnecting member 110 and a fixed anchor 136 connected to another interconnecting members 110. During implantation, the surgeon selectively attaches the fixed anchor 136 to appropriately identified tissue, attaches the adjustable anchor to adjacent tissue, and adjusts the adjustable anchor 120 along the interconnection member 110 to suitably adjust the tension in the support 900.

Although not illustrated in FIGS. 13-14, it is to be understood that anchor 520 with tensioning element 530 (FIG. 6) could be utilized with anatomical support 700 and any number of combinations of anchor 520 with tensioning element 530 could also be utilized with or without any number of fixed anchors 136.

It is to be understood that the features of the various exemplary embodiments described herein may be combined with each other, unless specifically noted otherwise.

FIG. 16 is a top view of one embodiment of a system 1000 configured to address pelvic dysfunction in a patient. Pelvic dysfunction includes male urinary incontinence, female urinary incontinence, or female pelvic organ prolapse.

In one embodiment, the system 1000 is configured to address male urinary incontinence and includes a support member 1002 and a tool 1004 configured to couple with the anchors 120, 136 to implant the support member 1002 into the patient, for example via a single incision.

In one embodiment, the support member 1002 includes a body portion 1010, and opposing trans obturator arms 1012 and suprapubic arms 1014 extending from the body portion 1010. In one embodiment, the fixed anchor 136 is attached to one of the trans obturator arms 1012 by the interconnecting member 129 and the adjustable anchor 120 is attached to the opposing one of the obturator arms 1012 by the interconnecting member 110.

As described below, the tool 1004 is employed to attach/anchor the anchors 120, 136 into membrane material of the obturator foramen such that the obturator arms 1012 extend between the opposing obturator membranes. The suprapubic arms 1014 are surgically placed suprapubically (with or without a tool).

In one embodiment, the anchor 120 is an adjustable anchor as described above and the support member 1002 includes four arms that are configured for four-point attachment to the patient to provide an adjustable support offering elevation and compression of the ventral urethral bulb of a man with compression of the perineal urethra. The support member 1002, as implanted, is configured to provide immediate beneficial relief to urinary incontinence and is also configured to allow tissue to grow into the porous structure of the support member 1002.

Figure 17:
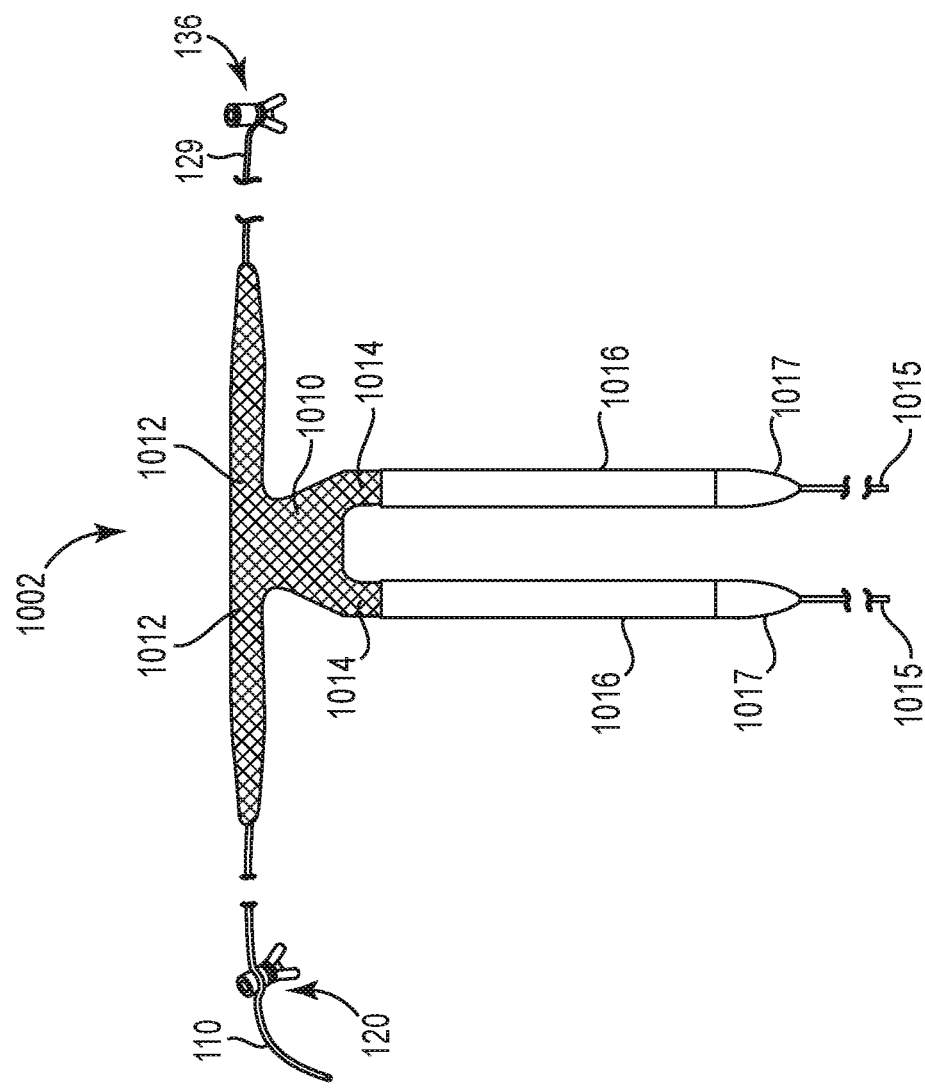
FIG. 17 is a top view of the adjustable support member illustrated in FIG. 16.

FIG. 17 is a top view of the support member 1002 modified to include optional suture lines 1015 connected to a removable tip 1017 at an end of each of the suprapubic arms 1014 and optional sleeves 1016 disposed over the arms 1014. The optional suture lines 1015 and sleeves 1016 are employed when placing the arms 1014 suprapubically within the patient with the tool 1004.

In general, the trans obturator arms 1012 are provided as a pair of opposing and aligned arms and the suprapubic arms 1014 are not parallel with the trans obturator arms 1012. Other conformations for support member 1002 are also acceptable, including more than four arms or fewer than four arms, and the relative orientation between the arms provided in the examples is not intended to limit the scope of this application.

In one embodiment, the support member 1002 is fabricated from a porous polypropylene mesh suited to allow tissue to grow into the mesh. In one embodiment, the support member 1002 includes optional sleeves 1016 disposed over the suprapubic arms 1014, for example, where the sleeves 1016 reduce friction of the arms 1014 as they are implanted within tissue of the patient. In one embodiment, the optional suture lines 1015 are braided polyester lines that are coated with a friction-reducing agent such as polytetrafluoroethylene, although other forms of suture lines and other forms of friction-reducing agents are also acceptable.

Figures 18A, 18B:
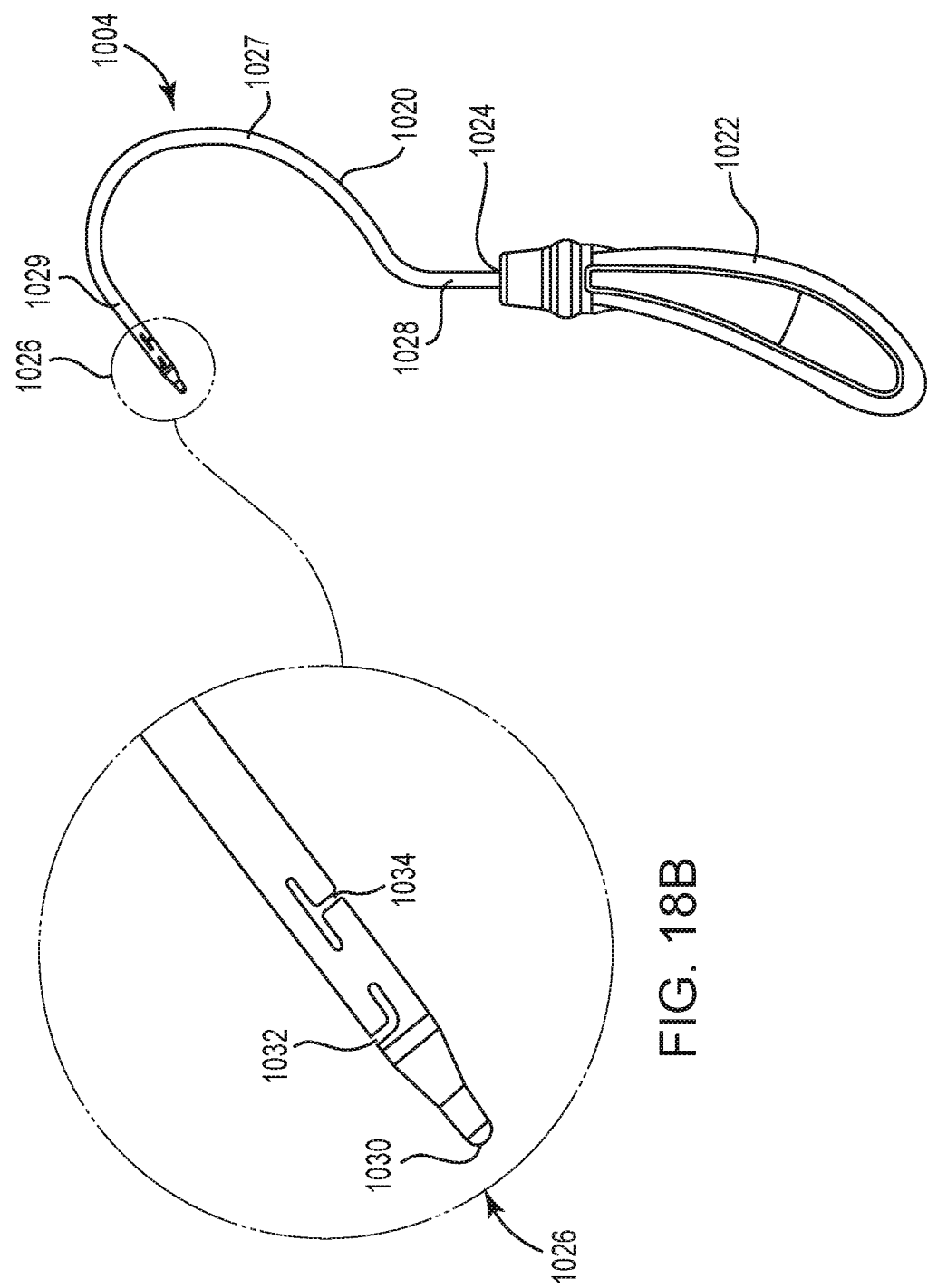
FIG. 18A is a side view of the introducer tool illustrated in FIG. 16.
FIG. 18B is a close-up view of a distal tip of the tool.

FIG. 18A is a top view of the tool 1004 and FIG. 18B is a close-up view of a distal end portion 1026 of the tool 1004.

In one embodiment, the tool 1004 includes a hook 1020 extending from a handle 1022 between a proximal end 15024 and a distal end portion 1026. The hook 1020 is a planar hook having a curve and is configured for an inside-out pass from a midline incision in the patient through a membrane tissue covering the obturator foramen. In one embodiment, the hook 1020 is formed of a suitable material, for example stainless steel, fashioned to lie in a plane (i.e., the hook 1020 is a "planar" hook) between the end 15024 and the distal end portion 1026. The illustrated embodiment of the hook 1020 in FIG. 18A is not a helical hook.

In one embodiment, the hook 1020 is a substantially solid hook (i.e., the hook does not include a lumen) having a curved section 1027 connected between a first linear section 1028 and a second linear section 1029. The curvature of the curved section 1027 is not constant as the curved section 1027 has greater curvature adjacent the second linear section 1029 as compared to the first linear section 1028. The second linear section 1029 is not parallel to the first linear section 1028, and a ray extending from and aligned with the second linear section will intersect a horizontal plane from which the proximal end 15024 of the hook 1020 extends.

The hook 1020/tool 1004 is configured to implant the support member 1002 into a male patient via an inside-out pass extending from a single perineal incision to an obturator foramen of the male patient, where the pass minimizes the possibility of undesirably perforating the urethra or the corpus cavernosa of the patient.

In one embodiment, the distal end portion 1026 of the hook 1020 (FIG. 18B) includes a distal end 1030, an L-shaped slot 1032 proximal the distal end 1030, and a T-shaped slot 1034 proximal the L-shaped slot. The hook 1020 is preferably formed from a stable material such as stainless steel and the handle 1022 is preferably formed from plastic, for example, although other materials are also acceptable.

Figure 19:
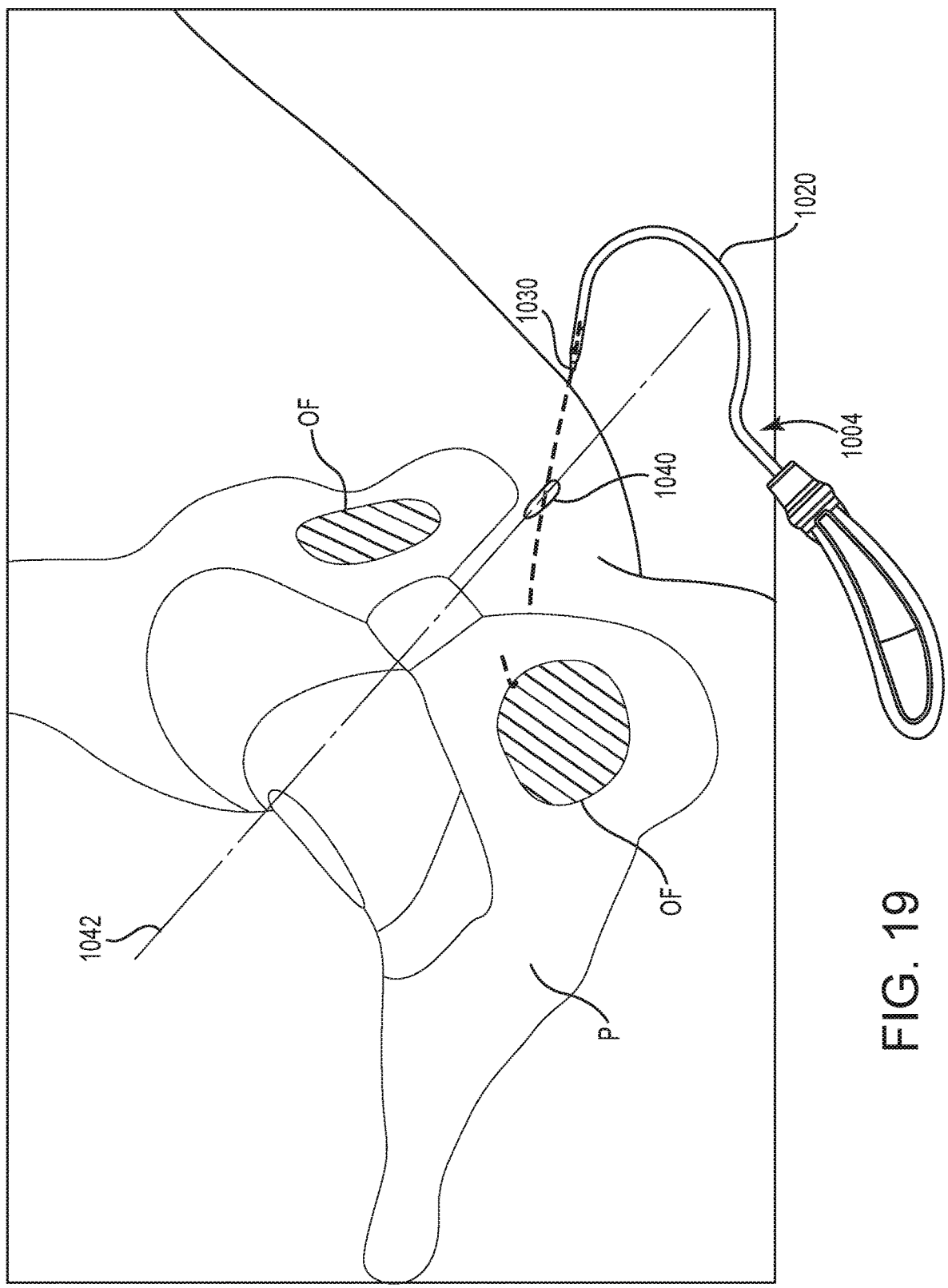
FIG. 19 is a schematic view of an inside-out insertion path for the tool entering through an incision and piercing an obturator foramen of the patient for placement of trans obturator arms of the support member.

FIG. 19 is a schematic view of a pelvis P of a patient having a pair of obturator foramen OF. The pelvis P is surgically accessed through a single, minimally invasive perineal incision 1040. A reference axis 1042 is provided that is aligned on a midline of the patient's body from the incision 1040 through the pubic symphysis. The reference axis 1042 separates the patient's body between the left side of the patient and the right side of the patient (e.g., the right side includes the illustrated obturator foramen OF).

The support member 1002 (FIG. 17) is implanted, for example, by forming the perineal incision 1040 and dissecting to isolate the bulbous urethra (for men) while ensuring that the bulbous spongiosis muscle remains intact. The surgeon will optionally, depending upon surgeon preference, dissect down to the pubic ramus to identify this landmark.

With reference to FIGS. 17 and 18B, the surgeon forms the perineal incision 1040 and employs the tool 1004 to guide each of the trans obturator arms 1012 along an inside-out path through the obturator foramen. For example, a distal end 1030 of the hook 1020 is engaged with the fixed anchor 136. The hook 1020 and the fixed anchor 136 are inserted into the perineal incision 1040, guided along an inside-out path that extends inward to a descending portion of the ramus of the patient, and into the membrane extending over the obturator foramen OF. The distal end 1030 of the hook 1020 penetrates the membrane extending over the obturator foramen OF with an audible "pop," indicating the fixed anchor 136 is attached to the membrane of the obturator foramen OF. In a similar maneuver, the distal end 1030 of the hook 1020 is engaged with the adjustable anchor 120, and the hook 1020 and adjustable anchor 120 are inserted into the perineal incision 1040, along a contra-lateral inside-out path to a descending portion of the ramus of the patient and into the membrane extending over the obturator foramen OF. Once again, when the distal end 1030 of the hook 1020 penetrates the foramen membrane an audible "pop" indicates a successful anchoring of the adjustable anchor 120 into the membrane of the obturator foramen.

In one embodiment, the suprapubic arms 1014 (having the optional sleeves 1016 of FIG. 17 removed) are inserted into the single perineal incision 1040 and tunneled into position subcutaneously within the patient. For example, the tool 1004 (or another suitable tool) is employed to insert the suprapubic arms 1014 into the incision 1040 suprapubically, at which location the arms 1014 are overlapped subcutaneously within the patient to allow tissue ingrowth to secure the support member 1002 within the patient.

Figure 20:
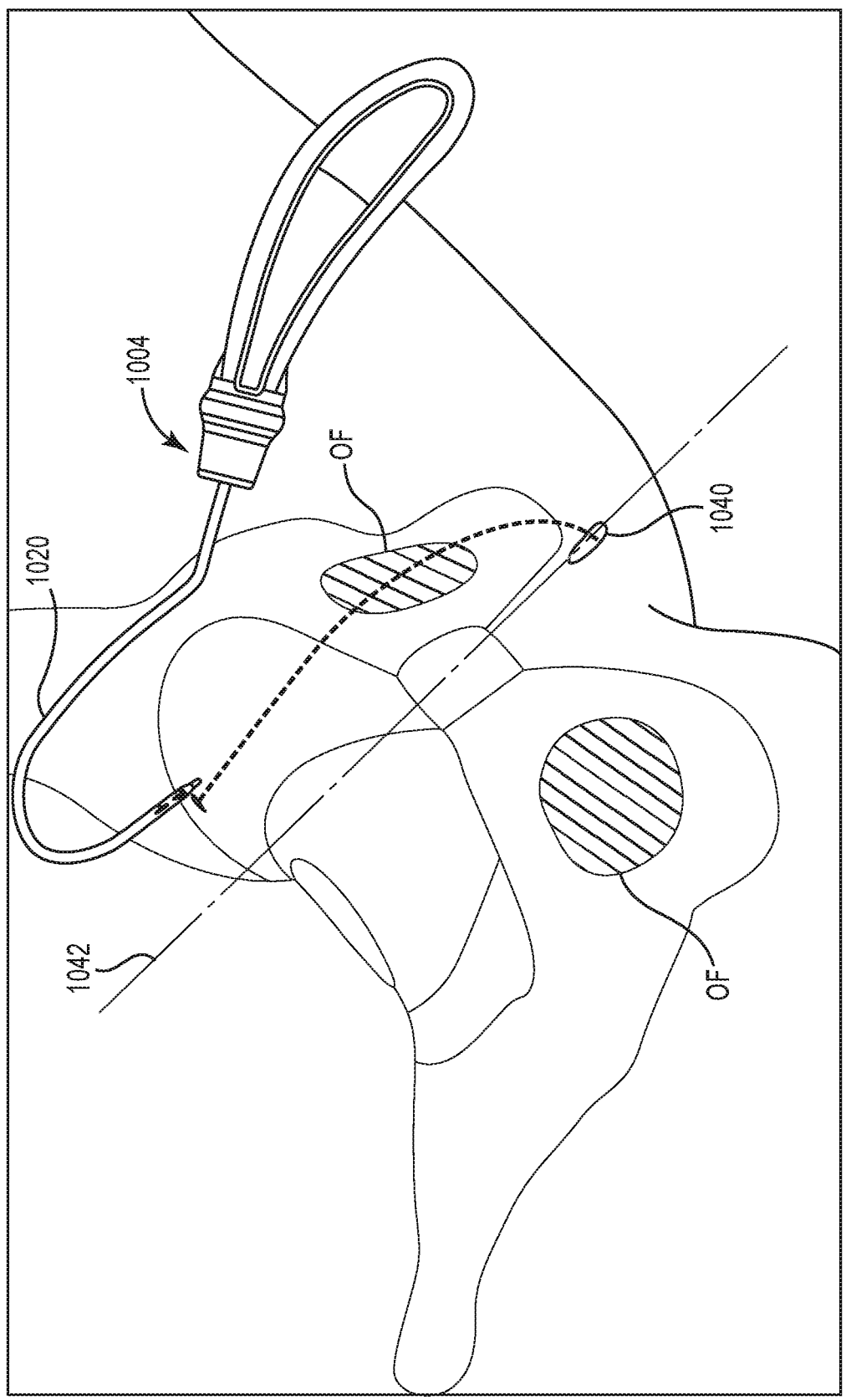
FIG. 20 is a schematic view of an insertion path for the tool taking an optional suprapubic approach from the abdomen down to the incision for placement of suprapubic arms of the support member.

With reference to FIGS. 17 and 20, in one embodiment the suprapubic arms 1014 (including the optional sleeves 1016 of FIG. 17) are implanted by the tool 1004 subcutaneously within the patient via a pre-pubic opening. For example, the distal end 1030 of the hook 1020 is inserted under the patient's skin and moved subcutaneously from the pre-pubic opening to the perineal incision 1040 lateral the urethra. One of the suprapubic arms 1014 is attached to the T-shaped slot 1034 and retracted backwards by the tool 1004 along the path from the perineal incision 1040 to the pre-pubic opening. The other suprapubic arm 1014 is implanted contra-laterally in a similar manner. Afterwards, the suture, the tip and the optional sleeves 1016 are removed from the suprapubic arms 1014 leaving the porous mesh in place for subsequent tissue ingrowth. In one embodiment, excess length of the suprapubic arms 1014 is trimmed flush with the patient's skin. In one embodiment, the suprapubic arms 1014 are crossed/overlapped one over the other subcutaneously.

The trans obturator arms 1012 are suspended/connected in a midline location between the membrane of the obturator foramen OF and the suprapubic arms 1014 are retained in a fixed position subcutaneously. In one embodiment, the interconnecting member 110 is pulled through the adjustable anchor 120 shorten the midline length between the ends of the trans obturator arms 1012 and adjust tension in the support member 1002. In this manner, support member 1002 elevates and compresses the ventral urethral bulb B of the patient. The suprapubic arms 1014 are pulled to adjust tension prior to being secured to each other, which compresses the perineal urethra U. The support member 1002 allows the surgeon to tighten or loosen the tension between the arms 1012 by adjusting the adjustable anchor 120.

Figure 21:
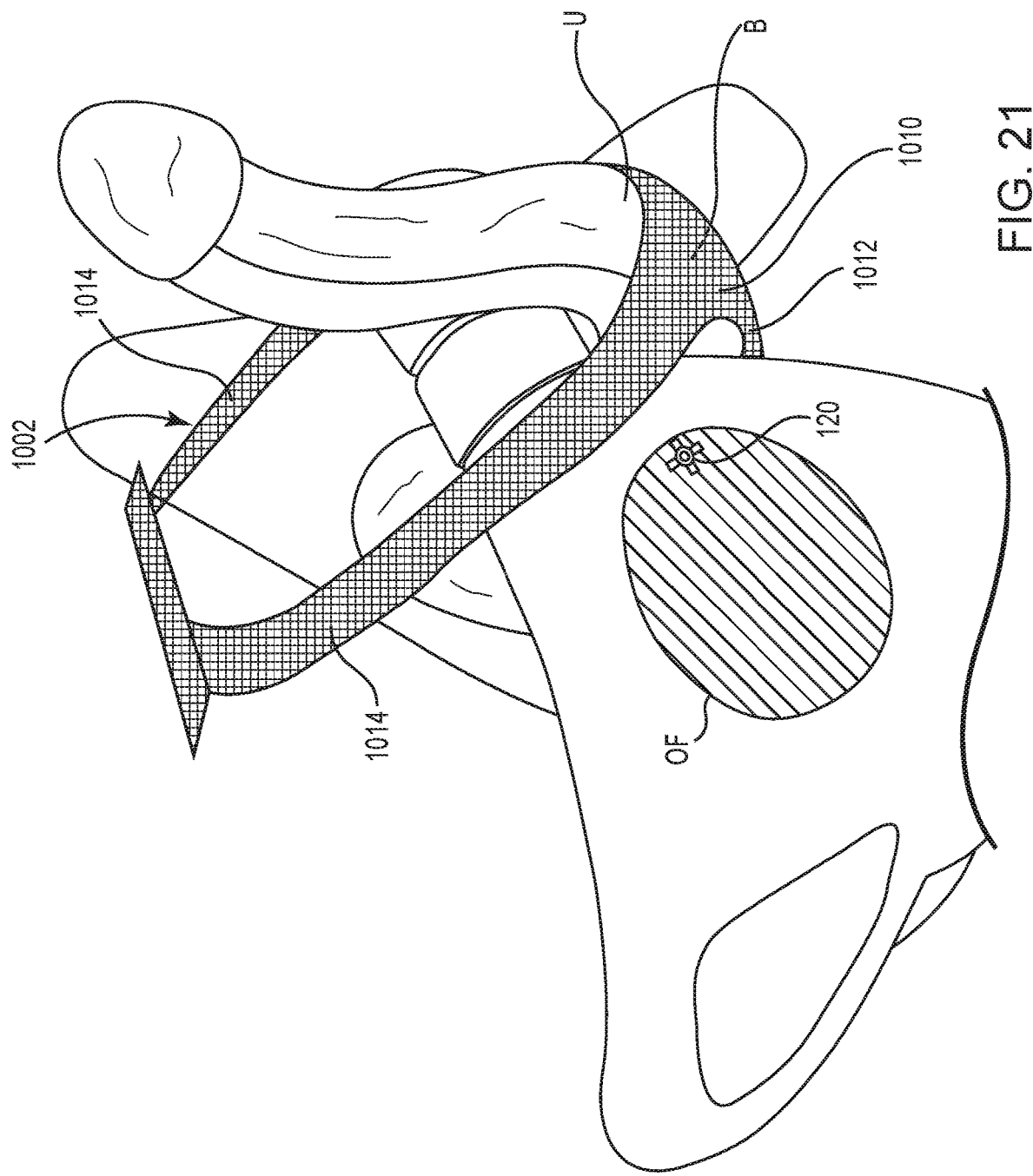
FIG. 21 is a schematic view of one embodiment of the adjustable support member illustrated in FIG. 17 as implanted via a single incision.

FIG. 21 is a schematic view of the support member 1002 implanted in a male patient. The illustration presents a sub-dermal view of the location of the support member 1002 relative to the ventral urethral bulb B of the patient. The trans obturator arms 1012 extend between membranes covering the obturator foramen OF and are adjustable via the adjustable anchor 120 to elevate and compress the ventral urethral bulb B of the patient. The suprapubic arms 1014 are tunneled subcutaneously to compress the perineal urethra U. The surgeon adjusts the tension/elevation of the support member 1002 by drawing the interconnecting member 110 through the adjustable anchor and adjusts the compression of the support member 1002 against the ventral urethral bulb B of the patient by selectively tightening the suprapubic arms 1014. This adjustment of the two pairs of arms 1012, 1014 may be done incrementally until the surgeon achieves the desired coaptation of the urethra U through the elevation and compression of the ventral urethral bulb B of the patient.

The implanted arms 1012, 1014 and the body portion 1010 allow tissue ingrowth through the support member 1002, which tends to provide a more durable and long-lasting support to address male incontinence.

The above-described approach to addressing urinary incontinence is less invasive than implanting an artificial urinary sphincter (artificial urinary sphincters can contribute to erosion of the urethra), which aids the patient to a faster recovery, and has the potential for immediate post-implantation beneficial continence results.

The adjustable anchor 120 of the support member 1002 is movable along the interconnecting member 110 to adjust the elevation of a mid-area (identified as supporting the bulbous urethra B) of the support 1002 relative to a urethra of the patient.

The elevation and compression of the urethra bulb provides Ventral Urethral Elevation (VUE) that ensures consistent placement of the support with a decreased probability of loosening. The minimal dissection of the bulbous urethra minimizes the potential for distal movement of the support member 1002. Support member 1002 is implanted through a single perineal incision 1040 that is less invasive than other surgical interventions for remedying male incontinence.

FIG. 22A is a perspective view of one embodiment of a support member 1100 including adjustable anchor 120 and a hanger 1102. In one embodiment, the support member 1100 is a substantially rectangular porous mesh termed a "tape," substantially as illustrated in FIG. 22A, and fabricated from materials similar to those described above for the sling 100 (FIG. 1). The support member 1100 is configured for implantation into a male patient or a female patient via a single midline incision (perineal for men and paraurethral or vaginal for women) and includes a mechanism for adjusting tension in the support 1100.

The adjustable anchor 120 described above is attached to the first end 1502 of the support member 1100 by the interconnecting member 110, and a hanger 1102 is attached to the second end 104 of the support member. In one embodiment, the hanger 1102 is fabricated from plastic and is attached to the end 104 of the support 1100 by welding, stitching, adhesive attachment, or another suitable form of attachment.

The hanger 1102 is configured to hang over a portion of a pubic ramus of a pelvis to secure a second end 104 of the support member 1100, and the adjustable anchor 120 is attachable to a membrane extending over an obturator foramen. The interconnecting member 110 slides relative to the anchor 120 to adjust the tension and support provided by the support member 1100. The hanger 1102 is configured to be placed over a surface of the pubic bone without the use of screws. In this manner, the hanger 1102 does not penetrate the bone, which allows the surgeon to more quickly and accurately place the support 1100 inside the patient.

FIG. 22B is a side view and FIG. 22C is a front view of the hanger 1102. In one embodiment, the hanger 1102 extends between a proximal end 1110 and a distal end 1112, and includes a curved hanging portion 1114. The proximal end 1110 is attached to the end 104 of the support 1100 (FIG. 22A). In one embodiment, the distal end 1112 converges to a point that is configured to penetrate the obturator foramen membrane and allow the hanging portion 1114 to engage with and drape over a pubic ramus. The hanging portion 1114 is curved to correspond to a curvature of the pubic ramus bone of the pelvis.

Figure 23:
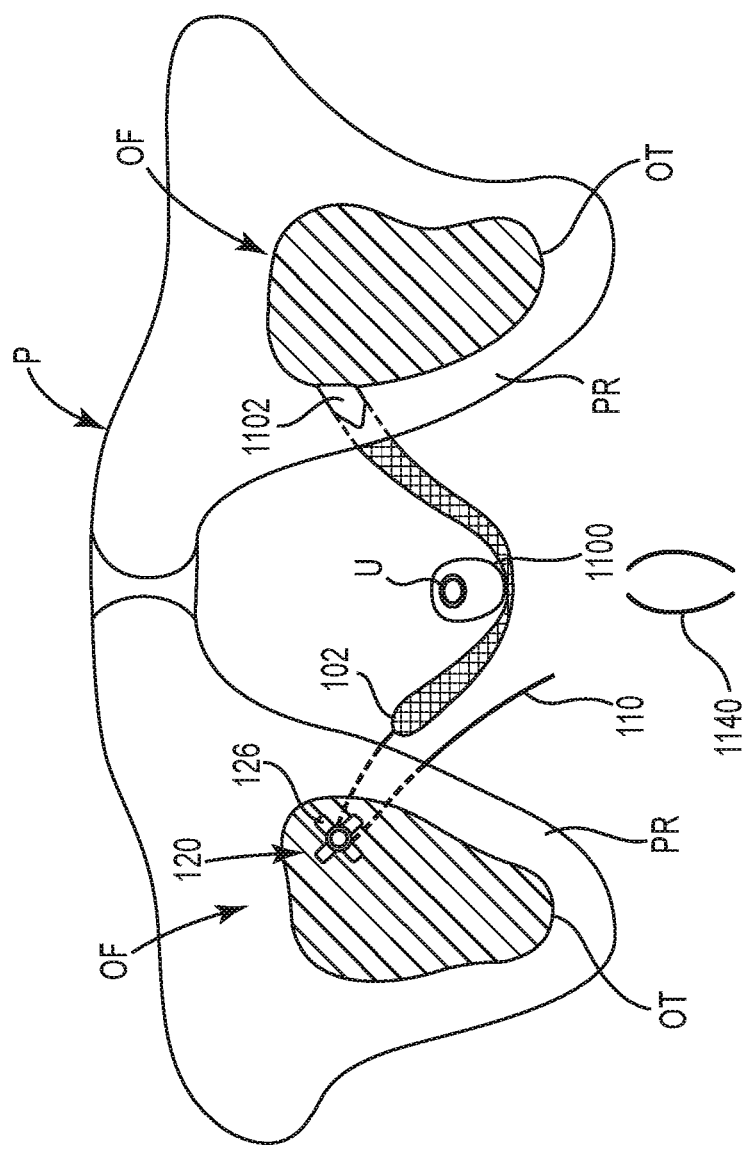
FIG. 23 is a schematic view of one embodiment of the support member illustrated in FIG. 22 implanted via a single incision with the adjustable anchor inserted in a membrane of an obturator foramen and the hanger secured over a portion of a ramus to allow the support member to alleviate pelvic dysfunction.

FIG. 23 is a schematic view of the support member 1100 attached between a pubic ramus PR of the pelvis P and tissue OT of the obturator foramen OF to support a urethra U of the patient. In one embodiment, the patient is a female and the support member 1100 supports the urethra U without compressing the urethra U. In one embodiment, the patient is a male and the support member 1100 supports the urethra U by elevating and compressing at least a portion of a bulb the urethra U.

It is to be understood that it is undesirable to dissect tissue away from and expose the urethra U (which can contribute to urethral erosion). The illustration of the figures shows a urethra U with a thickness to indicate tissue is still surrounding the urethra.

In one embodiment, the hanger 1102 is introduced through a single perineal incision 1140 along an inside out pass that places the hanger 1102 around a portion of the pubic ramus PR. For example, the surgeon places the hanger 1102 either digitally with a finger, or with a tool, into the incision 1140 and guides the hanger 1102 inward against the membrane covering the obturator foramen, after which the surgeon penetrates the membrane with the pointed distal end 1112 (FIG. 22C) of the hanger 1102. Movement of the pointed distal end 1112 of the hanger 1102 through the obturator foramen membrane positions the hanging portion 1114 for engagement over the pubic ramus PR.

The adjustable anchor 120 is guided through the incision 1140 with the tool 1004 (FIG. 18A) as described above in FIG. 19. The tension of the support member 1100 is adjusted by pulling on the interconnecting member 110 until a desired length of the support member 1100 is achieved that provides support to the tissue around the urethra U, as described above. In this manner, the adjustable anchor 120 of the support 1100 allows the elevation of mid-area of the support 1100 under the urethra to be adjusted to support the urethra without displacing or compressing the urethra (as desirable in a female). The surgeon closes the minimally invasive single incision 1140 according to acceptable practices. The support provides the patient with a state of continence immediately after implantation due to the support or support and elevation of the urethra U.

Figure 24:
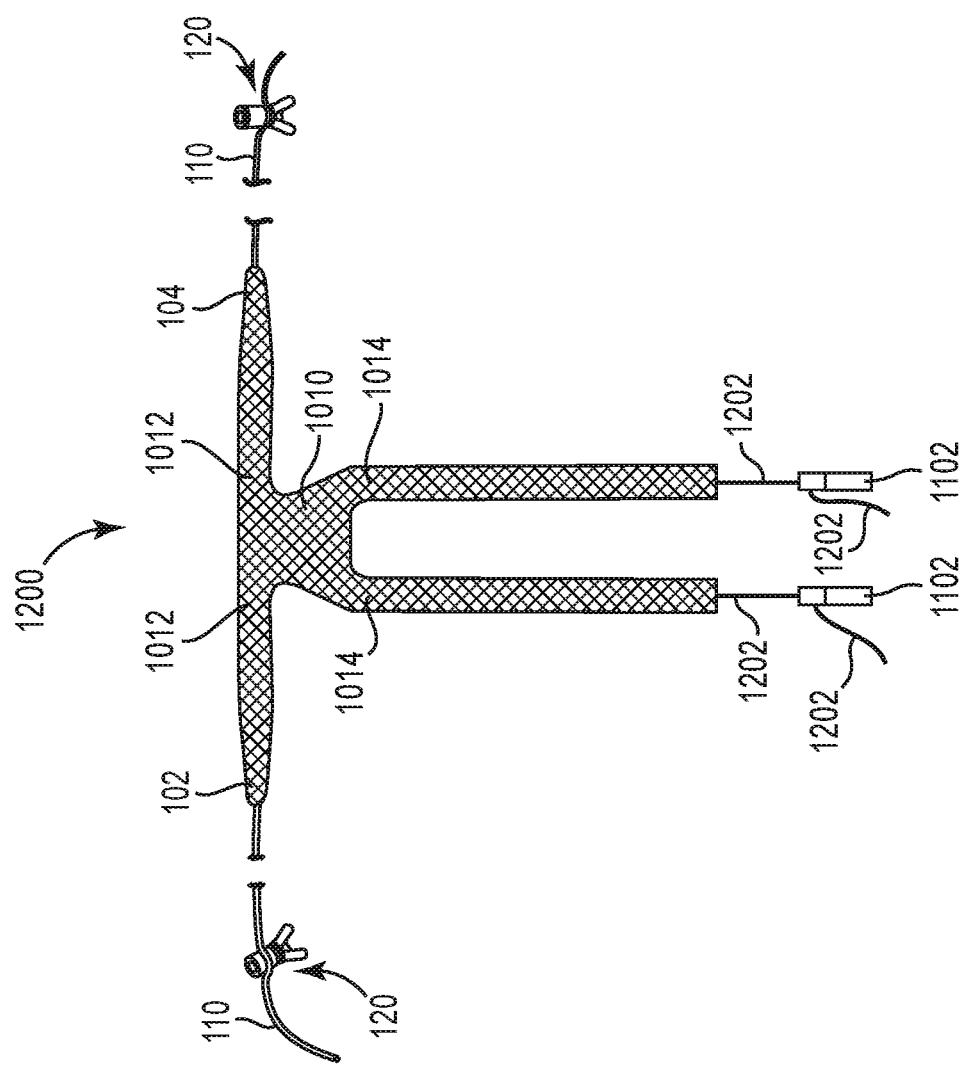
FIG. 24 is a top view of one embodiment of a support member including adjustable anchors and hangers and implantable via a single incision.

FIG. 24 is a top view of one embodiment of a support member 1200 including adjustable anchors 120 and adjustable hangers 1102 that allow the support 1200 to be implantable via a single incision. The support member 1200 is similar to the support member 1002 (FIG. 17) and includes the body portion 1010, and opposing trans obturator arms 1012 and suprapubic arms 1014 extending from the body portion 1010.

In one embodiment, an adjustable anchor 120 is attached to each of the opposing trans obturator arms 1012 by an interconnecting member 110, and the adjustable hanger 1102 is attached to each of the suprapubic arms 1014 by an adjustable suture 1202. The adjustable suture 1202 is configured to allow the independent adjustment of the distance between each hanger 1102 and the arm 1014 to which it is attached in a manner similar to that described above in FIGS. 2-4, for example. For example, the adjustable hanger 1102 is movable distally and proximally along the suture line 1202 to allow for the selected and independent adjustment of the hanger 1102 relative to the support 1200. The support member 1200 is configured for implantation into the patient via a single incision, and as such, the optional sleeves 1016 (FIG. 17) covering one or more of the arms are not provided on the support member 1200.

The support member 1200 is fabricated from the materials described above, and in one embodiment is provided as a porous polypropylene mesh having a pore size of about 665 micrometers, a porous area of about 42.3% of the total area, a basis weight of about 119 g/m², and a thinness of about 635 micrometers.

The adjustable anchors 120 and hangers 1102 are as described above. It is to be understood that the support 1200 could be provided with four adjustable anchors 120 or four adjustable hangers 1102, or combinations of adjustable anchors and hangers. During implantation, the surgeon selectively and independently adjusts each anchor 120 and each hanger 1102 by sliding the adjustable component along its respective line 110, 1202 to achieve the desired amount of support or elevation or compression of the implanted support 1200 relative to the patient's anatomy.

Figure 25:
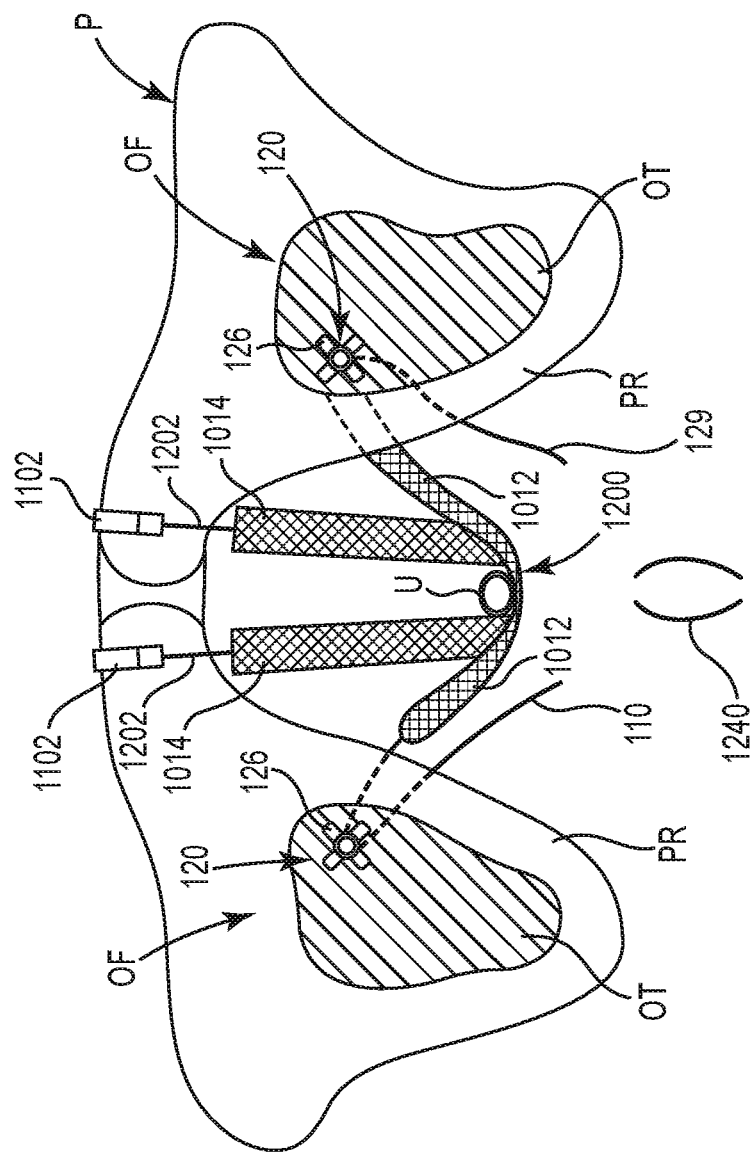
FIG. 25 is a schematic view of one embodiment of the adjustable anchors of FIG. 24 anchored to membranes of obturator foramen and the hangers secured to the pelvis.

FIG. 25 is a schematic view of one embodiment of the support member 1200 having the adjustable anchors 120 attached to membranes of obturator foramen OF and the hangers thousand 102 secured to the pelvis P.

In one embodiment, support member 1200 is implanted into the pelvis of the patient through a single midline incision 1240. In a male example, the adjustable anchors 120 are implanted through a perineal incision of a man and attached to the membrane tissue OT extending over the obturator foramen OF by the tool 1004 (FIG. 16) via the approach described above. In a female example, the adjustable anchors 120 are implanted through a vaginal incision of a woman and attached to the membrane tissue OT extending over the obturator foramen OF by the tool 1004 (FIG. 16) via the approach described above.

In particular, one of the adjustable anchors 120 is attached to the distal end 1030 of the tool 1004, the distal end 1030 and the adjustable anchor 120 are inserted through the incision 1240 and guided to a location superior the pubic ramus PR where the tool 1004 forces the adjustable anchor 120 into the membrane OT of the obturator foramen OF to attach one of the trans obturator arms 1012 to the patient. A similar maneuver is carried out on the contra-lateral side of the patient to implant the other of the trans obturator arms 1012.

In one embodiment, suprapubic arms 1014 are each inserted individually and guided suprapubically and subcutaneously to a prominence of the pelvis P over which the anchors 1102 are hung. The suture line 1202 is adjusted to place the arm 1014 in the desired location. Alternatively, a tool or other device is employed to guide the hangers 1102 subcutaneously to the pelvis P.

The anchors 120 are adjusted to support to the urethra U by sliding one (or both) of the interconnecting members 110 through a respective one of the adjustable anchor 120 after implantation of the support member 1200 in the manner described above. In this manner, tension provided by the support member 1200 relative to the urethra U is adjustable by the surgeon to achieve compression and elevation of the urethra U in a man or support without compression of the urethra in a woman. Each of the adjustable anchors 120 is individually adjustable to allow the urethra U to be centered relative to the trans obturator arms 1012.

Figure 26:
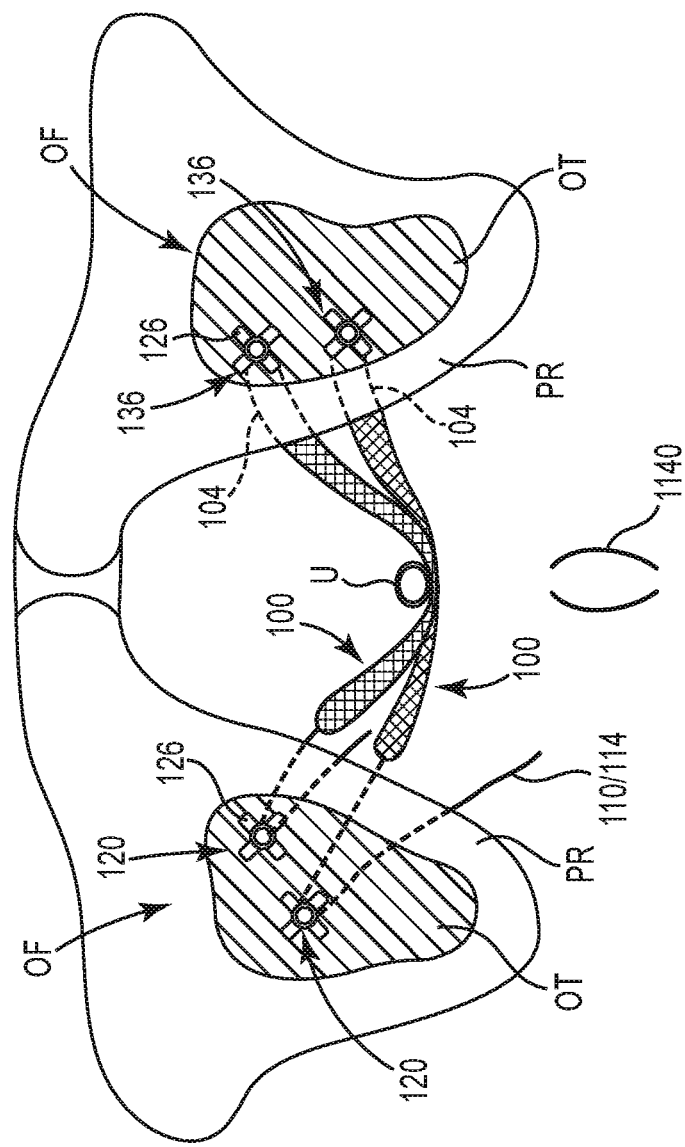
FIG. 26 is a schematic view of a pair of adjustable supports as illustrated in FIG. 1 implanted into a patient via a single incision to alleviate pelvic dysfunction.

FIG. 26 is a schematic view of a pair of adjustable slings 100 as illustrated in FIG. 1 implanted into a patient via a single incision 1140 to alleviate pelvic dysfunction.

In one embodiment, two or more slings 100 are implanted into a male patient through a single minimally invasive perineal incision 1140 (for example with tool 1004) and held in place by anchors 120, 136. The adjustable anchor 120 permits each sling 100 to be adjusted. In addition, each sling 100 is configured to be selectively positioned by the surgeon to provide elevation and compression of the urethral bulb around the urethra U of a male patient.

In one embodiment, two or more slings 100 are implanted into a female patient through a single minimally invasive vaginal incision 1140 (again, with the tool 1004) and held in place by the anchors 120, 136. The adjustable anchor 120 permits each sling 100 to be adjusted. The surgeon may selectively position each sling 100 to provide support for the urethra of the female without compression of the urethra, which can undesirably erode the short female urethra.

By the embodiments described above, adjustable slings and supports are provided that are configured to be implanted into the patient (male or female) through one minimally invasive single incision. The adjustable support provides an immediate remedy to the incontinence of the patient because of the tensioned and adjustable arms in combination with the rapid healing of the minimally invasive procedure.

It is to be again appreciated that components of these devices could be reversed, if desired, in a right side/left side sense from their arrangements as shown in the examples of FIGS. 1 and 5. It is also to be appreciated that method steps could be performed in other sequences.

It is also to be appreciated that the examples of methods described herein, for surgical placement of devices for anatomical support, do not require skin exits or incisions other than for a single vaginal incision (or, in a male patient, a single perineal incision) for placement and adjustment.

Upon occurrence of tissue in-growth, after implantation surgery is completed and during the patient's healing process, anchors might then become unnecessary to continue to secure the anatomical support device in the patient. Therefore, any of the anchors and the interconnecting members could be made of a suitable medical grade bioresorbable material.

It is to be also appreciated that the foregoing examples of implantable devices for anatomical support provide means for adjustment or tensioning of anatomical support members that are not dependent upon anchor placement. For example, increased tensioning of the devices may be advantageously achieved without a need for advancing anchors more deeply into target tissue in the patient. Also, the aforedescribed frictional sliding engagement between interconnecting member 110 and adjustable anchor 120—or between interconnecting member 110 and tensioning element 530—permits novel intra-operative adjustment of the implantable devices for anatomical support disclosed herein. Furthermore adjustable anchor 120, as well as the combination of anchor 520 with tensioning element 530, permits such intra-operative adjustment to be performed as many times as desired during a particular implantation procedure, to achieve optimal device placement, adjustment, and tensioning.

While implantable devices, tools, and methods for anatomical support have been particularly shown and described herein with reference to the accompanying specification and drawings, it will be understood however that other modifications thereto are of course possible; and all of which are intended to be within the true spirit and scope of the claimed invention. It should be appreciated that (i) components, dimensions, shapes, and other particulars of the example embodiments herein may be substituted for others that are suitable for achieving desired results, (ii) various additions or deletions may be made thereto, and (iii) features of the foregoing examples may also be made in combinations thereof. It is also to be understood in general that any suitable alternatives may be employed to provide these implantable devices, tools, and methods for anatomical support.

Lastly, choices of compositions, sizes, and strengths of various aforementioned elements, components, and steps all depend upon intended uses thereof. Accordingly, these and other various changes or modifications in form and detail may also be made, again without departing from the true spirit and scope of the invention as defined by the appended claims.

Single Incision Incontinence Treatment Device

The features of the various exemplary embodiments described in this application are suitable and intended to be combined with each other, unless specifically noted otherwise.

Anterior means "forward" or "front," and posterior means "rearward" or "back." Relative to surfaces of an organ in the human body, an anterior surface of an instrument inserted into the organ will be oriented forward toward the belly and a posterior surface will be oriented rearward toward the spine.

End means an end-most location and end portion means that segment adjacent to and near the end of an object. For example, two opposing ends of an object are each equidistant from a mid-point of the object and between the mid-point and each end of the object is an end portion of the object.

Soft tissue is tissue other than bone. Soft tissue is not bone.

Embodiments provide a combination of anchors, including the anchors 120, 136 described above and the anchor 1442 described below, employed to fixate a support in soft tissue in treating urinary incontinence. The anchors and support are implantable through a single (one and only one) incision to support the urethra.

Embodiments provide a tissue anchor having a geometric asymmetry and asymmetric mass distribution along a length of the anchor which encourages the anchor to be rotated into a stable configuration in the tissue.

Embodiments provide a tissue anchor that is adjustable by capturing a suture in sliding arrangement between a body and a collar of the anchor. Such an anchor can be provided as a fixed anchor when the suture is fixed between the body and the collar of the anchor.

Embodiments provide a system including anchors attached to a support, where the anchors are attached to the support and include a combination of the anchor(s) having the geometric asymmetry and the asymmetric mass distribution along a length of the anchor and non-adjustable and adjustable tissue anchor(s) with a suture located between the body and the collar of the anchor.

Embodiments provide a tissue anchor system having an anchor that will durably anchor into periosteum tissue covering a bony surface, or durably anchor into dense fibrous tissue where muscle inserts into the bone. An anchor so anchored is suitable for suspending support material or is useful in implanting devices in the human body.

Embodiments provide a tissue anchor system including an introducer that is configured to deliver an anchor to an intracorporeal tissue site. The introducer includes a cannula that allows placement of an anchor at a landmark in tissue deep within an incision site, which may be out of the field of vision of the surgeon. The anchor is configured to be secured within the cannula so that it does not rotate or fall out of the cannula during insertion into the tissue. A length of suture is provided that is attached to the anchor, where the suture may be tied or otherwise terminated to itself outside of the incision site and then subsequently directed to the intracorporeal landmark.

Embodiments provide a tissue anchor system provided to treat male urinary incontinence that is advantageously implanted through a single incision formed in the patient. A first anchor is anchored to the tissue of a first obturator foramen of the patient, and a second anchor is anchored to the tissue of a second obturator foramen of the patient to secure in inferior portion of the support material to the patient. A third anchor is provided to anchor a first pre-pubic arm to the periosteum tissue on one side of the pubic symphysis, and a fourth anchor is provided to anchor a second pre-pubic arm of the support material to the periosteum tissue on the other side of the pubic symphysis. Each of the anchor assemblies includes a suture extending from the anchor to the support.

In one approach, the surgeon is instructed to suitably terminate or tighten the suture to capture the support material between a knot formed in the suture and the anchor implanted in the tissue. The surgeon, guided by experience and instruction provided with the tissue anchor system, first centers and fixates the inferior portion of the support material relative to the obturator foramen by suitably tensioning and tying knots in the suture. Subsequently, the surgeon centers and fixates the superior portion of the support material near an upper portion of the pelvis on either side of the pubic symphysis. Some aspects of the tissue anchoring system include a separate plication mechanism provided to take up the slack in tension the support material over the tissue of the urethra.

Embodiments of the system described in this specification provide a support material that is implantable into the patient through a single incision with anchor assemblies that do not create a second or other incisions/openings in the skin. The system obviates the use of transobturator arms and additional tools that tunnel the pre-pubic arms under the skin. The system is easier to implant compared to a four arm or six arm support, and reduces the amount of time that the patient is in the operating room.

One approach to treating urinary incontinence places a support inferior to the urethra and directs arms upward from the support alongside the bladder along a U-shaped pathway. A significant advance over the U-shaped pathway was provided by Dr. Emmanuel Delorme as described in his U.S. Pat. No. 6,638,211 and included placing arms of a support through the obturator foramen along a V-shaped pathway. This application provides another advance in supporting the pelvic anatomy by recognizing that support material can be robustly attached to the periosteum tissue through the use of an anchoring system. The anchoring system allows the surgeon to place the support inside of the patient and directly fixate the support to periosteum tissue that is present over the exterior of the pelvis bone. This approach does away with needles and other tools that tunnel the arms of a support through tissue. The anchoring system described in this application is compatible with a true single (only one) incision formed in the patient.

Figure 27:
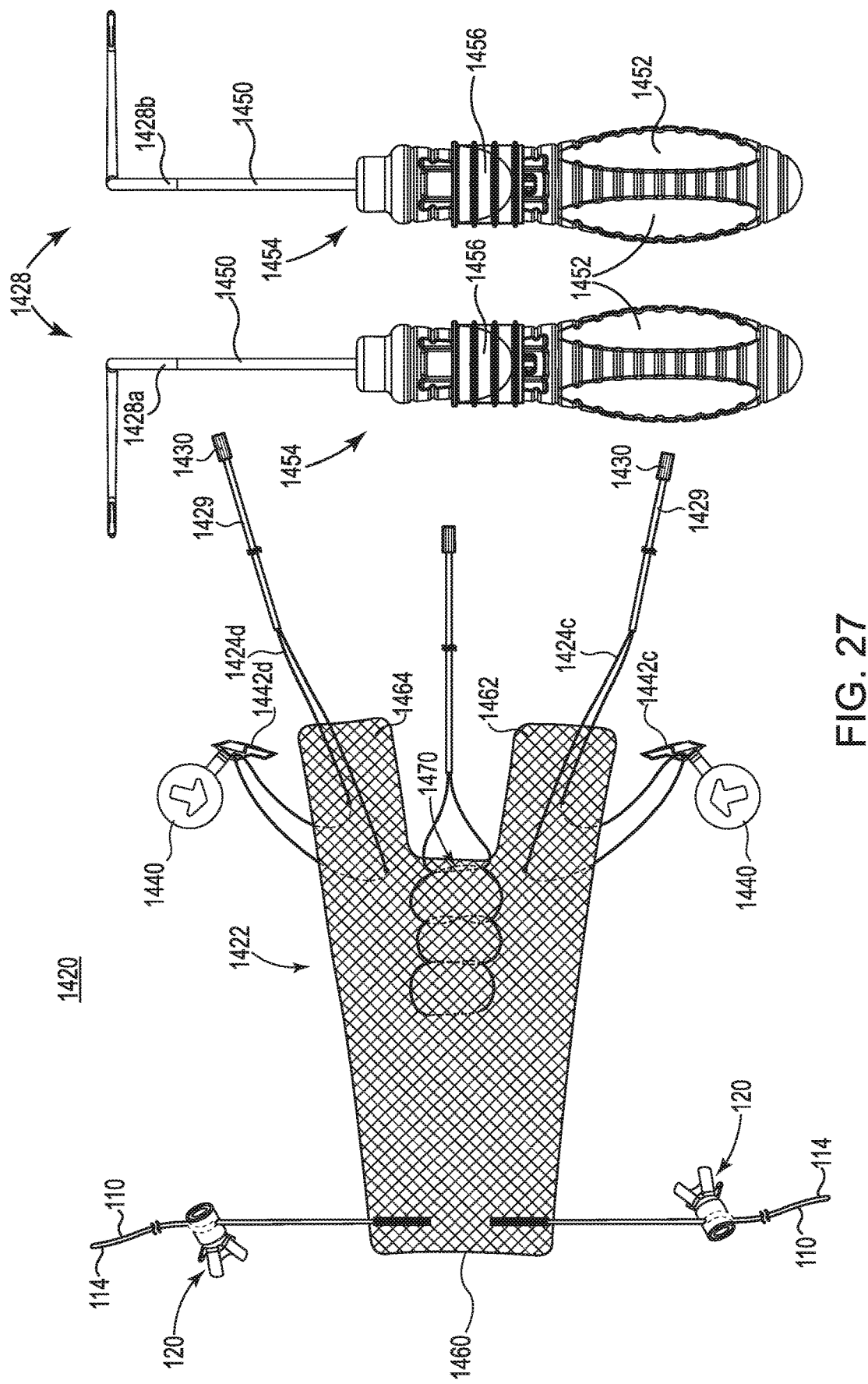
FIG. 27 is a top view of one embodiment of a tissue anchor system including a support material, an anchor assembly, and an introducer.

FIG. 27 is a top view of one embodiment of a tissue anchor system 1420 (the system 1420) of an incontinence treatment device. The system 1420 is illustrated in one useful form for delivery to an end-user healthcare facility and includes opposing anchors 120 attached to opposing sides of a support material 1422 by the interconnecting member 110, sutures 1424 (1424c, 1424d) engaged with the support material 1422, an anchor assembly 1426 engaged with each of the sutures 1424c, 1424d, and a set of introducers 1428.

The incontinence treatment device of the system 1420 includes a support 1422 having a base 1460 and two arms 1462, 1464 extending away from the base 1460, and a system of anchors 120, 1442c, 1442d connected to the support.

With reference to FIGS. 2-4, the anchor 120 is provided as a first anchor 120 having those features described above including a body 122 defining a first central longitudinal axis, a collar 128 defining a second central longitudinal axis with the collar 128 received over the body 122 such that the first central longitudinal axis and the second central longitudinal axis are parallel and laterally offset, and a first strand 110 extending through the collar 128 and received between the body 122 and the collar 128 with the first strand frictionally engaged by the body 122 and the collar 128 and secured to the support 1422.

Two adjustable anchors 120 are illustrated in FIG. 27. The surgeon will place one of the anchors 120 into the tissue in the obturator foramen and then place the other anchor 120 into tissue of the opposing obturator foramen. The adjustable anchors 120 described above allow the surgeon to adjust a location and tension of the support 1422 by pulling on the interconnecting member 110 after placement of the anchors. Two adjustable anchors 120 provide the surgeon with more latitude for adjustment, however it is to be understood that one or both of the adjustable anchors 120 could be replaced with the fixed anchor 136 described above.

The second anchor 1442 is described below and includes a pointed leading tip 1502, a leading end portion 1500 extending from the leading tip 1502, a trailing end portion 1504 connected to the leading end portion 1500 with the trailing end portion 1504 terminating in a trailing tip 1506 that is located opposite of the leading tip 1502. First and second protrusions 1510 are formed on opposing sides of the leading end portion 1500 with each of the first and second protrusions 1510 extending outward in a radial direction perpendicular to a long axis of the second anchor 1442. A tissue engaging fin 1446 is integrated with the leading end portion 1500 and oriented in a direction perpendicular to the radial direction of the first and second protrusions 1510. An eyelet 1448 is formed through the tissue engaging fin 1446 with a second strand 1424 inserted through the eyelet 1448 and secured to the support 1422. A gripping tab 1440 is removably attached to the tissue engaging fin 1446.

The support material 1422 is provided to support the urethra when implanted in the patient. Suitable materials for the support material 1422 include autograft material (the patient's own tissue), allograft material (tissue from a cadaver), xenograft material (tissue from another species), or synthetic materials such as woven fabrics, knitted fabrics, meshes, nonwoven fabrics, meshes, fibrillated fibers, or spun and fibrillated fibers. In some embodiments, the support material 1422 is fabricated to include voids (pores) configured to allow tissue ingrowth into the support material 1422. The pores are generally larger, on average, than 75 µm. One suitable support material 1422 is a knitted polypropylene mesh, where each strand of the mesh is knitted from a polypropylene filament.

The sutures 110, 1424 are threaded through or otherwise engaged with the support material 1422. Each suture 1424 is threaded through or otherwise engaged with one anchor assembly 1426. One suitable suture 1424 is fabricated from a single monofilament of polypropylene that is threaded through both the anchor assembly 1426 and the support material 1422 to form a continuous closed loop of suture. In one embodiment, the trailing end portions of each suture 1424 are brought together and maintained within a conduit 1429, and at least the ends of the suture 1424 are welded (heat welded or sonically welded) together to maintain the ends of the continuous closed loop of suture in an organized fashion until the surgeon desires to break the suture 1424 at the point of the weld. In one embodiment, the weld is a break pad 1430 that is formed by crushing the ends of the suture 1424 into a flat structure that is more brittle than and easier to break than the suture 1424 is itself. The break pad 1430 maintains the suture 1424 in an organized fashion until the surgeon desires to access the free ends of the suture 1424, for example to tie a knot. In one embodiment, the welded break pad 1430 is formed through the ends of the suture 1424 and through the conduit 1429. The conduit 1429 advantageously allows the surgeon to identify which suture strand is associated with each portion of the support 1422 and also manages the sutures into an organized bundle for ease of handling during implantation of the support 1422.

The anchor assembly 1426 includes an insertion tab 1440 that is removably secured to an anchor 1442. The anchor 1442 includes a body 1444, a tissue engagement fin 1446 attached to the body 1444, and an eyelet 1448 formed in the tissue engagement fin 1446. The suture 1424 is threaded through the eyelet 1448 and gathered/secured at the break pad 1430. The insertion tab 1440 provides a convenient handle for the surgeon or the surgical staff to handle the anchor 1442. The length of the anchor 1442 is in a range from about 4-20 mm, which can present a small area for grasping when a person is wearing surgical gloves. The insertion tab 1440 allows the surgeon or the surgical staff to handle the anchor 1442 comfortably when loading the anchor 1442 into the introducer 1428.

Each of the first anchors 120 is implantable into an obturator foramen of the patient through the use of one of the tools 600 (FIG. 11) described above. The introducers 1428 are employed to secure the anchor assemblies 1426 into periosteum tissue associated with the pelvis. In one embodiment, the introducers 1428 are multi-purpose introducers that are suitable to also and additionally pass one anchor 120 to the patient's right side obturator membrane and a second anchor 120 to the patient's left side obturator membrane.

Each of the introducers 1428a, 1428b includes a cannula 1450 extending from a handle 1452, and an ejection mechanism 1454 including a button 1456 that communicates with a rod/wire disposed within the cannula 1450. Movement of the button 1456 in a distal direction (forward) moves the rod/wire in a distal direction, which acts upon the anchor 1442 to eject the anchor out of the cannula 1450. The introducers 1428a, 1428b have a "handedness" depending on whether the anchor 1442 is into a left or a right obturator foramen. However, each introducer 1428a or 1428b is equally well suited for inserting one of the anchors 1442 into periosteum tissue.

An optional a plication mechanism 1470 is engaged with the support material 1422. The plication mechanism 1470 operates to gather up any slack that might be present in the support 1422 after implantation.

Each of the anchors 1442 include an insertion tab 1440 and engaged with the support material 1422. The anchors 1442 are located between the support 1422 and the patient's body, and the conduits 1429 and the break pads 1430 are located between the support 1422 and the surgeon. Thus, relative to the support 1422, the anchors 1442 are located posterior (distal the surgeon) and the conduits 1429/break pads 1430 are located anterior (proximal the surgeon).

Each of the anchors 1442 is engaged with the support material 1422 by a respective suture 1424, where each suture 1424 penetrates the support 1422 at more than one location. In the embodiment illustrated, each suture 1424 penetrates the support 1422 at two locations. We studied the effectiveness of the compression provided by the support 1422 in elevating and compressing the urethra and have determined that the multiplicity of penetrations of the support 1422 by the suture 1424 provides optimal support to the urethra. For example, two penetration points for the sutures 120 on each side of the base 1460 (four penetrations total for two sutures) provides excellent suspension of the base 1460 between the obturator foramen when the support 1422 is implanted. Two penetration points oriented on a diagonal line from an interior location of an arm 1462, 1464 to an outside corner of each arm 1462, 1464 for each suture 1424 has been determined to provide excellent tension to the support 1422 when implanted.

The support material 1422 includes a base 1460 associated with the first anchor 120 that is provided to be anchored into a first obturator membrane and a second anchor 120 that is provided to be anchored into a second obturator membrane of the patient. The support material 1422 additionally includes a first pre-pubic arms 1462 associated with a third anchor 1442c that is provided to be anchored into the periosteum tissue on one side of the pubic symphysis, and a second pre-pubic arms 1464 associated with a fourth anchor 1442d that is provided to be anchored into the periosteum tissue on the other side of the pubic symphysis. The support material 1422 is provided to the hospital or the surgeon in a package with instructions for use.

In one embodiment, a plication mechanism 1470 is engaged with the support material 1422. The plication mechanism 1470 is provided to allow the surgeon to remove slack from a central region of the support material 1422 after the base 1460 and the pre-pubic arms 1462, 1464 have been secured to tissue. In one embodiment, the plication mechanism 1470 is a single strand of polypropylene suture that is looped into a three-circle configuration (a snowman configuration). When force is applied to the free ends of the plication mechanism 1470, each of the circles in the three-circle configuration is contracted to remove the slack from the central portion of the support material 1422. The ends for the plication mechanism 1470 can be welded into a break pad, or are tied into a suitable knot to tension the support material 1422 against the tissue of the urethra. The plication mechanism 1470 may be removed from the support 1422 by the surgeon after implantation if it is determined that the support material 1422 is lying as desired over the tissue. In one embodiment, the plication mechanism 1470 includes a conduit provided to manage the loose ends of the plication suture.

One approach to attaching the support 1422 in treating male urinary incontinence is made with reference to FIG. 27. The patient is placed in gentle lithotomy position with buttock at the edge of the table. A Foley catheter is inserted into the patient, for example a 14 French Foley catheter. A single (one and only one) incision (about 4-6 cm) is made vertically in the perineal tissue 1 cm anterior to the anus. The surgeon is instructed to dissect down to and isolate the ventral bulbous urethra keeping the bulbospongiosus muscle intact. The surgeon is instructed to expose the bulbospongiosus muscle and take down the central tendon 2 cm to provide urethral mobility and allow for sling re-approximation. The surgeon is instructed to dissect sufficiently to accommodate the entire support 1422 and for incorporation of a wound retractor.

The system 1420 is appropriate both for use in procedures where the surgeon dissects the bulbous spongiosis muscle and in procedures where the surgeon does not dissect the bulbous spongiosis muscle, as depends upon surgeon preference.

One of the anchors 120 is placed in the obturator foramen following a trans-obturator (TO) path that is referred to as a TO approach. The introducer 600 (FIG. 11) is directed through the incision using an inside-out technique to guide the anchor 120 through the membrane over one of the left or right obturator foramen. The introducer 600 is started along a passage about 2 finger breadths (approximately 4 cm) below the pubic arch. The shaft of the introducer 600 should be parallel with the ipsilateral ischial pubic ramus. Using the thumb, push the introducer 600 posterior past the ischial pubic ramus, advancing through the obturator membrane until a pop is heard or felt. Once the "pop" is felt, rotate an additional ¾ turn (thumb slide should be facing up). The anchor 120 is thus inserted into the obturator externus muscle.

The surgeon is instructed to withdraw the first introducer 600 and place the other anchor 120 on the contralateral side of the patient with the other introducer (600Left or 600Right). The interconnecting member 110 or strand 110 is pulled to create tension on the support 1422 relative to the implanted and secured anchor 120.

The arms 1462, 1464 are lifted to tension the support 1422 against the bulbous spongiosis muscle. While holding the arms 1462, 1464 in tension, a third anchor is loaded into the introducer 1428, and the introducer 1428 is directed through the incision to guide the anchor 1442 under the periosteum tissue but above the bone. Specifically, the surgeon is instructed to place the tip of the introducer 1428 perpendicular to the tissue and gently press down to contact the pubic bone, skive along bone aiming toward the patient's ipsilateral shoulder maintaining contact for approximately 1.5 cm, then allow the needle to rotate away from the bone, followed by pushing the anchor 1442 approximately 1 cm farther. The introducer 1428 and the anchor 1442 in the introducer 1428 may be repositioned as desired by the surgeon. The surgeon is instructed to deploy the anchor 1442 from introducer 1428 using the thumb advance 56 and counter rotate to withdraw the introducer 1428 leaving the anchor 1442 in the dense fibrous tissue of the periosteum. The introducer 1428 and the anchor 1442 may be repositioned as desired by the surgeon until the anchor 1442 is physically expelled from the introducer. The surgeon is instructed to pull on the suture 1424 to seat anchor 1442 in the tissue to ensure integrity of the anchoring. The suture 1424 attached to the anchor 1442 is pulled and the anchor 1442 turns or toggles to fully engage the anchor 1442 in a sideways orientation relative to the line of entry of the introducer 1428 in the periosteum tissue. The anchor 1442 is engaged with the periosteum tissue to hold the support in tension against the urethral complex. The fourth anchor is loaded into the introducer 1428, and introducer 1428 is directed through the incision to guide the anchor 1442 through into and under the periosteum tissue on the contralateral side of the pubic symphysis of the patient. The surgeon is instructed to remove the conduit(s) from the suture 1424 followed by tying of a double overhand knot in the sutures 1424 to hold the support 1422 in compression against the urethra.

The surgeon is instructed to center the support 1422 on the bulbospongiosus muscle, using a stay suture if desired. The surgeon is instructed to retract the catheter from the glans penis. The surgeon is instructed to remove the conduit 1429 from the suture 1424 and to separate suture ends by pulling apart the break pad 1430. The surgeon is instructed to tie a double overhand knot on both sutures to secure the support 1422 down onto tissue, taking care to keep the support 1422 centered. The surgeon is instructed to drive the knot down towards the anchor 1442, keeping the support 1422 centered, to firmly secure the implant for optimum urethral re-approximation. The surgeon is instructed to tie additional overhand knots to lock the support 1422 in place, followed by trimming and discarding the removed excess suture.

The knots are tightened to secure and stretch anterior portion of the support 1422 over the urethra to provide optimum compression. Tie additional knots to lock in place, trim and discard excess suture. The surgeon may perform flexible cystoscopy to ensure appropriate coaptation of the urethra is achieved.

In this approach, the support 1422 is secured and suspended by the sutures 110 between the opposing obturator foramen and held in tension against the bulbous spongiosis muscle of the urethra by anchoring two anchors 1442 in the periosteum tissue on opposed lateral sides of the pubic symphysis. If the surgeon decides that additional gathering of the support 1422 over the urethra is desired, the surgeon will use the plication mechanism 1470 to take up any slack in the mid-region of the support 1422 to ensure appropriate elevation and support of the urethra.

Figure 28:
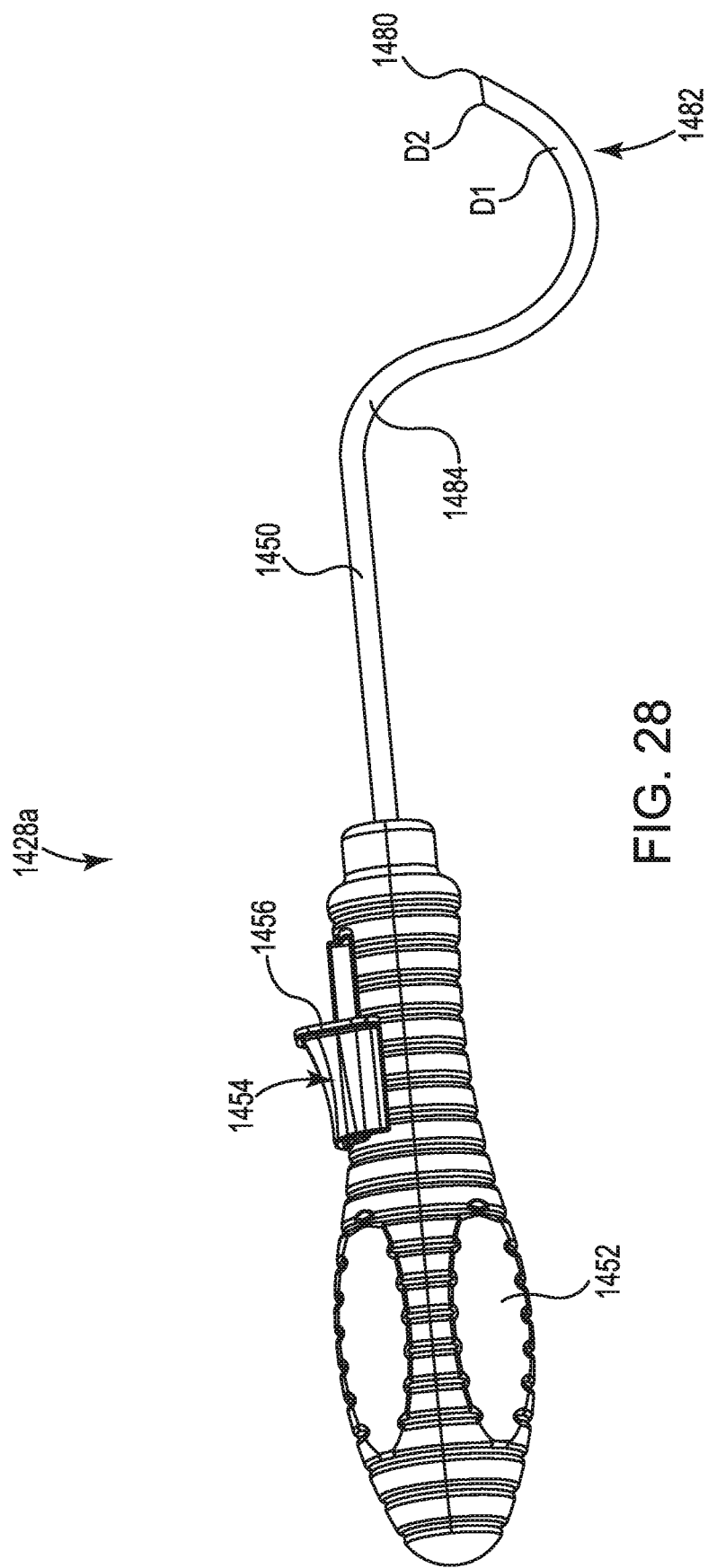
FIG. 28 is a perspective view of one embodiment of the introducer illustrated in FIG. 27.

FIG. 28 is a perspective view of the introducer 1428a. The cannula 1450 extends from the handle 1452 and terminates in an end 1480. The button 1456 of the ejection mechanism 1454 is located on the handle. In one embodiment, the button 1456 is curved in an arc that extends over an exterior portion of the handle 1452, which allows the surgeon to manipulate the button 1456 conveniently and ergonomically with one hand in either a left moving approach or a right moving approach in placing the anchors 1442.

The end 1480 is formed on an end portion 1482 of the cannula 1450. In one embodiment, the end portion 1482 of the cannula 1450 is formed to have a constant outside diameter. In one embodiment, the end portion 1482 of the cannula 1450 is formed to have a tapering outside diameter that tapers from a first diameter D1 to a second diameter D2, where diameter D2 is less than diameter D1.

In one embodiment, the ejection mechanism 1454 includes a wire/rod located inside of the cannula 1450 and connected to the button 1456. Movement of the button 1456 moves the wire/rod within the cannula 1450. When the anchor 1442 is inserted into end 1480 of the cannula 1450, movement of the button 1456 in a distal direction ejects the anchor 1442 in a distal direction out of the cannula 1450.

The cannula 1450 may be straight or curved.

In one embodiment, the end portion 1482 is formed as a circular arc all within the same plane such that the end portion 1482 is neither helical nor spiral.

In one embodiment, the end portion 1482 is formed as a circular arc in a helical spiral. For example, the end portion 1482 extends between a first segment 1484 and the end 1480, and the helical spiral of the end portion 1482 is formed such that the end 1480 is located a distance distal outward and away from the first segment 1484.

Figure 29:
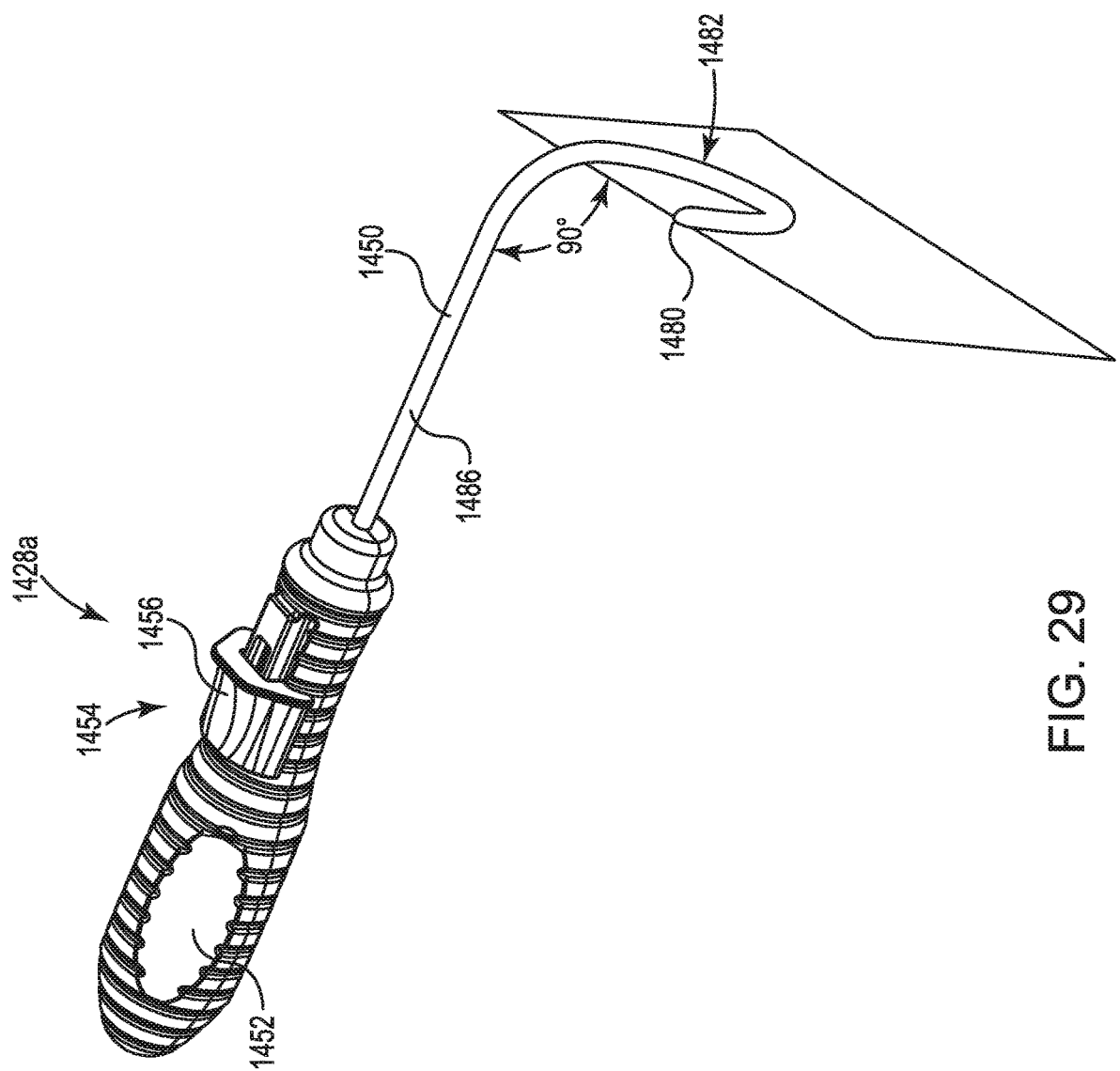
FIG. 29 is a perspective view of the introducer illustrated in FIG. 28.

FIG. 29 is a perspective view of one embodiment of the introducer 1428a where the end portion 1482 is formed as a circular arc within the same plane P. In one embodiment, the end portion 1482 is oriented 90 degrees relative to a straight segment 1486 of the cannula 1450.

Figure 30:
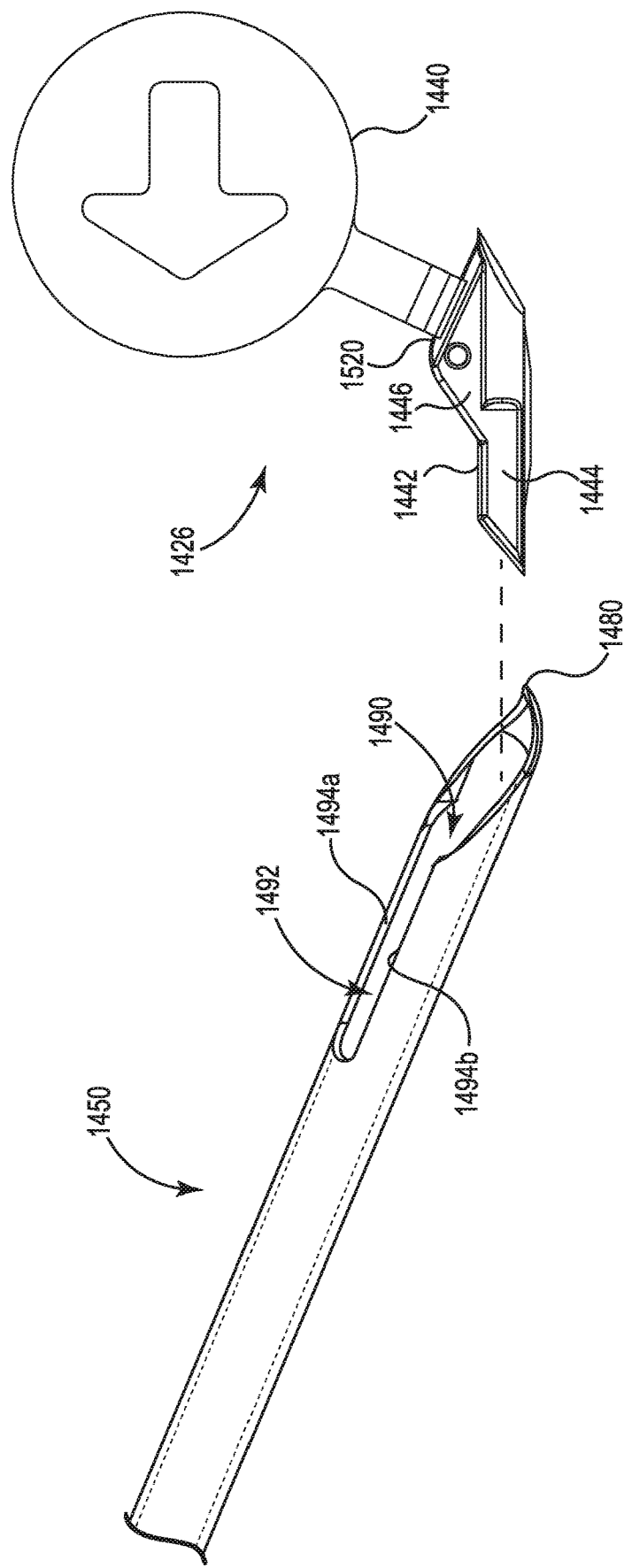
FIG. 30 is a perspective view of an end portion of a cannula of the introducer illustrated in FIG. 28.

FIG. 30 is a perspective view of one embodiment of cannula 1450 prior to inserting the anchor 1442. The cannula 1450 includes a bore 1490 that is sized to receive the body 1444 of the anchor 1442 and a slot 1492 that is sized to receive the tissue engagement fin 1446 of the anchor 1442. In one embodiment, the end 1480 of the cannula 1450 is bent inward toward the bore 1492 to form an ejection ramp that is akin to a ski ramp on a ski jump. In one embodiment, the end 1480 of the cannula 1450 forms a point that is bent inward, where the point is on a side of the cannula 1450 opposite from a location of the slot 1492. The bent end 1480 provides several advantages, including preventing the cannula 1450 from digging into bone when the cannula 1450 is inserted under periosteum tissue and encouraging the anchor 1442 to lift and toggle away from the cannula 1450 when the anchor 1442 is ejected from the cannula 1450. In one embodiment, the bore 1492 is a circular bore having a substantially constant inside diameter. Other geometries are acceptable for the shape of the bore 1492.

In one embodiment, the slot 1492 is provided with side walls 1494a, 1494b that are parallel one relative to the other. The anchor 1442 is relatively small compared to the human hand. The tab 1440 is provided to allow the healthcare worker to handle the anchor 1442 and insert the anchor into the cannula 1450. After the body 1444 of the anchor is inserted into the cannula 1450, the tab 1440 is snapped off from the anchor 1442. The tab 1440 is discarded. The body 1444 of the anchor 1442 is sized to frictionally engage with the bore 1492 and the tissue engagement fin 1446 is sized to frictionally engage with the slot 1492 such that the anchor 1442 does not fall out of the cannula 1450 until actively and intentionally ejected by the surgeon operating the ejection mechanism 54.

It is desirable to frictionally engage the anchor 1442 into the cannula 1450 of the introducer 1428. The geometry of the bore 1492 and the slot 1492 can be modified to encourage the frictional engagement between the cannula 1450 and the anchor 1442.

FIG. 31 is a top view, FIG. 32 is a side view, and FIG. 33 is an end view of one embodiment of a cannula 1451 having a tapered outside diameter and a tapered slot 1492'.

FIG. 31 is a top view of the cannula 1451 having a slot 1492' modified to increase frictional engagement with the anchor 1442 illustrated in FIG. 27. In one embodiment, the slot 1492' is tapered. The slot 1492' is tapered by having the side walls of the slot 1492' tapered at an angle T. In one embodiment, the angle T is 4 degrees and the side walls converge the width of the slot 1492' from 1.1 mm down to 0.890 mm. The tapered slot 1492' ensures positive engagement with the anchor 1442. In this example, the inside diameter of the bore 1492' is 1.6 mm and the outside diameter of the cannula is 2.2 mm.

FIG. 32 is a side view of the cannula 1451, and FIG. 33 is an end view into the bore of the cannula 1451. In one embodiment, the outside diameter of the cannula 1451 is tapered from a first outside diameter OD1 measured at a proximal portion down to a second outside diameter OD2 measured at a distal portion, where the first outside diameter OD1 is larger than the second outside diameter OD2. The pointed end of the cannula 1451 is not bent to provide the ski slope that is provided by the cannula 1450 (FIG. 30).

Figure 34:
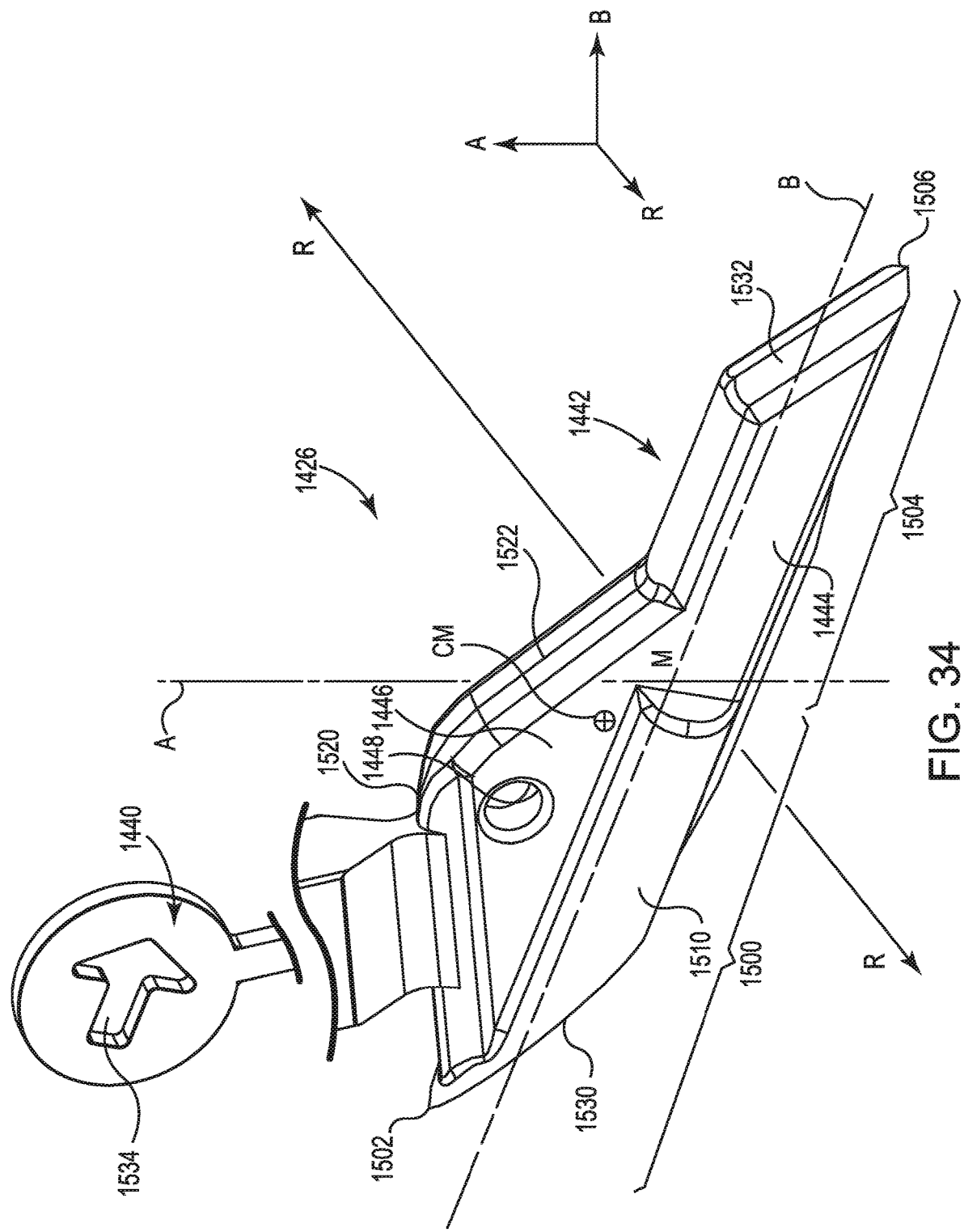
FIG. 34 is a perspective view and FIG. 35 is a side view of one embodiment of the anchor assembly illustrated in FIG. 27.
Figure 35:
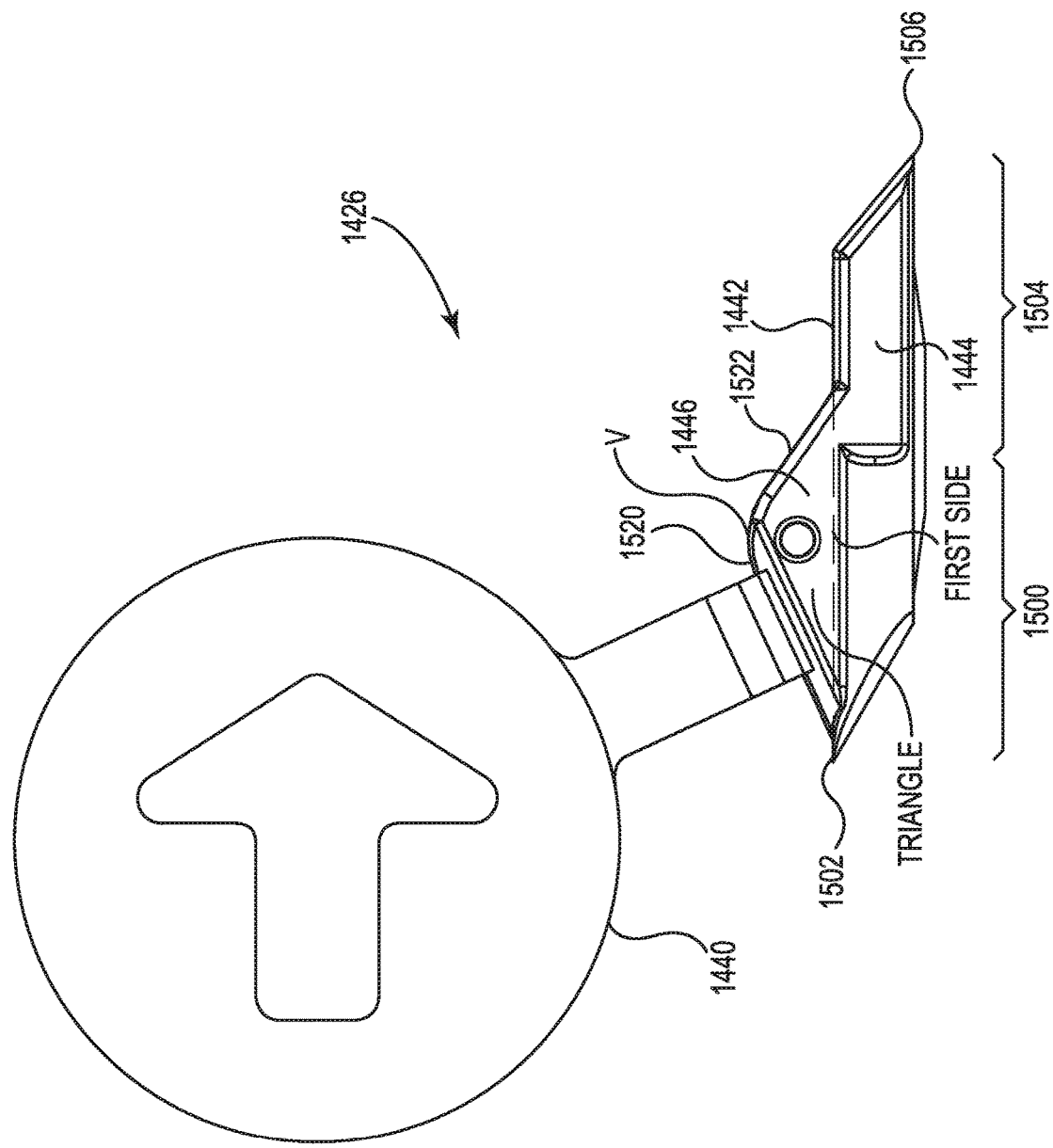

FIG. 34 is a perspective view and FIG. 35 is a side view of the anchor assembly 1426. The anchor 1442 of the anchor assembly 1426 includes a longitudinal midpoint M located in the middle of the length of the anchor 1442 as measured on the longitudinal axis B between ends 1502, 1506. A leading end portion 1500 of the anchor 1442 extends from the midpoint M to a leading end 1502, and a trailing end portion 1504 extending from the midpoint M to a trailing end 1506. The leading end portion 1500 is connected to the trailing end portion 1504 at the midpoint M. A vertical axis A bisects the length of the anchor between the leading end 1502 and the trailing end 1506 and thus intersects the midpoint M.

The anchor 1442 has a geometric asymmetry where the anchor 1442 has more area on the leading end portion 1500 (i.e., the left-hand side of the axis A) then on the trailing end portion 1504 (i.e., the right-hand side of the axis A). The anchor 1442 also has an asymmetric distribution of mass relative to the axis A. In one embodiment, a longitudinal central axis B is drawn and intersects the vertical axis A. In one embodiment, the mass distribution of the anchor 1442 is asymmetric relative to the axis A (i.e., weighted more to the leading end portion 1500) and is also asymmetric relative to the axis B (i.e., weighted more above the axis B). In this example, the center of mass CM is forward of the axis A toward the end 1502 and above the axis B. The center of mass CM of the anchor 1442 is not necessarily located at the geometric midpoint M.

The tissue engagement fin 1446 is located asymmetrically on the anchor 1442 relative to the midpoint M. In one embodiment, the tissue engagement fin 1446 is located along the leading end portion 1500 of the anchor 1442 to provide the anchor 1442 with a geometric asymmetry associated with the leading end portion 1500. In one embodiment, the anchor 1442 includes a barrel 1510 located on the leading end portion of the anchor 1442 to provide the anchor 1442 with an asymmetric mass distribution relative to the midpoint M. The barrel 1510, in combination with the tissue engagement fin 1446, contribute to a distribution of mass for the anchor 1442 that is predominantly distributed forward in the anchor 1442, for example along the leading end portion 1500. The barrel 1510 and the eyelet 1448 provided in the tissue engagement fin 1446, in cooperation with the asymmetric forward-biased mass distribution, allow the anchor 1442 to toggle, or turn, to move to ensure engagement when inserted into tissue.

The tissue engagement fin 1446 includes a leading edge 1520 and a trailing edge 1522, and the anchor 1442 includes a leading surface 1530 located on the leading end portion 1500 and the trailing surface 1532 located on the trailing end portion 1504. In one embodiment, the insertion tab 1440 is removably secured to the leading edge 1520 of the tissue engagement fin 1446. The insertion tab 1440 includes a marker or other indicia 1534 to provide visual guidance to the surgical staff that is useful when loading the anchor assembly 1426 into the cannula 1450 of the introducer 1428 (FIG. 30). After the body 1444 and the barrel 1510 of the anchor 1442 are inserted into the cannula 1450 of the introducer 1428, the insertion tab 1440 is disconnected from (snapped off) from the anchor 1442. The anchor 1442 is retained within the cannula 1450 and prepared for insertion into tissue.

FIG. 35 illustrates one embodiment in which the tissue engaging fin 1446 is triangular with a first side integrated in the leading end portion 1500 of the body 1444, a leading side (e.g., leading edge 1520) connected between the pointed end 1502 and a vertex V, and a trailing side (e.g., trailing edge 1522) connected between the vertex V and the trailing end portion 1504 of the body 1444, with the vertex V located off of the longitudinal axis B.

When the anchor 1442 is inserted into tissue, the surgeon is instructed to provide a pulling force to the suture 1424 (FIG. 27) that is engaged with the eyelet 1448, and this pulling force rotates the anchor 1442 to engage the leading edge 1520, the trailing edge 1522, and the trailing surface 1532 in a stable position within tissue.

The anchor 1442 is both geometrically asymmetric and has an asymmetric mass distribution, both which encourage the anchor 1442 to turn by which the leading end 1502 is rotated in a clockwise (for example) manner to engage the edges 1520, 1522, and surface 1532 with the tissue. The anchor 1442 is configured for insertion into periosteum tissue that covers bone. The bone provides a backstop or a hard surface that prevents the anchor 1442 from penetrating into the bone. The bone, however, also provides a surface that might discourage the rotation or toggle in of the anchor 1442 since the bone is substantially immovable. It has been discovered that the geometric asymmetry and the asymmetric mass distribution of the anchor 1442 is well-suited to allow the anchor 1442 to turn and toggle in a short distance as the surgeon applies a pulling force to the suture that is engaged with the eyelet 1448. Other anchors having a geometric symmetry and a geometric mass distribution have been found to not turn, or turn less slowly and over a greater distance, which can have the effect of the anchor not fully engaging with the tissue and possibly having the anchor pull out of or exit its insertion point into the tissue. In contrast, the anchor 1442 has been discovered to provide rapid turning and toggling that provides excellent tissue engagement over a short engagement distance as the surgeon provides force to the suture 1424 that is engage with the eyelet 1448.

Figure 36:
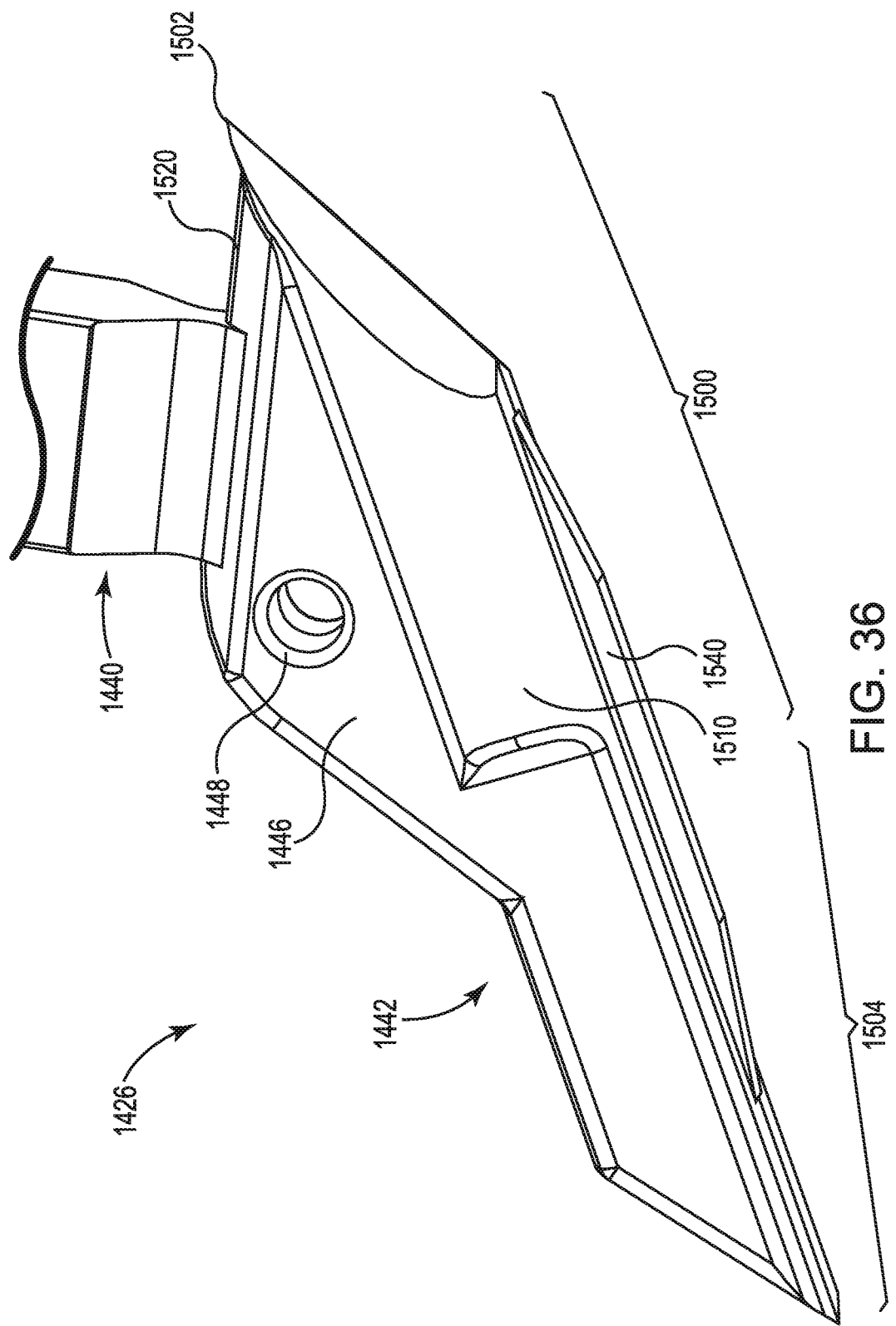
FIG. 36 is a perspective view of one embodiment of the anchor assembly illustrated in FIG. 27.

FIG. 36 is a perspective view of the anchor assembly 1426 oriented to illustrate a crush rib 1540 located along a lower edge of the anchor 1442 on a side opposite from the tissue engagement fin 1446. In one embodiment, the crush rib 1540 extends from the leading end portion 1500 back to the trailing end portion 1504. One suitable height of the crush rib 1540 is in a range from 0.5-4 mm, preferably from 1-3 mm. The crush rib 1540 is provided to ensure a positive frictional engagement of the anchor 1442 with the cannula 1450 (FIG. 27) of the introducer 1428. The crush rib 1540 is deformable and configured to be pressed in toward the body of the anchor 1442 when the anchor 1442 is inserted into a cannula. The crush rib 1540 occupies any excess space inside of the cannula, with the excess material of the crush rib 1540 compacted to fit inside the cannula in a friction-fit manner. The 1-3 mm height of the crush rib 1540 allows the rib to be compacted-to-size as it is inserted into the cannula.

Suitable materials for fabricating the anchor assembly 1426 include polymers in general, metal and metal alloys, composites, composites reinforced with fibers, and other materials suitable for molding or extrusion. In one embodiment, the anchor assembly 1426 is fabricated from polypropylene. Other polyolefins or polymers are suitable.

The anchor 1442 of the anchor assembly 1426 has a length extending from the leading end 1502 to the trailing end 1506 in a range from 2-30 mm, preferably 5-25 mm, and more preferably 10-20 mm. One suitable anchor length has been determined to be about 11 mm from the leading end 1502 to the trailing end 1506.

The exterior surface of the insertion tab 1440 can include a textured gripping surface such as a stippled surface or another suitably structured surface that increases friction when the surgical staff handles the anchor assembly with the gloved hand.

Figure 37:
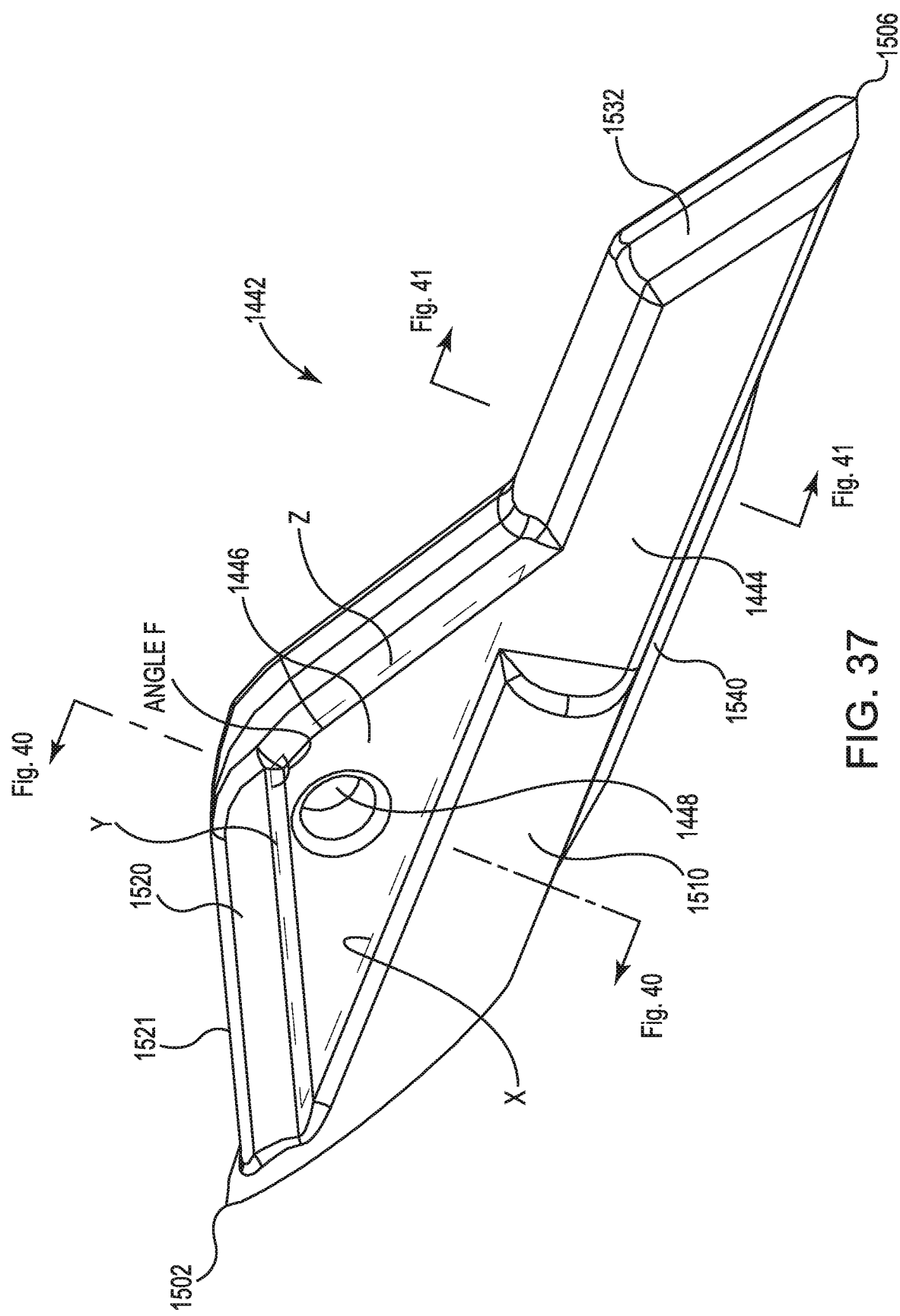
FIG. 37 is a perspective view of one embodiment of an anchor suitable for use with the tissue anchor system illustrated in FIG. 27.
Figure 38:
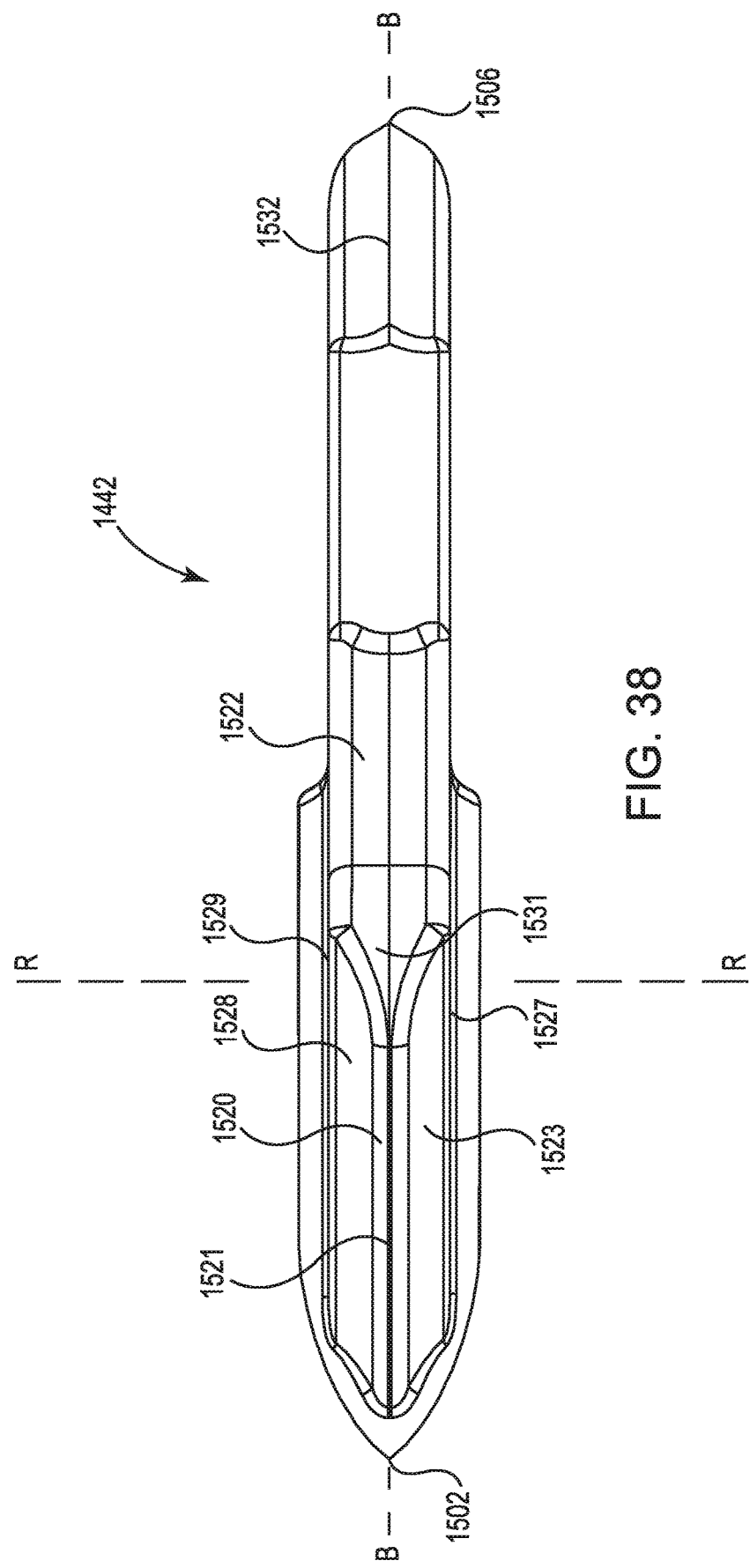
FIG. 38 is a top view and FIG. 39 is a bottom view of the anchor illustrated in FIG. 37.
Figure 39:
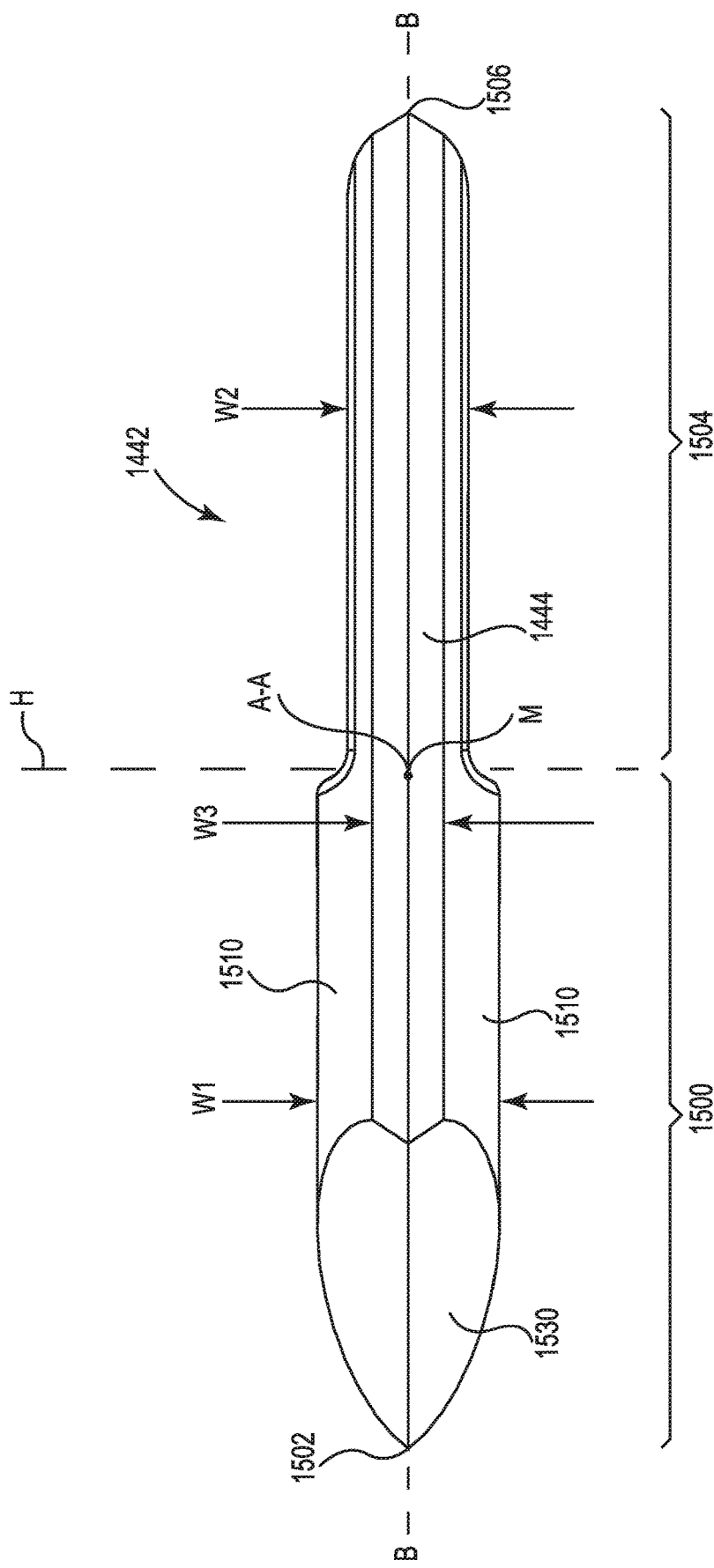

FIG. 37 is a perspective view, FIG. 38 is a top view, and FIG. 39 is a bottom view of the anchor 1442 without the insertion tab 1440. The leading edge 1520 tapers to converge to a line 1521 or narrow surface 1521 that allows the anchor 1442 to more easily penetrate tissue.

The tissue engaging fin 1446 extends away from the body 1444. In one embodiment, the tissue engaging fin 1446 has a triangular shape with a longest side X of the triangle parallel with the longitudinal axis B-B of the anchor 1442, and shorter sides Y and Z meeting at an angle F, the three sides X, Y, Z of the triangle defining a geometry of the tissue engaging fin 1446.

The tissue engaging fin 1446 is configured to grab in tissue and encourage the anchor 1442 to rotate for stabile engagement and anchoring within tissue. One embodiment provides the tissue engaging fin 1446 with a uniform width or thickness. In one embodiment, the interior portions of the triangle X-Y-Z are scalloped or thinned, such that the perimeter of the triangle X-Y-Z is thicker in width than the area inside of the triangle X-Y-Z.

The crush rib 1540 extends longitudinally along a portion of the bottom surface of the anchor 1442. The crush rib 1540 is provided as a radially extending flange, where the flange has a width ranging between 0.1-0.5 mm and a height in a range from 0.5-4 mm, preferably from 1-3 mm. In one embodiment, the crush rib 1540 includes a tapering leading edge and a tapering trailing edge. The crush rib 1540 is useful in retaining the anchor 1442 in the cannula 1450 of the introducer tool 1428 (FIG. 27) until deployment of the anchor 1442 is initiated. The crush rib 1540 is sufficiently deformable when it is engaged with cannula 1450 to allow the anchor 1442 to be press-fit into the cannula 1450 while also allowing the anchor 1442 to be ejected from the tool.

FIG. 38 is a top view of the anchor 1442. The leading edge 1520 tapers to converge to the line 1521 or ridge 1521.

In one embodiment, the leading edge 1520 tapers or slopes from a pinnacle or vertex V of the anchor 1442 towards the body 1444 and the trailing edge 1522 tapers or slopes from the vertex/pinnacle of the anchor 1442 towards the body 1444. In one embodiment, the leading edge 1520 includes sloping surfaces 1523, 1525 extending from the line 1521 toward first and second side surfaces 1527, 1529 of the tissue engaging fin 1446. The line 1521 and the sloping surfaces 1523, 1525 of the leading edge 1520 are configured to facilitate easy cutting or piercing through tissue during insertion and rotation of the anchor 1442 in the tissue. The configuration of the leading edge 1520 including the line 1521 and the sloping surfaces 1523, 1525 provides the leading edge 1520 with a reduced thickness (width) relative to a thickness of the fin 1446 at the first and second side surfaces 1527, 1529, which aids the fin 1446 in sliding through or piercing tissue.

In one embodiment, a top portion 1531 of the tissue engaging fin 1446 has a generally cusped configuration with a base of the cusp located towards the trailing edge 1522 of the fin 1446 and with the two sides of the triangle meeting on the line 1521. The cusped top portion 1531 is configured to help provide a smooth transition of the leading edge 1520 between the line 1521 and the first and second side surfaces 1523, 1525.

In one embodiment, the trailing edge 1522 of the tissue engaging fin 1446 has a blunt configuration and can include a planar surface. The trailing edge 1522 is configured to provide increased engagement with tissue such that the anchor 1442 has improved resistance against extraction from tissue once it is in implanted in position.

With reference to FIG. 39, the surface 1530 of the anchor 1442 is integrated with and angles away from the barrel 1510 to terminate at the leading end 1502. The bottom view of the anchor 1442 illustrates that the leading surface 1530 is heart-shaped as the wider barrel 1510 tapers to the leading end 1502.

In one embodiment, a width W3 of the tissue engaging fin 1446 corresponds to the width W2 of the trailing end portion 1504 of the body 1444. In one embodiment, the width W3 of the tissue engaging fin 1446 is greater along one or more of the sides X, Y, Z of the triangular shape (FIG. 37) than at positions defined within the triangular area. That is to say, in one embodiment a wall thickness of the tissue engaging fin 1446 is thinner "inside" the triangle's bounds than at one or more of the edges of the triangular shape.

In one embodiment, the tissue engaging fin 1446 is superposed over the leading end portion 1500 of the body 1444 including the protruding barrels 1510. The protruding barrels 1510 are formed as a pair of radial barrels 1510 extending from the body 1444 in a radial direction perpendicular to the direction of the fin 1446.

In one embodiment, the tissue engaging fin 1446 is offset towards the leading end 1502 relative to the mid-point M of the body (located on axis A-A in FIG. 34). In one embodiment, the tissue engaging fin 1446 locates asymmetric to the mid-point M. In one embodiment, the tissue engaging fin 1446 is offset such that an entirety of the tissue engaging fin 1446 is located on leading end portion 1500. In one embodiment, a majority but less than an entirety of the tissue engaging fin 1446 locates on leading end portion 1500. In one embodiment, the mid-point M of the body 1444 locates at a transition between the leading end portion 1500 and the trailing end portion 1504. In one embodiment, the eyelet 1448 for receiving a length of suture extends through the entire width W3 of the tissue engaging fin 1446.

Figure 41:
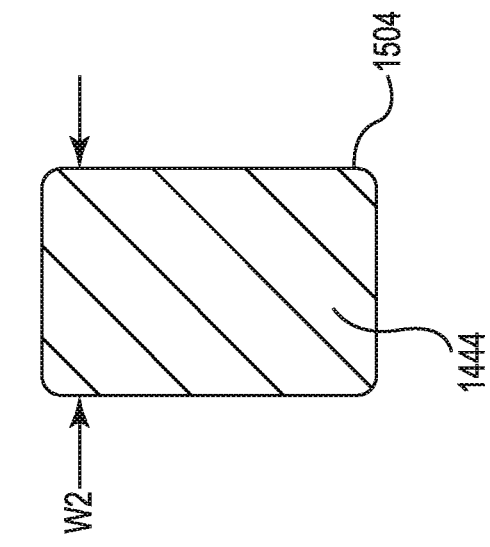
FIG. 40 is cross-sectional view of the leading end portion of the anchor and FIG. 41 is cross-sectional view of the trailing end portion of the anchor.
Figure 40:
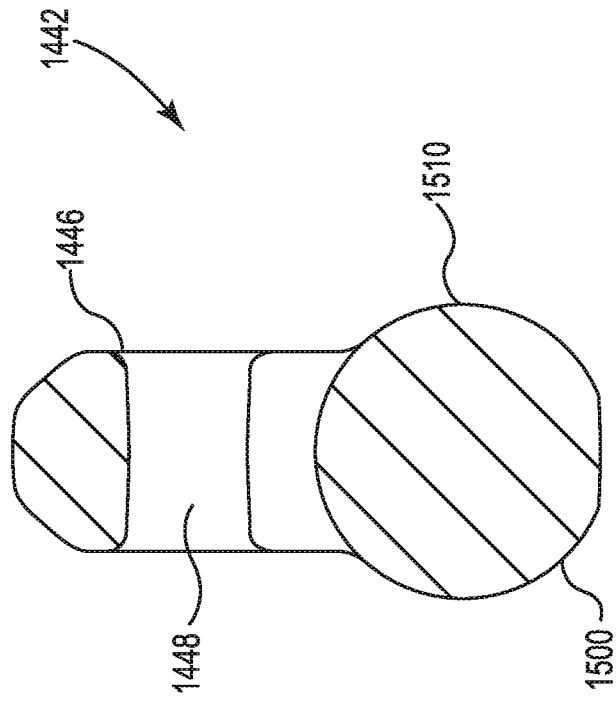

FIG. 40 is cross-sectional view of the leading end portion 1500 of the anchor 1442 and FIG. 41 is cross-sectional view of the trailing end portion 1504 of the anchor 1442.

In one embodiment, the first and second protrusions 1510 combine with the leading end portion 1500 of the body to provide the tissue anchor 1442 with a circular cross-section.

The tissue anchoring system 1420 described above is useful for anchoring support material relative to tissue, particularly in treating urinary incontinence. Embodiments provide placing the anchor 1442 in tissue, which can include ligaments, fatty tissue, connective tissue and other soft tissue in general. It has been discovered that support material useful in treating male urinary incontinence can be implanted through a single (one and only one) incision by employing the introducer 1428 and the anchor 1442 described in this specification in placement of the anchor 1442 into periosteum tissue over the bone of the pelvis and other anchors in the membrane of the transobturator foramen.

Figure 42:
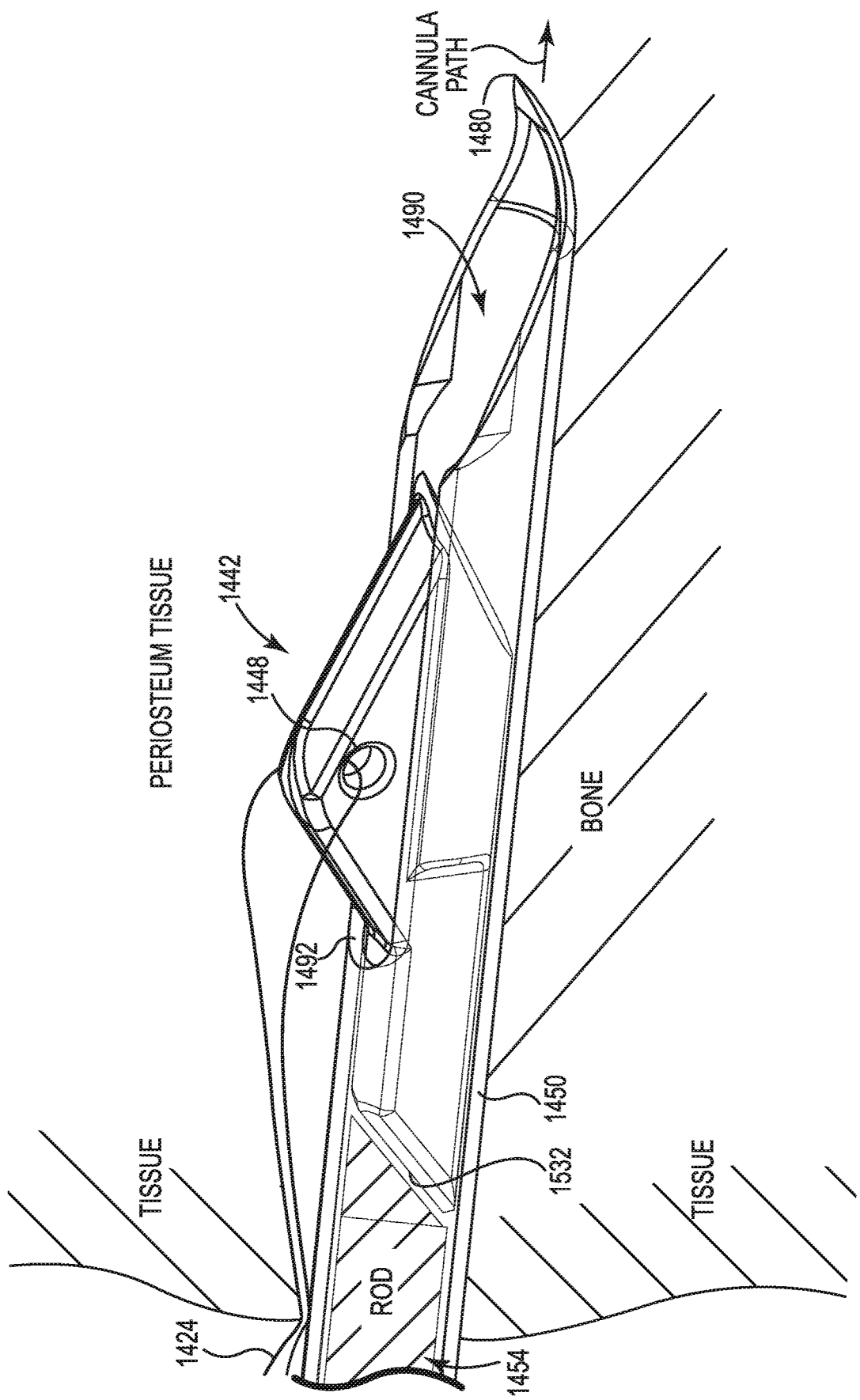
FIGS. 42-43 are perspective views of the anchor illustrated in FIG. 37 ejected into soft tissue from the cannula illustrated in FIG. 30.

FIG. 42 illustrates the cannula 1450 of the introducer 1428 inserted into soft tissue along a cannula path and guided along the bone of the pelvis and into periosteum tissue. Neither the cannula 1450 nor the anchor 1442 enter the bone. The anchor 1442 has been inserted into the bore 1492 and retained in the slot 1492 with the insertion tab 1440 (FIG. 27) removed. The suture 1424 is engaged with the anchor 1442 by the eyelet 1448 and exits through the incision made in the tissue. In this manner, the surgeon has control of the anchor 1442 by placing tension of the suture 1424, and also by having the anchor 1442 frictionally engaged within the cannula 1450. In one embodiment, the end 1480 of the cannula 1450 is bent upward toward the bore 1492 to reduce the possibility of the end 1480 digging into or gouging the bone.

Figure 43:
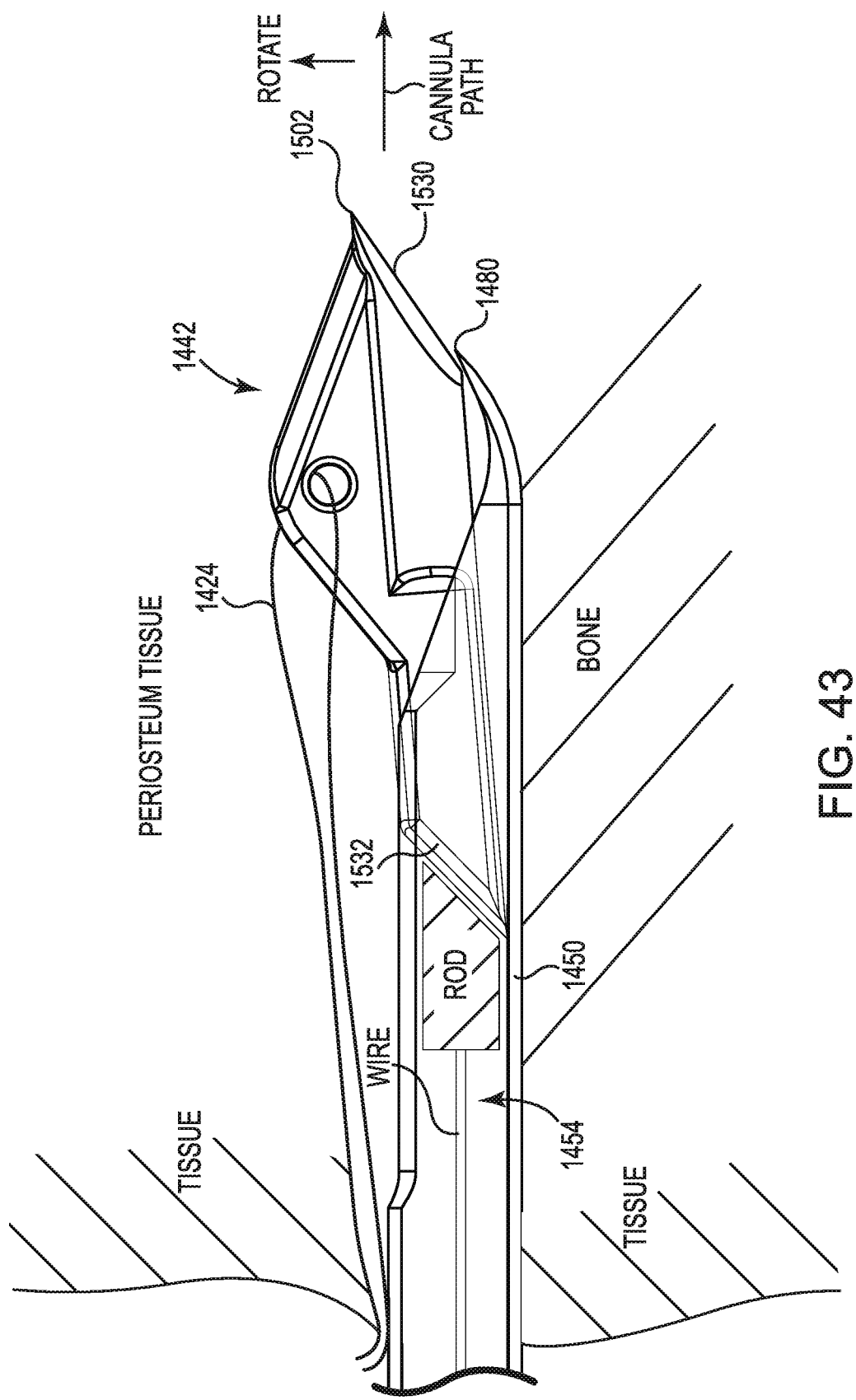

FIG. 43 illustrates the anchor 1442 ejected a partial distance out of the bore 1492 of the cannula 1450 by the ejection mechanism 1454. In one embodiment, the ejection mechanism 1454 is a piano wire connected to the button 1456, where the wire is stiff in axial compression and suited for pushing the anchor 1442 out of the cannula 1450 and yet flexible in a radial direction to allow the wire to negotiate the curvature of the introducer needle or cannula 1450. Suitable ejection mechanisms 1454 include piano wire, braided wires, or flexible cables fabricated of metal or plastic.

With additional reference to FIG. 27, the button 1456 of the ejection mechanism 1454 has been moved forward in a distal direction, which results in the wire pushing the rod forward in a distal direction. A surface of the rod pushes against the trailing edge 1532 of the anchor 1442 to eject the anchor 1442 out of the cannula 1450 and into the soft/ connective tissue. The suture 1424 and the proximal portion of the cannula 1450 extend out of the incision toward the surgeon. The leading end 1502 and the leading surface 1530 of the anchor 1442 are sized and configured to glide between the periosteum tissue and over the bone (but not into the bone surface). The bent end 1480 of the cannula 1450 prevents the cannula 1450 from digging into the bone and lifts the anchor 1442 away from the bone and begins rotation or toggling of the anchor 1442. The bent end 1480 of the cannula 1450 provides a ramp 1480, and movement of the anchor out of the cannula 1450 cause the anchor 1442 to rotate away from the cannula path.

Figure 44:
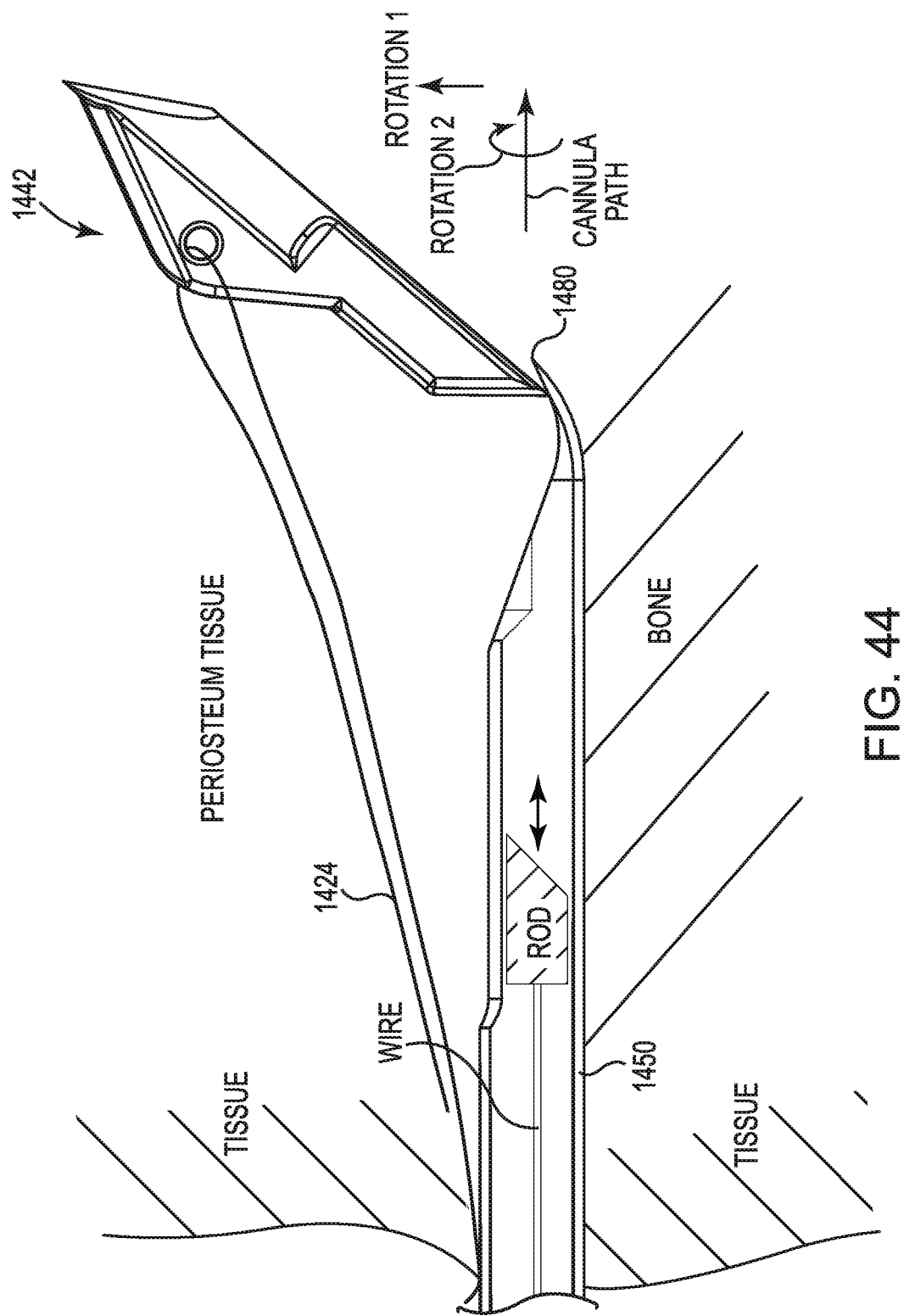
FIGS. 44-46 are schematic views of the anchor illustrated in FIG. 37 rotated into engagement with tissue.

FIG. 44 illustrates the anchor 1442 ejected out of the cannula 1450. The bent tip 1480 directs the anchor 1442 in an upward direction into the periosteum tissue. The anchor 1442 is rotated off of the cannula path (the anchor 1442 is pitched upwards). In one embodiment, the anchor 1442 has two rotational movements: one is rotated/pitched upwards off of the cannula path and the second is rotated (or rolled) on the longitudinal axis of the anchor 1442. The cannula 1450 is removed from the tissue after the anchor 1442 has been ejected. The surgeon controls the orientation of the anchor 1442 by maintaining control of the suture 1424. The additional reference to FIG. 27, the suture 1424 is engaged with the support material 1422 and includes the flattened break pad 1430.

Figure 45:
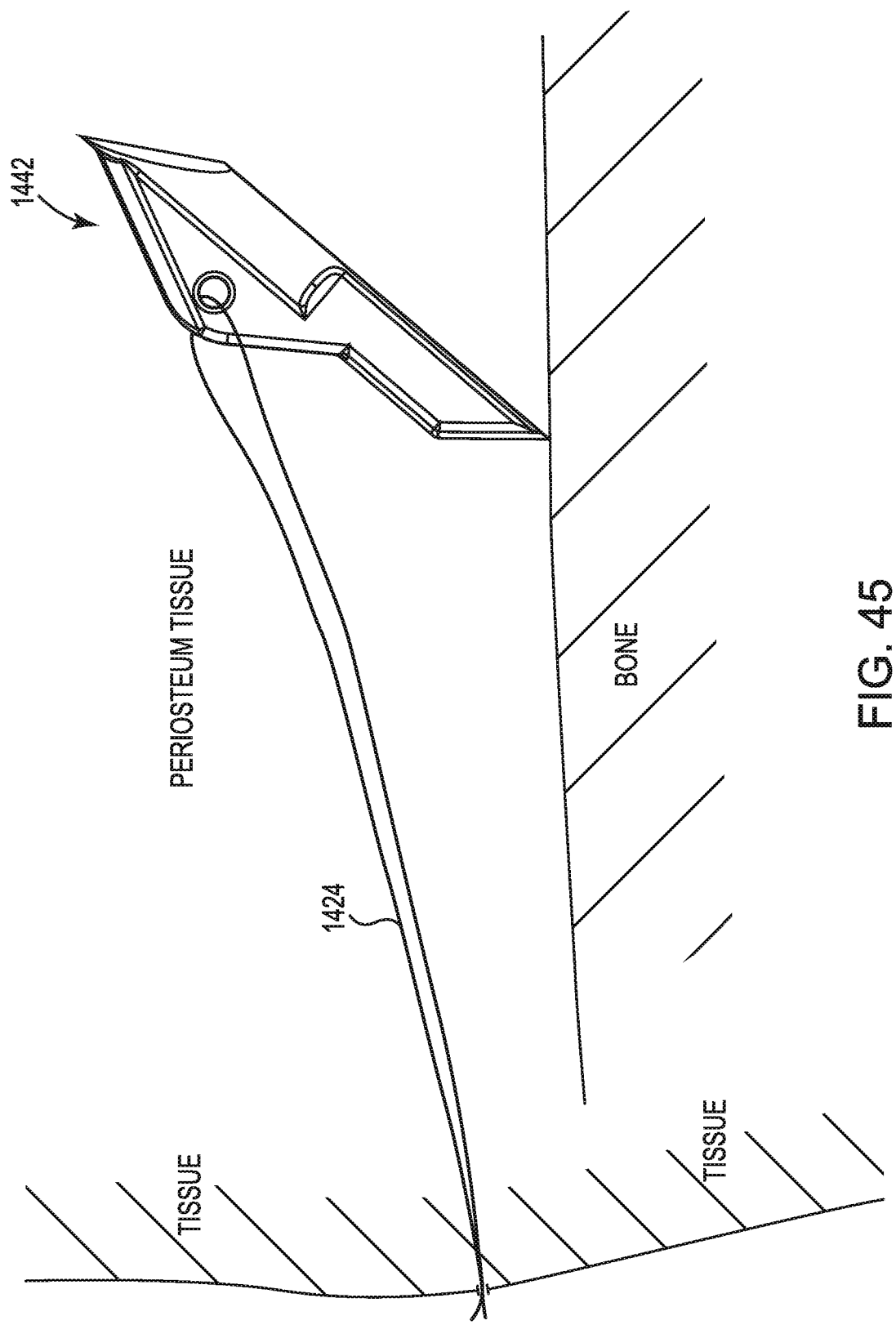

FIG. 45 illustrates the cannula 1450 has been removed from the tissue leaving the anchor 1442 in the periosteum tissue above the bone. The suture 1424 extends away from the anchor 1442 out of the incision by the cannula and back toward the surgeon.

Figure 46:
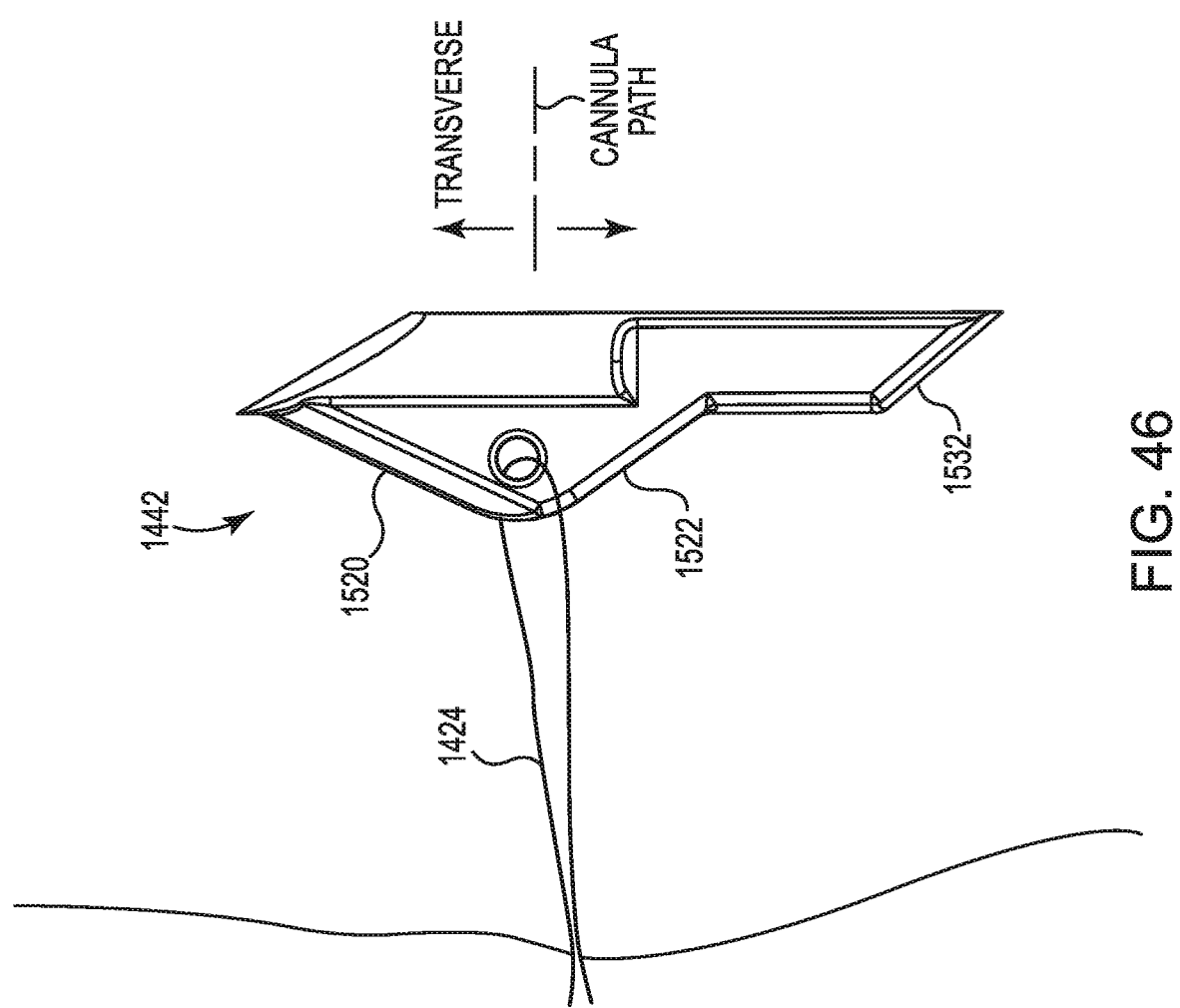

FIG. 46 illustrates a top view of the anchor 1442 in an orientation after a pulling force has been applied to the suture 1424. Pulling on the suture 1424 in a direction away from the patient, rotates the anchor 1442 to position a length of the anchor 1442 transverse to the cannula path. The anchor 1442 is engaged with the periosteum tissue over the surface of the bone; in this sense, the anchor 1442 is between the bone and the surface of the skin, thus located in the periosteum tissue.

The surgeon has directed a pulling forced onto the suture 1424 to rotate the anchor 1442. The geometric asymmetry of the anchor 1442 and the asymmetric mass distribution along the length of the anchor 1442 encourages the anchor to rotate into a stable configuration in which the leading edge 1520, the trailing edge 1522, and the training surface 1532 are engaged with tissue and resist further movement of the anchor toward the opening formed in the skin by the cannula 1450. The surgeon has thus forcefully engage the anchor 1442 in the periosteum tissue into an orientation in which the anchor resists displacement or movement. The suture 1424 extends the anchor 1442 to the support material 1422 (FIG. 27). The anchor 1442 is thus engaged with tissue and the suture 1424 is engaged with the support material 1422. The surgeon has control of the anchor 1442 with the suture 1424, and in preparation for tying a suitable suture knot separates the suture 1424 into two free ends by breaking the break pad 1430. The suture 1424 is tied in a suitable knot to retain the support material 1422 in the location desired by the surgeon.

It has been discovered that the anchor 1442 engages with the periosteum tissue in such a forceful and durable manner that a polypropylene suture 1424, as commonly employed in treating incontinence, will fail and snap before the anchor 1442 disengages with the tissue. That is to say, the polypropylene suture 1424 has been designed to be the weak link in the system 1420 such that the anchor 1442 will forcefully engage with periosteum tissue to allow the surgeon to apply as much force as desired and fixating the support material 1422. The suture 1424 will break before the anchor 1442 can be pulled out of the tissue, which contributes to a superior anchoring connection. The surgeon is familiar with the amount of force that can be applied to polypropylene suture.

The procedure described above places the anchor and the periosteum tissue that covers the pelvis. The system 1420 is suited for placing the anchor 1442 in other locations, for example through the membrane of the obturator foramen. In such a procedure, the cannula is directed through the single incision formed in the patient, around the ischial pubic ramus and into the membrane covering the obturator foramen. One suitable such cannula includes the cannula 1450 described in FIG. 29 having the curved section 82. The ejection mechanism 1454 is employed to deploy the anchor 1442 into the membrane or muscle formed over the obturator foramen. The suture 1424 is employed to fully engage the anchor 1442 in the tissue prior to the surgeon fixating the support material 1422 by tying a knot and the suture 1424.

One suitable method for placing an anchor into tissue includes directing the cannula 1450 of the introducer 1428 into the tissue; pushing the anchor 1442 out of the cannula 1450; removing the cannula 1450 from the tissue and leaving the anchor 1442 in the tissue; applying a pulling force to the suture 1424 that is connected to the anchor 1442 to engage the anchor 1442 with the tissue; breaking the bond that is formed in the suture 1424 at the break pad 1430 to produce two free ends of the suture 1424; and tying a knot in the suture 1424 to fixate the anchor 1442, or the anchor 1442 and the support material 1422, in position as desired by the surgeon and instructed in the instructions for use of the system 1420.

One advantageous embodiment of the system 1420 includes providing the surgeon improved control over when and where the anchor 1442 is placed. For example, it is sometimes experienced that when an anchor is delivered into tissue by an introducer that the tissue has an insufficient ability to retain the anchor. This phenomenon is experienced when the needle is directed into fatty tissue, after which the surgeon realizes that the fatty tissue will be unable to appropriately retain the anchor for treating male incontinence. The system 1420 provides a solution by allowing the surgeon to direct the cannula 1450 into the tissue to determine if the tissue is suited for receiving the anchor, and allowing the surgeon to remove both the cannula 1450 and the anchor 1442 if the surgeon determines the tissue is not ideal for the application. The system 1420 allows the surgeon to direct the cannula at another location in the tissue prior to ejecting the anchor 1442 out of the cannula 1450 with the ejection mechanism 54. The system 1420 provides the surgeon improved control in that the anchor 1442 does not leave the cannula 1450 until the surgeon activates the ejection mechanism 54.

One suitable method of anchoring a support material for treating male urinary incontinence will now be described with reference to FIG. 27. The two anchors 120 are implanted in the muscle of the obturator foramen through the use of the right hand tool 600R and the left hand tool 600L. The base 1460 of the support 1422 is thus suspended by the sutures 110 and the opposing implanted anchors 120. A member of the surgical staff grasps the anchor assembly 1426 by the insertion tab 1440 and inserts the anchor 1442 into the cannula 1450. The insertion tab 1440 is subsequently removed from the anchor 1442. The suture 1424 is engaged with the eyelet 1448 of the anchor 1442 and with the support material 1422. The surgeon directs the cannula 1450 to the periosteum tissue location of interest and ejects the anchor 1442 by activating the button 1456 of the ejection mechanism 54. The surgeon removes the cannula 1450 from the tissue and applies a retraction force to the suture 1424 that rotates and engages the anchor 1442 with the tissue. The support material 1422 is placed in the desired location, the break pad 1430 is separated to provide the suture 1424 with two free ends, and the surgeon fixates a support material 1422 at the desired location. It should be noted that the surgeon also has the option to lightly tie a stay stitch to hold the support material 1422 in place until the other anchors are deployed.

One application of the above method includes forming one and only one incision in the patient between the scrotum and the anus, and fixating the anchors 120 into a respective one of the obturator foramen through the use of one of the introducers 600 (FIG. 11). The base 1460 of the support material 1422 is located inferior to the bulbar urethra and a stay stitch is placed with the suture 110. A similar approach is employed on the contralateral side of the patient to place the anchor 120 in the opposing obturator foramen membrane. The surgeon pulls on the suture 110 to tension and fixate the base 1460 of the support material 1422 at a location inferior to the bulbar urethra.

The pre-pubic arms 1462, 1464 are elevated to a location superior to the base 1460 and a mark is made on the tissue with a marking pen to identify the location of the pre-pubic arms 1462, 1464. It is desirable that the support material 1422 elevates and compresses the tissue of the urethra, and in one embodiment the surgeon will place additional marks on the tissue at a location approximately 1 cm superior to each of the pre-pubic arms 1462, 1464 and 1 cm lateral and outside of each pre-pubic arms 1462, 1464 (i.e., the marks are "up and over" relative to the arms). A suitable cannula is selected, and the anchor 1442c is loaded in the cannula. The cannula is directed into the periosteum tissue and the anchor 1442c is ejected from the cannula into periosteum tissue above the surface of the bone of the pelvis. The cannula is withdrawn and a force is applied to the suture 1424c to toggle and engage the anchor 1442c within the tissue. With the pre-pubic arm 1462 placed in its desired position the surgeon will lightly tie a stay stitch in the suture 1424c. A similar approach will be employed on the contralateral side of the patient in which the anchor 1442d is placed in the periosteum tissue by a cannula of the introducer, after which the cannula is removed and the anchor 1442d is rotated or moved into engagement with the tissue by applying a force to the suture 1424d. The pre-pubic arms 64 will be placed in its desired position according to the instructions for use provided with the system 1420, and the surgeon will tie a permanent knot to fixate the pre-pubic arm 64. The surgeon confirms the location of the placement of the pre-pubic arm 1462, loosens the stay stitch in suture 1424c, and ties a permanent knot in the suture 1424c to fixate the pre-pubic arm 1462. In this manner, the pre-pubic arms 1462, 1464 are separated away from the base 1460 and fixated to elevate and compress the support material 1422 against the urethra. If desired by the surgeon, the plication mechanism 1470 is adjusted to remove slack from a central region of the support material 1422 after the base 1460 and the pre-pubic arms 1462, 1464 have been secured to tissue. The one and only one incision is closed in a suitable manner desired by the physician and the patient begins recovery.

FIGS. 47A-47J are schematic views of embodiments of a process for implanting the tissue anchor system 1420 illustrated in FIG. 27 in a person to treat urinary incontinence.

In preparation for the surgery, the patient is reclined in a lithotomy position, the sterile field is defined with appropriate draping, and the skin of the patient is suitably prepped according to the guidelines of the healthcare facility. The packaging containing the tissue anchor system 1420 is opened and the instructions for use are made available, for example on a back table in the surgical suite.

The tool 600 is employed to implant the anchors 120 in tissue of the obturator foramen and the introducer 1428 is employed to place each of the anchors 1442 into tissue of the patient, and these procedures are accessed through a single incision. The single incision is the one and only one incision formed in the skin of the patient. One useful incision is a midline incision formed between the scrotum and the anus of a male patient to provide axis to the bulbar urethral complex. Some surgeons dissect the bulbous spongiosis muscle to access the urethra and the system 1420 is appropriate for this approach. Other surgeons do not dissect the bulbous spongiosis muscle, but rather access the urethra complex and the system 1420 is also appropriate for this approach. A dilator or retractor of some sort is typically used to force the incision to an expanded position that provides access to the pelvic triangle. The dilator is not illustrated, but the incision is illustrated as an expanded circumferential area.

Figure 47A:
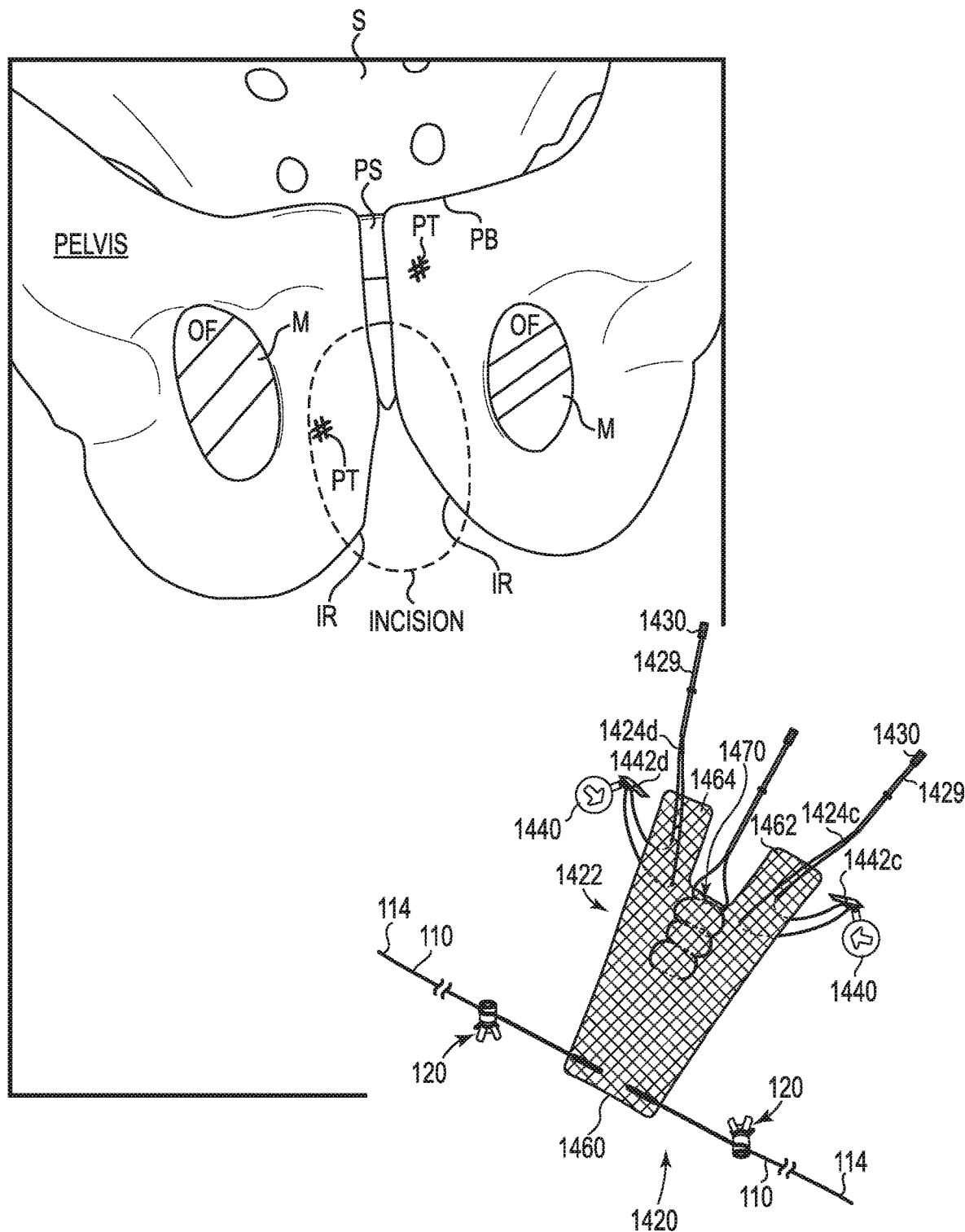
FIGS. 47A-47J are schematic views of embodiments of a process for implanting the tissue anchor system illustrated in FIG. 27 in a person to treat urinary incontinence.

FIG. 47A is a schematic view of the support 1422 located in the surgical field and ready for placement within the patient. The adjustable anchors 120 will be placed in each of the opposing obturator foramen and the tension in the sutures 110 adjusted, and then the anchors 1442 will be placed in periosteum tissue over the pelvis on each side of the pubic symphysis and the associated sutures 1424 will be adjusted and terminated. One or more of the adjustable anchors 120 could be replaced with the fixed anchor 136 described above.

The following procedure will place the anchors 120 associated with the base 1460 of the support 1422 in separate opposing obturator foramen (OF) of the patient. The anchor 120 is inserted in the patient's right side OF and the suture 110 is allowed to trail out of the incision. The other anchor 120 is inserted in the patient's left side OF and the suture 110 is also allowed to trail out of the incision. The support 1422 is positioned and the surgeon pulls on each of the sutures 110 to apply tension through to the support 1422, where the tension is transmitted through the implanted anchors 120. The suture 110 is slid through the anchor 120. The support 1442 is placed under increased tension when the effective length of the supporting suture 110 between the support 1442 and the anchor 120 is shortened. The anchor 120 allows for bi-directional adjustment, and the support 1442 can be loosened (the tension decreased) be lengthening the effective length of the supporting suture 110 between the support 1442 and the anchor 120. Thus, the base 1460 of the support 1422 is suspended by the sutures 120 implanted in the muscle of the OF. The anchors 1442c, 42d attached to the pre-pubic arms of the support 1422 are subsequently attached to tissue of the periosteum, and each suture 1424c, 24d is secured after both anchors 1442c, 42d are implanted, as described below.

Figure 47B:
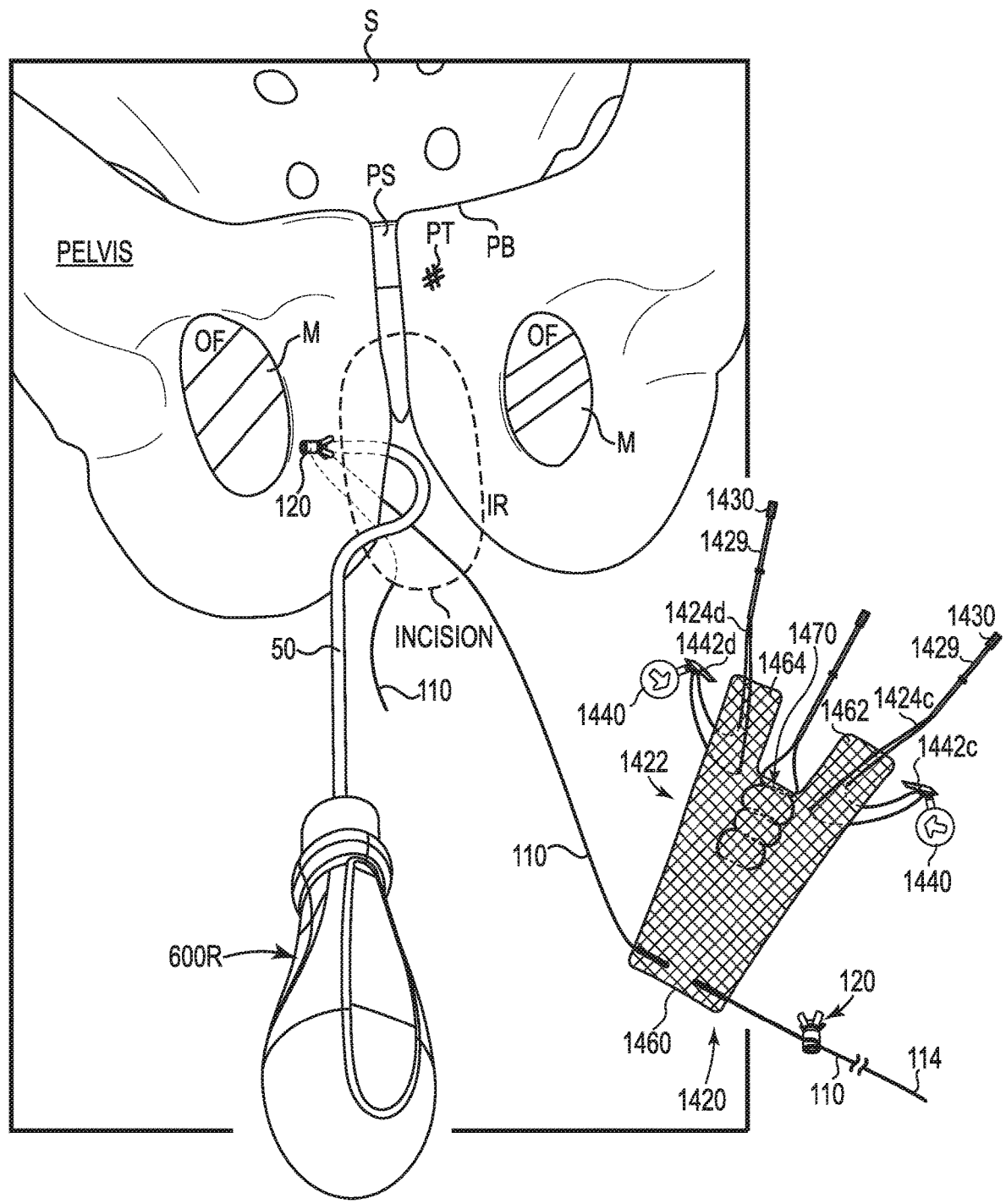

FIG. 47B is a schematic view of the right side introducer 600R (relative to the patient) inserted through the incision and directed on a path around the descending ischial pubic ramus (or, ischial ramus IR). The anchor 120 is inserted onto the post at the end of the tool 600R. The end of the tool 600R and the anchor 120 follow a path from the incision, around the IR and penetrates the membrane M of the obturator foramen OF to a location of the obturator internus muscle. An audible "pop" can at times be heard as the anchor 120 enters the muscle of the OF. The tool 600R is removed from the incision leaving the anchor 120 in the obturator internus muscle. The surgeon applies a force to the suture 110, and the suture slides relative to the anchor 120 to position the support 1422. Additional tensioning is applied based on the surgeon preference.

Figure 47C:
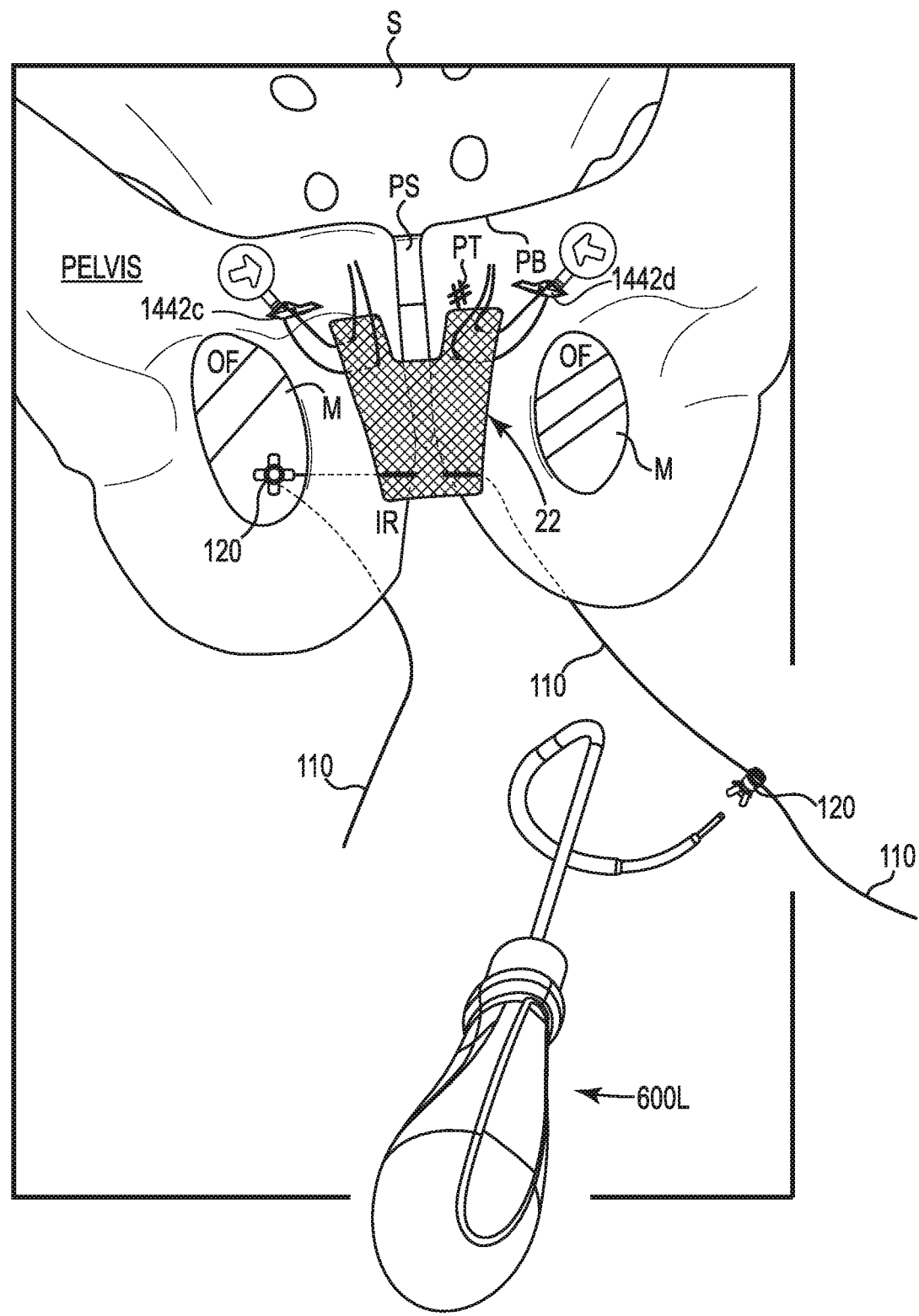

FIG. 47C is a schematic view illustrating the base 1460 of the support 1422 located in one desirable position with the second anchor 120 being loaded onto the left-hand tool 600L. The anchor 120 will be inserted on the patient's left hand side using the tool 600L that is provided with a curvature that is opposite from the curvature of tool 600R (the right side introducer).

Figure 47D:
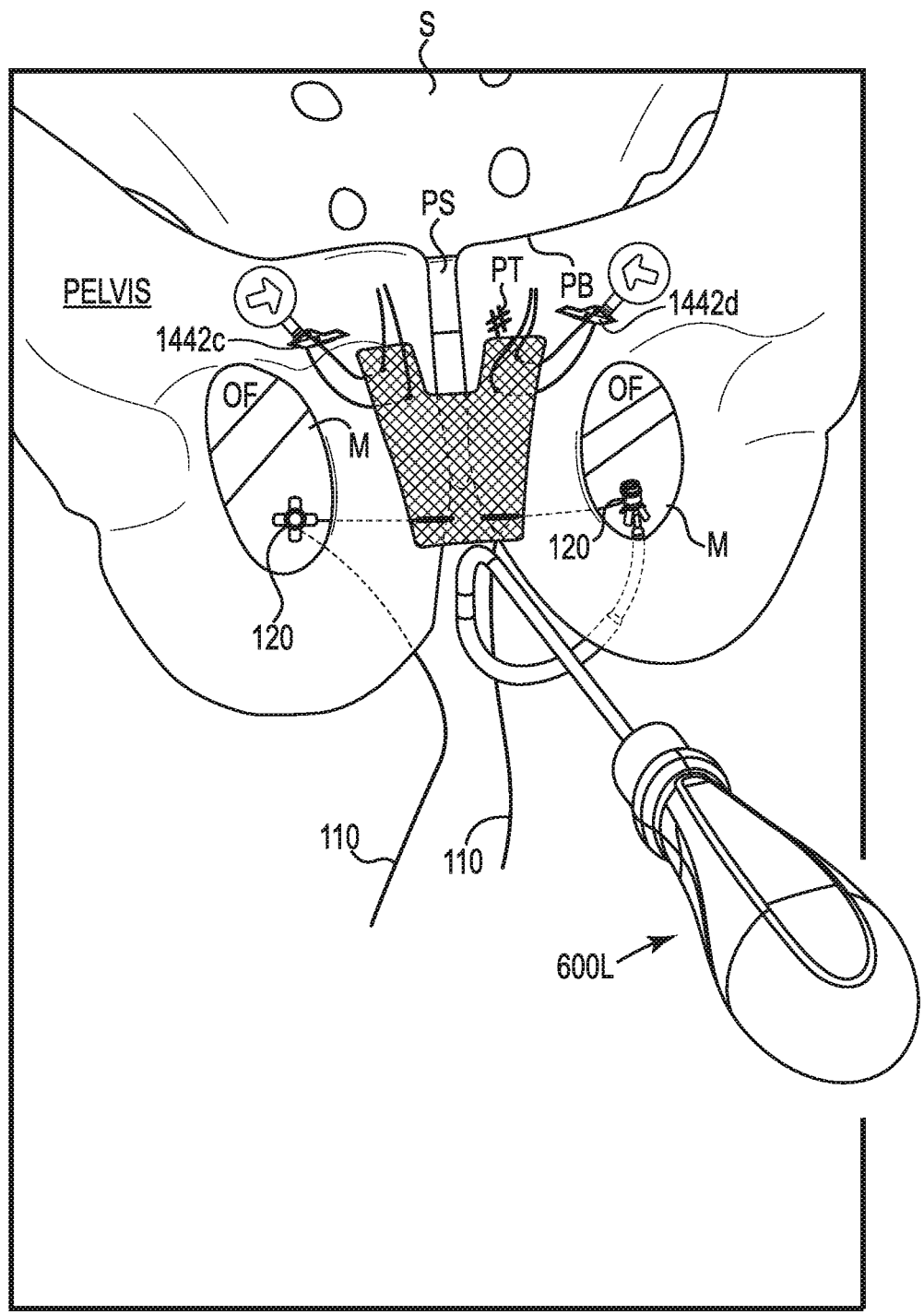

FIG. 47D is a schematic view of the left side tool 600L inserted through the incision, around the descending IR, and through the membrane M covering the obturator foramen OF. The anchor 120 is "popped" into the obturator internus muscle. The tool 600L is removed. The surgeon pulls on the suture 110 to apply a desired level of tension to the support 1422.

Figure 47E:
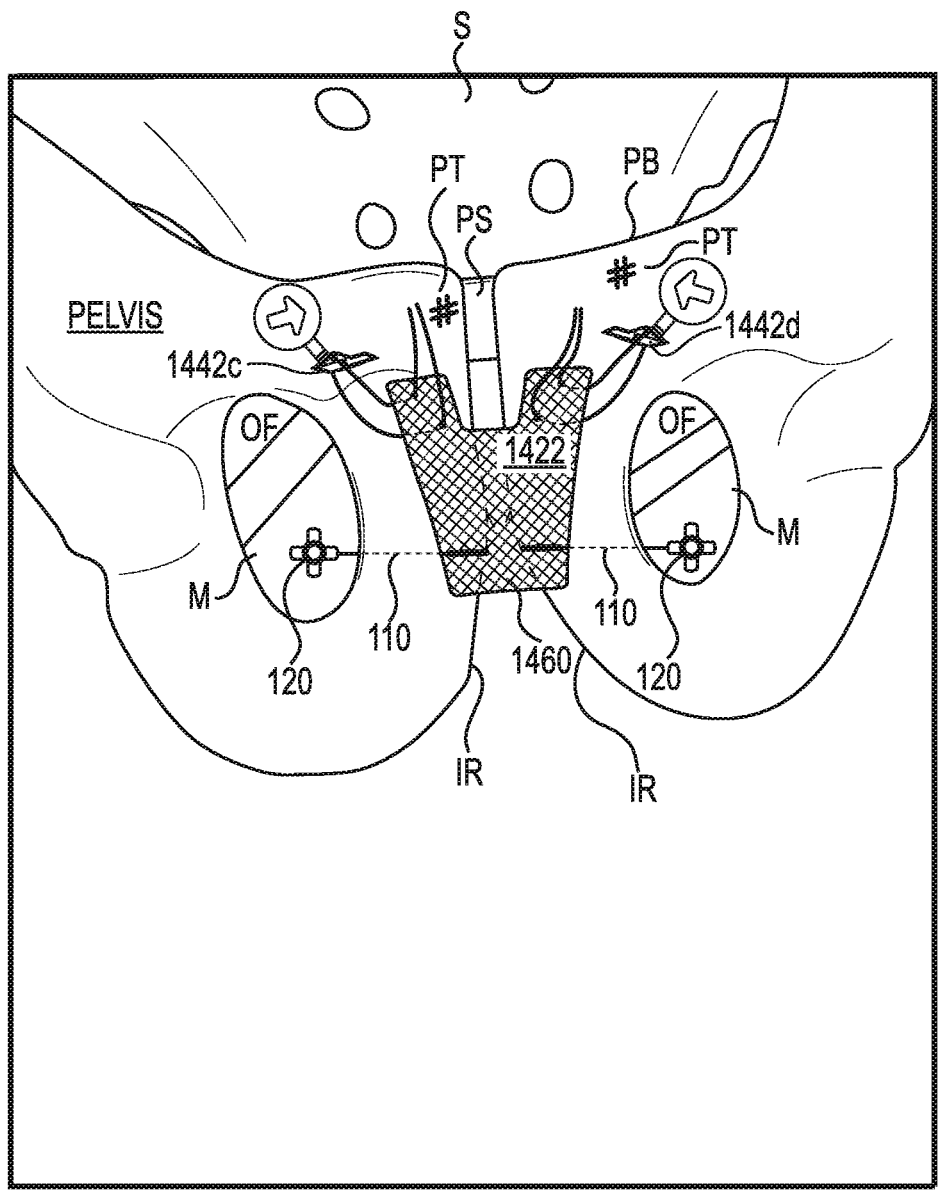

FIG. 47E is a schematic view of the support 1422 located behind the incision with the base 1460 maintained in a lateral orientation between the opposing obturator foramen OF. The surgeon locates a desired orientation for the base 1460 and suitably adjusts the sutures 110. In this way, the base 1460 is suspended between the sutures 110 and a respective one of the anchors 120. The pre-pubic arms 1462, 1464 are elevated to either side of the pubic symphysis PS.

Figure 47F:
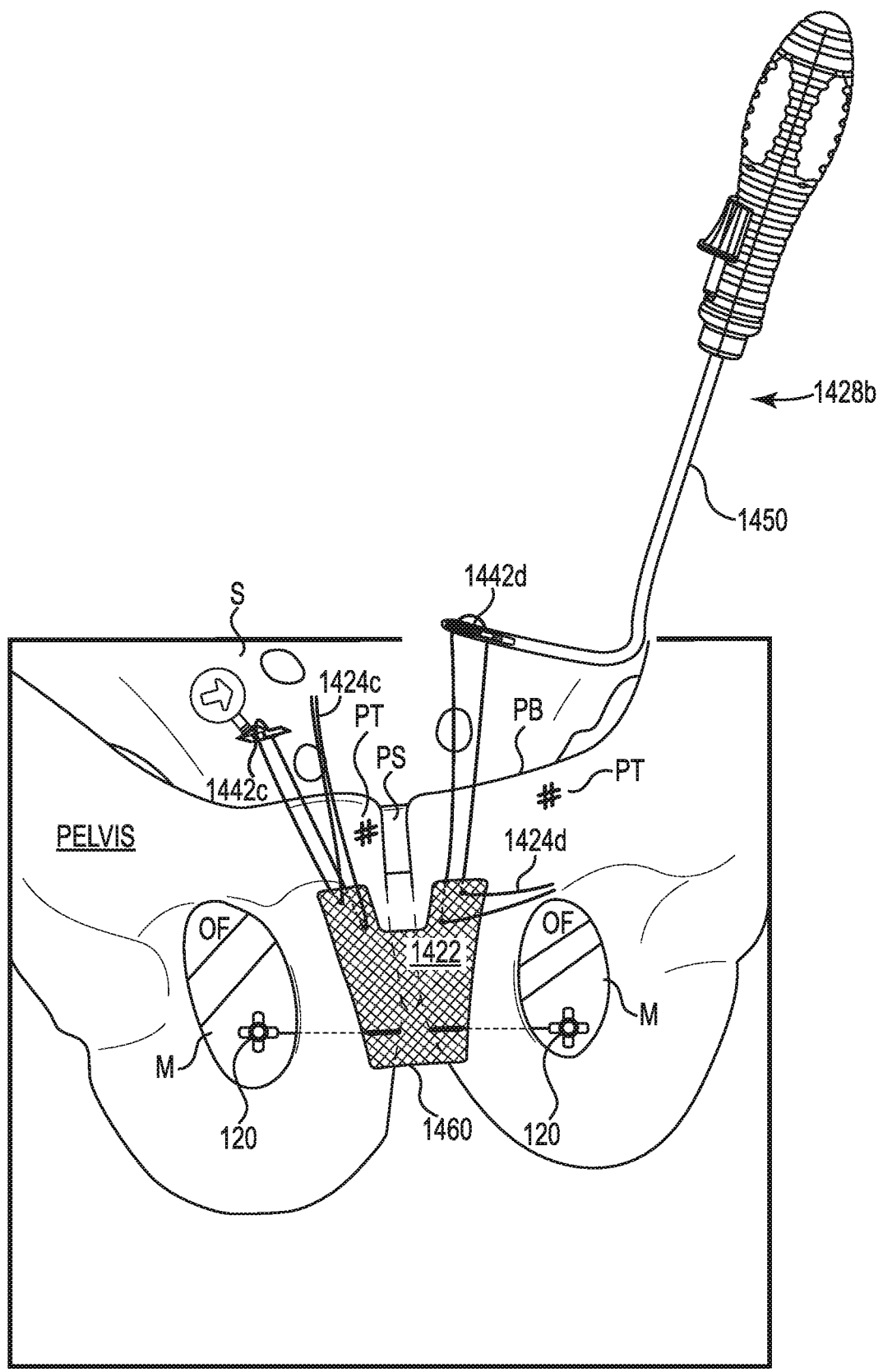

FIG. 47F is a schematic view of the anchor 1442d loaded into the cannula 1450 of the left side introducer 1428b. The insertion tab 1440 has been removed and discarded. The procedure allows for placement of the pre-pubic arm anchors 1442c, 42d with either the right side introducer 1428a or the left side introducer 1428b, as determined by the preference of the surgeon.

Figure 47G:
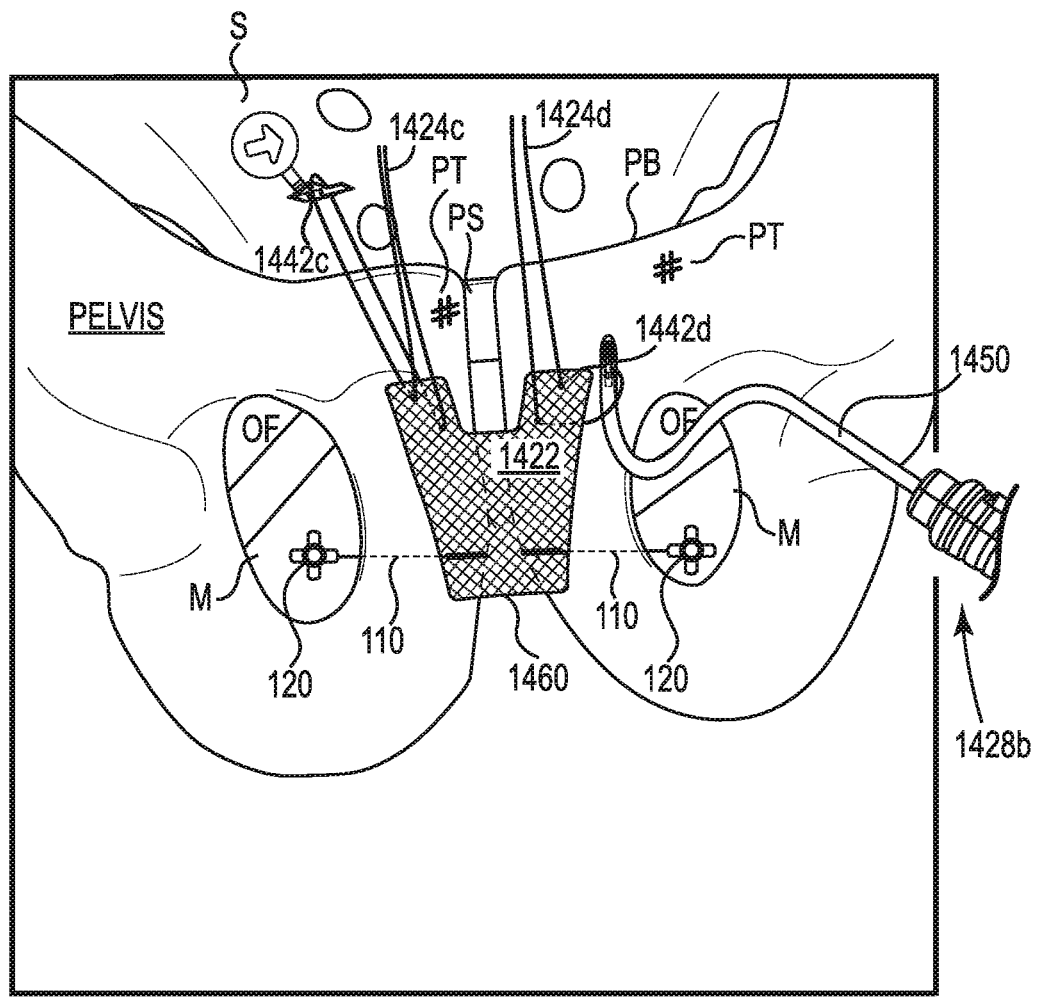

FIG. 47G is a schematic view of the introducer 1428d inserted through the incision to attach the pre-pubic arm 1462 to the left-hand side of the patient. The end 1480 of the cannula 1450 is inserted through the periosteum tissue PT. The end 1480 of the cannula 1450 is bent/sloped or otherwise configured to allow the tip of the introducer to slide along the bone and avoid digging into the bone under the periosteum tissue PT. The button 1456 is manipulated to eject the anchor 1442d out of the cannula and under the periosteum tissue PT and on top of the bone. The introducer 1428b is removed from the incision. The surgeon applies a pulling force to the suture 1424 that is connected the anchor 1442d, and this force toggles and rotates the anchor 1442d into a broadside-on position that fully engages the anchor 1442d with the periosteum tissue PT. The suture 1424d extends from the implanted anchor 1442d, through the pre-pubic arm of the support 1422, and out of the incision for subsequent fixation.

Regarding one process of anchoring the anchor to tissue, and as the steps are illustrated in FIG. 47G, another anchor is inserted into the bore of the same cannula 28b that was employed in placing an anchor into the tissue of the obturator foramen, and this other anchor is inserted in the cannula and into the incision and along a second cannula path into periosteum tissue. This other anchor is ejected out of the bore of the cannula and into the periosteum tissue. The other suture attached to the other anchor is pulled in a direction away from the patient to rotate the other anchor to position a length of the anchor transverse to the second cannula path. The other continuous suture loop is broken to allow a knot to be tied to fixate the support over the periosteum tissue.

Figure 47H:
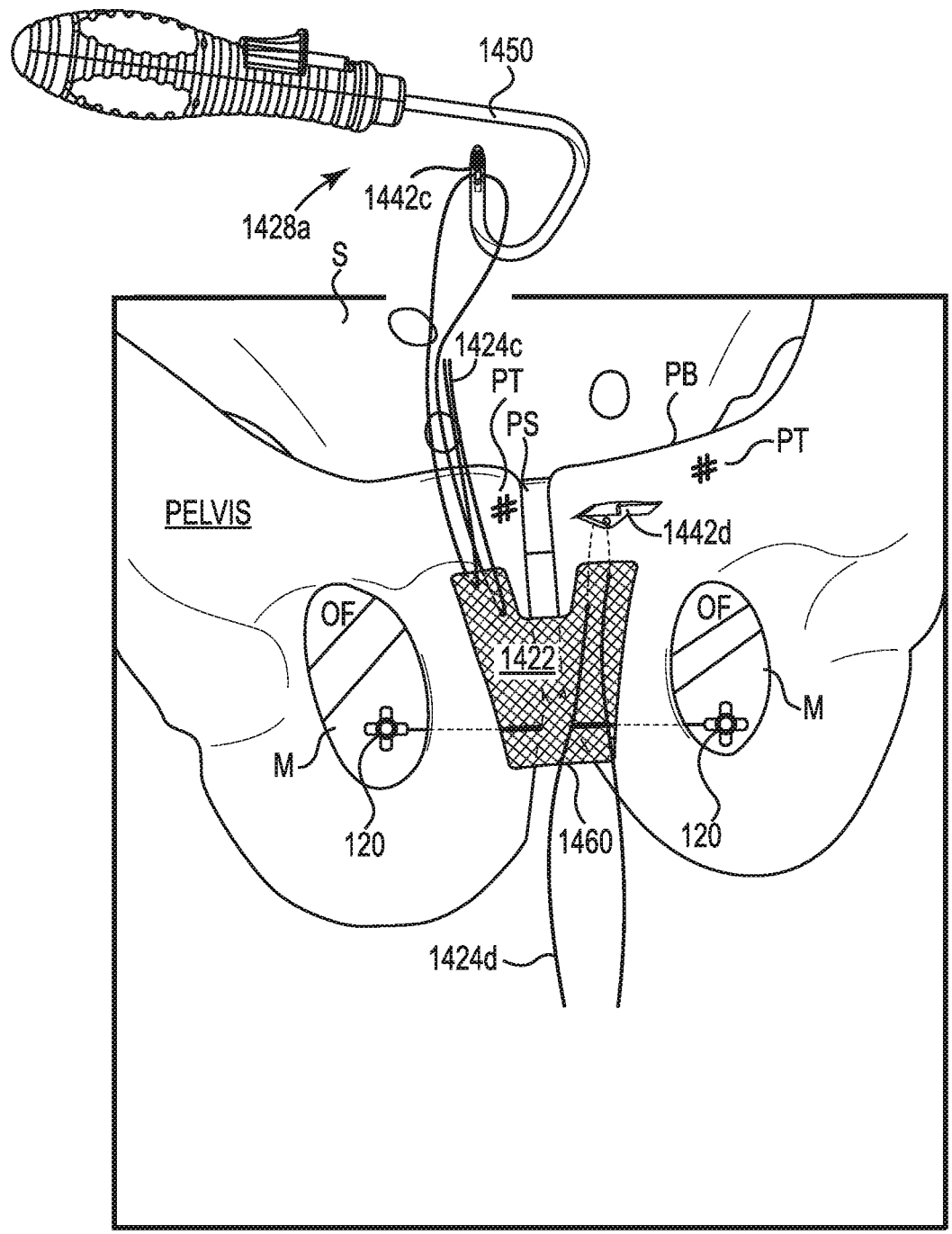

FIG. 47H is a schematic view of the base 1460 of the support 1422 suspended between the obturator foramen OF with the pre-pubic arm 1462 secured to the periosteum tissue PT on the left-hand side of the patient by the anchor 1442d. A fourth anchor 1442c is inserted into the cannula 1450 of, in this instance, the introducer 1428a. Again, the insertion tab 1440 has been removed from the anchor 1442c and discarded.

Figure 47I:
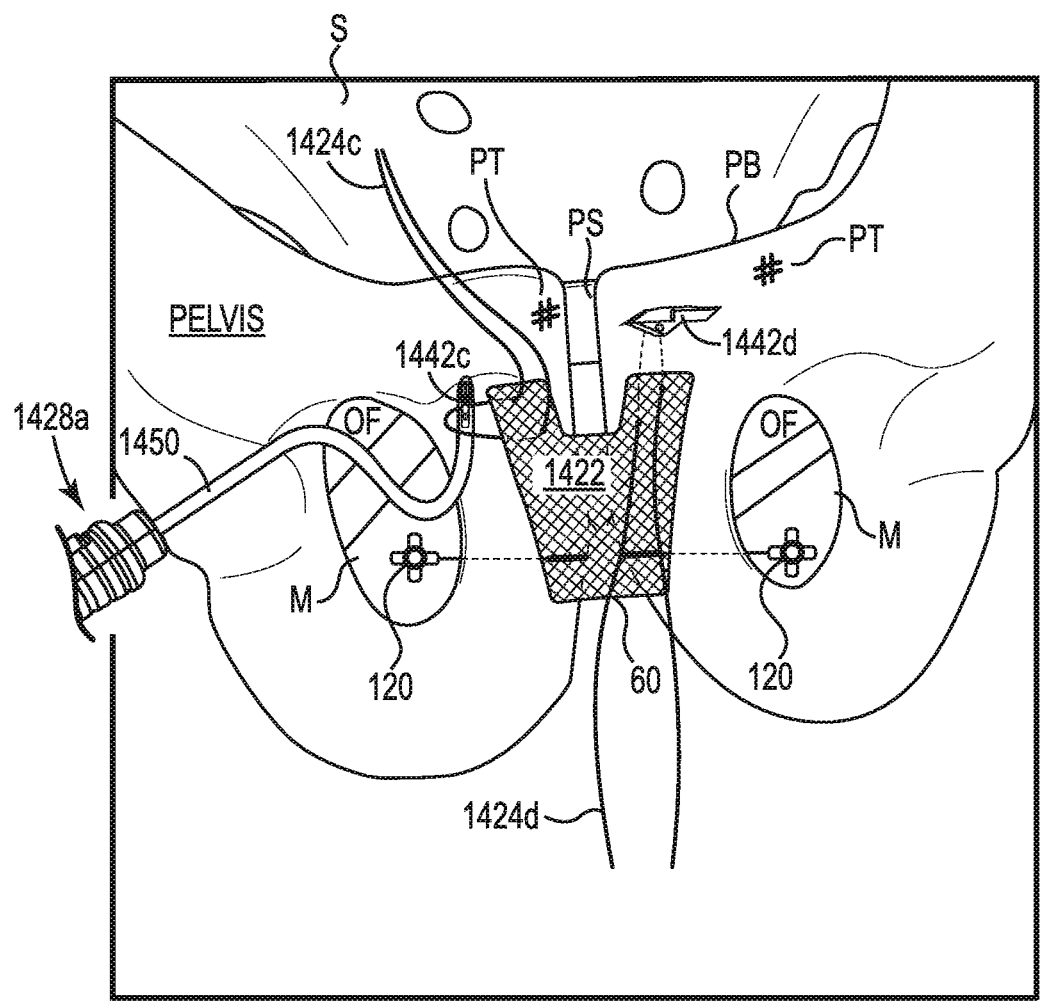

FIG. 47I is a schematic view of the introducer 1428a inserted through the incision to fixate the pre-pubic arm 1464 on the right-hand side of the patient. The end 1480 of the cannula 1450 is directed through the periosteum tissue PT. The end 1480 of the cannula 1450 will slide along the surface of the bone. When suitably placed between the periosteum tissue PT and the bone, the button 1456 is pushed forward to eject the anchor 1442c out of the cannula 1450. The introducer 1428b is removed from the incision. The surgeon applies a tension to the suture 1424 to toggle, rotate, and engage the anchor 1442c within the periosteum tissue PT. At this point in the process, two anchors 1442d, 1442c are attached in the two pre-pubic arms and the associated sutures 1424d, 1424c extend from the anchors 1442d, 1442c freely out of the incision.

The surgeon elevates both of the pre-pubic arms 1462, 1464 in tension against the fixed base 1460 and terminates the sutures 1424d, 1424c.

Figure 47J:
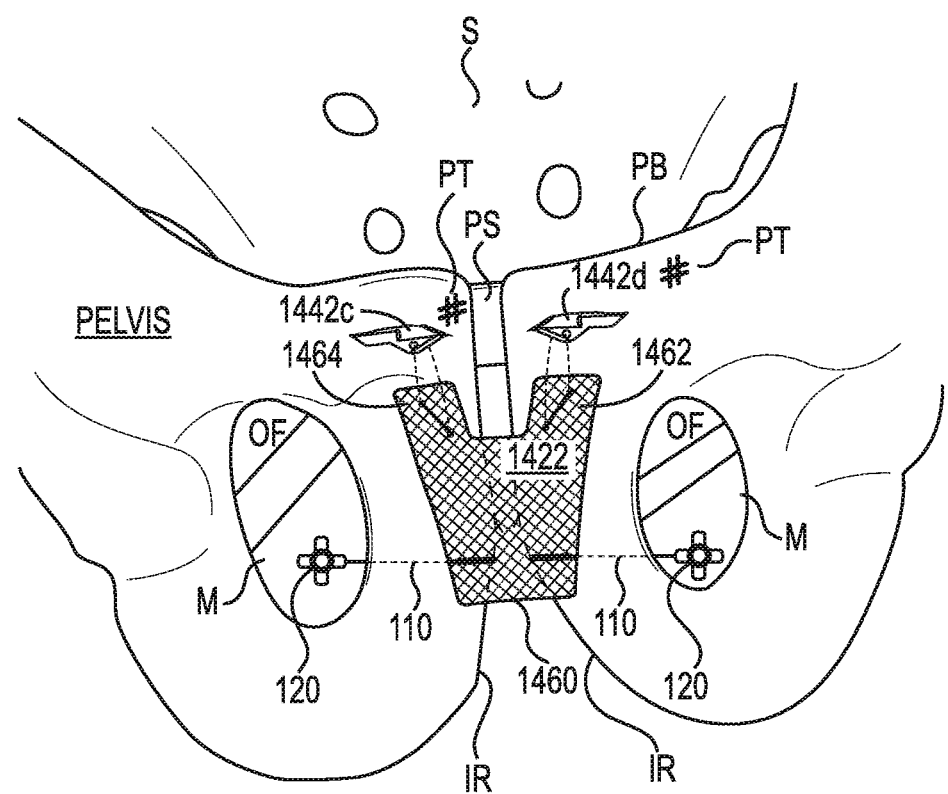

FIG. 47J is a schematic view of the support 1422 suspended between the obturator foramen OF and the anchors 120 and fixated to the periosteum tissue PT by anchors 1442c, 42d. The support 1422 has been implanted through a single (one and only one) incision. The implanted anchors 1442 combine with the sutures 1424 to hold the support 1422 in place and to elevate and compress the bulbar urethral complex in treating male urinary incontinence.

Figure 48:
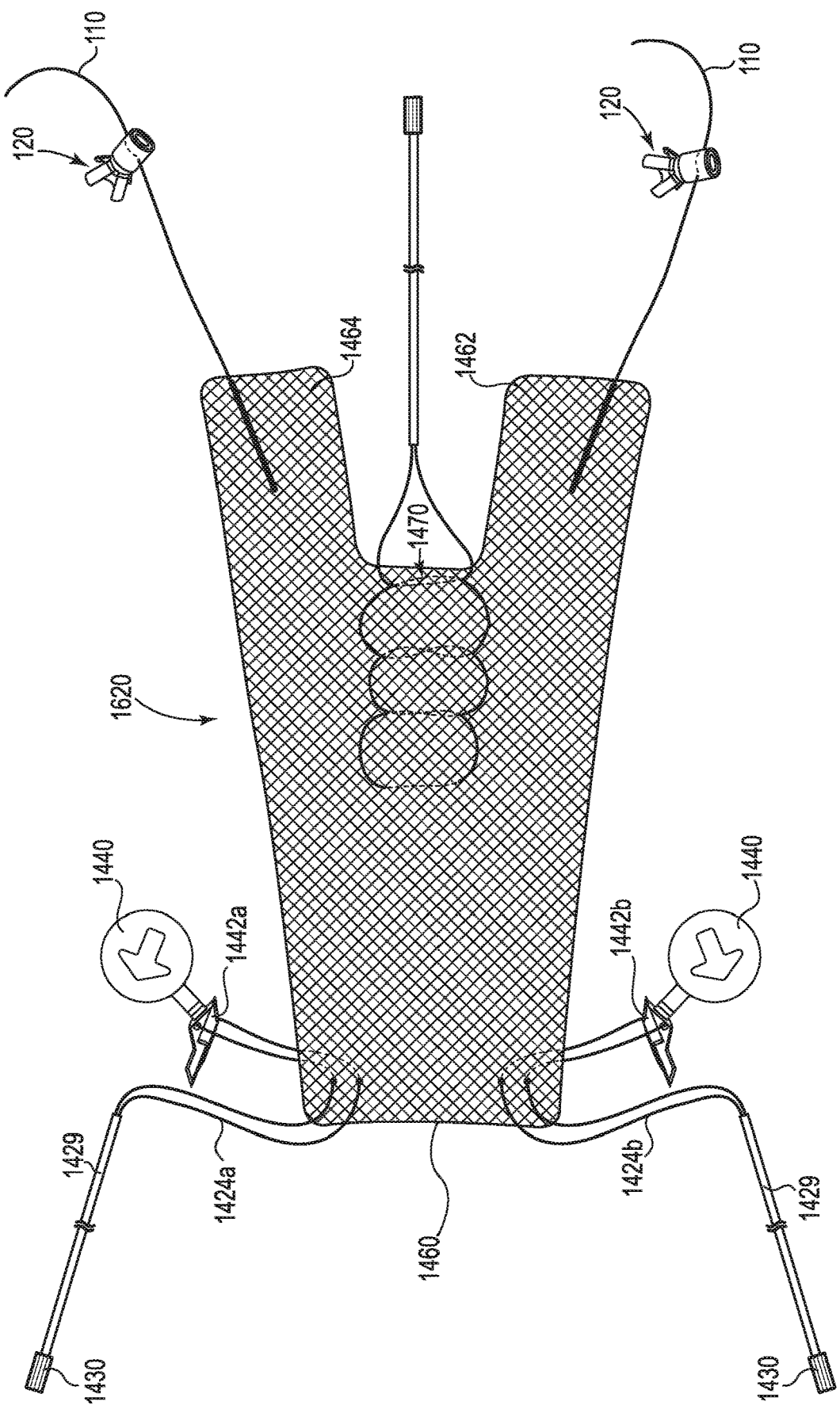
FIG. 48 is a top view of one embodiment of a tissue anchor system including two toggling anchors and two adjustable anchors attached to a support material.

FIG. 48 is a top view of one embodiment of a tissue anchor system 1620 including two toggling anchors 1442a, 1442b and two adjustable anchors 120 attached to a support material 1422. The toggling anchors 1442a, 1442b are configured to be implanted in the muscle of each opposing obturator foramen using the introducer 1428 (FIG. 28). The adjustable anchors 120 are adapted to be implanted in the periosteum tissue on either side of the pubic symphysis in the approaches discussed above. It is possible to employ fixed anchors 136 attached to the arms 1462, 1464 instead of the adjustable anchors 120. Implanting the support 1422 with the anchors 1442a, 1442b, 120 offers a single incision implantable support suitable for treatment of male urinary incontinence.

Figure 49:
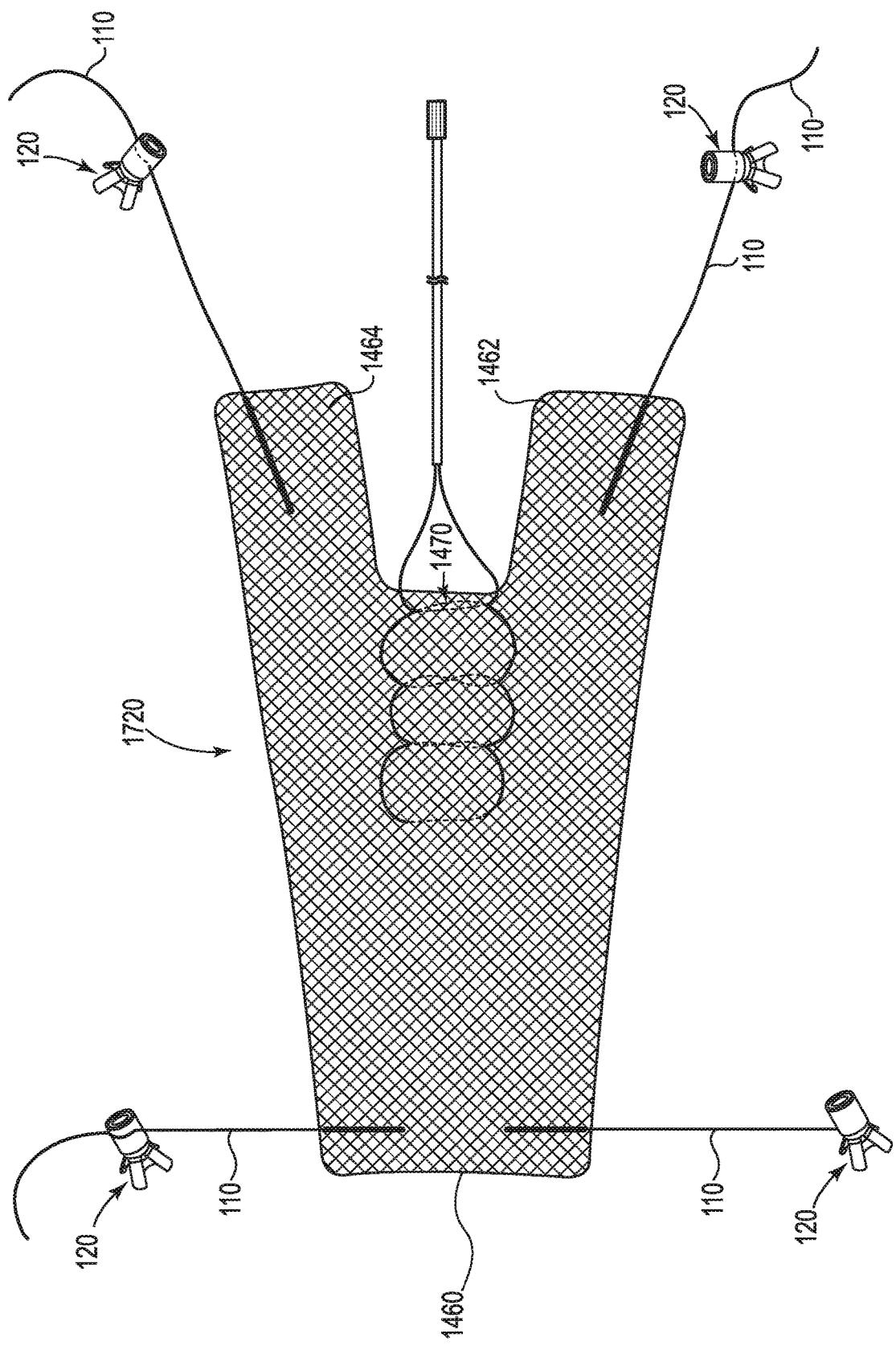
FIG. 49 is a top view of one embodiment of a tissue anchor system including four adjustable anchors attached to a support material.

FIG. 49 is a top view of one embodiment of a tissue anchor system 1720 including four adjustable anchors 120 attached to a support material. Two of the anchors 120 associated with the base 1460 are configured to be implanted in the muscle of each opposing obturator foramen using the tools 600R, 600L (FIG. 11). Two other of the anchors 120 are adapted to be implanted in the periosteum tissue on either side of the pubic symphysis in the approaches discussed above. Implanting the support 1422 with the anchors

120 offers a single incision implantable support suitable for treatment of male urinary incontinence.

Embodiments described include anchors attached to a support by a suture, where the anchors include a combination of anchor(s) having the geometric asymmetry and an asymmetric mass distribution along a length of the anchor and non-adjustable/adjustable tissue anchor(s) with a suture located between the body and the collar of the anchor.

What is claimed is:

1. An incontinence treatment device, the device comprising:
    a first anchor assembly;
    a second anchor assembly; and
    a strand;
    wherein at least one of the first anchor assembly and the second anchor assembly comprises an adjustable anchor that is positionally adjustable along the strand, the adjustable anchor comprising:
        a body defining a longitudinal body axis, and
        a collar defining a longitudinal collar axis, the collar comprising a wall, with the collar disposed over the body to locate the longitudinal body axis substantially parallel and laterally offset relative to the longitudinal collar axis;
    wherein the strand extends through the wall of the collar and is located between the body and the collar, with the strand extending around a portion of the body such that the strand is frictionally engaged between the body and the collar.

2. The incontinence treatment device of claim 1, wherein the strand extends around the body in a circumferential direction.

3. The incontinence treatment device of claim 1, wherein the body has a longitudinal channel for receiving an introducer needle.

4. The incontinence treatment device of claim 1, wherein the collar is disposed entirely around a circumference of the body.

5. The incontinence treatment device of claim 1, wherein the strand comprises at least one filament.

6. The incontinence treatment device of claim 1, wherein the strand comprises a length of suture material.

7. The incontinence treatment device of claim 1, further comprising a mesh support.

8. The incontinence treatment device of claim 7, wherein the strand is coupled to the mesh support and the adjustable anchor is bi-directionally adjustable along the strand and characterized by the strand being frictionally engaged between the body and the collar of the second anchor assembly.

9. The incontinence treatment device of claim 8, wherein the second anchor assembly comprises the adjustable anchor and the first anchor assembly comprises a fixed anchor that is coupled to an opposite side of the mesh support relative to the adjustable anchor.

10. The incontinence treatment device of claim 1, wherein the adjustable anchor further comprises a plurality of flanges that are configured to engage with tissue.

11. The incontinence treatment device of claim 1, wherein the adjustable anchor further comprises a plurality of flanges that extend in a radial direction away from the longitudinal body axis.

* * * * *

UNITED STATES PATENT AND TRADEMARK OFFICE
CERTIFICATE OF CORRECTION

PATENT NO. : 11,219,515 B2
APPLICATION NO. : 16/808379
DATED : January 11, 2022
INVENTOR(S) : Morningstar et al.

It is certified that error appears in the above-identified patent and that said Letters Patent is hereby corrected as shown below:

In the Specification

Column 1, Line 6, delete "15/632,429 filed on Jun. 26, 2017," and insert -- 15/632,429, filed on Jun. 26, 2017, now U.S. Pat. No. 10,617,504, --, therefor.

Column 1, Lines 6-7, delete "Continuation-in-Part of" and insert -- Continuation of --, therefor.

Column 9, Line 43, delete "30 C" and insert -- 30° C. --, therefor.

Column 23, Line 22, delete "hangers thousand 102" and insert -- hanger 1102 --, therefor.

Column 28, Line 56, delete "optional a plication mechanism" and insert -- optional plication mechanism --, therefor.

Column 30, Line 18, delete "additional %" and insert -- additional 1/4 --, therefor.

Column 33, Line 7, delete "then on" and insert -- than on --, therefor.

Column 35, Line 59, delete "it is in implanted" and insert -- it is implanted --, therefor.

Column 38, Line 60, delete "ejection mechanism 54." and insert -- ejection mechanism 1454. --, therefor.

Column 38, Line 63, delete "ejection mechanism 54." and insert -- ejection mechanism 1454. --, therefor.

Column 39, Lines 11-12, delete "ejection mechanism 54." and insert -- ejection mechanism 1454. --, therefor.

Column 40, Lines 54-55, delete "support 1442" and insert -- support 1422 --, therefor.

Signed and Sealed this
Fifth Day of July, 2022

*Katherine Kelly Vidal*

Katherine Kelly Vidal
*Director of the United States Patent and Trademark Office*

CERTIFICATE OF CORRECTION (continued)
U.S. Pat. No. 11,219,515 B2

Column 40, Lines 56-57, delete "support 1442" and insert -- support 1422 --, therefor.

Column 40, Line 58, delete "support 1442" and insert -- support 1422 --, therefor.

Column 40, Line 59, delete "be lengthening" and insert -- by lengthening --, therefor.

Column 40, Line 61, delete "support 1442" and insert -- support 1422 --, therefor.

Column 40, Line 63, delete "1442$c$, 42$d$" and insert -- 1442$c$, 1442$d$ --, therefor.

Column 40, Lines 65-66, delete "1424$c$, 24$d$" and insert -- 1424$c$, 1424$d$ --, therefor.

Column 40, Line 66, delete "1442$c$, 42$d$" and insert -- 1442$c$, 1442$d$ --, therefor.

Column 41, Line 42, delete "1442$c$, 42$d$" and insert -- 1442$c$, 1442$d$ --, therefor.

Column 41, Line 65, delete "cannula 28b" and insert -- cannula 1450 --, therefor.

Column 42, Line 40, delete "1442$c$, 42$d$" and insert -- 1442$c$, 1442$d$ --, therefor.